US011497680B2

(12) United States Patent
Thompson et al.

(10) Patent No.: US 11,497,680 B2
(45) Date of Patent: Nov. 15, 2022

(54) PORTABLE ENTERAL FEEDING APPARATUS

(71) Applicant: ROCKFIELD MEDICAL DEVICES LIMITED, Galway (IE)

(72) Inventors: Tomas Martin Thompson, Athenry (IE); Donal Mayne, Celbridge (IE); Damian Kelly, Galway (IE)

(73) Assignee: ROCKFIELD MEDICAL DEVICES LIMITED, Galway (IE)

( * ) Notice: Subject to any disclaimer, the term of this patent is extended or adjusted under 35 U.S.C. 154(b) by 719 days.

(21) Appl. No.: 16/469,979

(22) PCT Filed: Aug. 15, 2017

(86) PCT No.: PCT/EP2017/070692
§ 371 (c)(1),
(2) Date: Jun. 14, 2019

(87) PCT Pub. No.: WO2018/108337
PCT Pub. Date: Jun. 21, 2018

(65) Prior Publication Data
US 2020/0079576 A1    Mar. 12, 2020

(30) Foreign Application Priority Data

Dec. 16, 2016 (EP) .................................... 16204887
Dec. 16, 2016 (EP) .................................... 16204889

(51) Int. Cl.
*A61J 1/10* (2006.01)
*B05B 11/00* (2006.01)
(Continued)

(52) U.S. Cl.
CPC ................ *A61J 1/10* (2013.01); *A61M 39/08* (2013.01); *A61M 39/24* (2013.01);
(Continued)

(58) Field of Classification Search
CPC .. B65D 83/0055; B05B 11/00412; A61J 1/10; A61J 1/14; A61J 1/1493; A61J 1/1468; A61M 39/08; A61M 38/085
See application file for complete search history.

(56) References Cited

U.S. PATENT DOCUMENTS 5,372,578 A * 12/1994 Kriesel ................. A61M 5/152
604/9
5,980,489 A    11/1999 Kriesel
(Continued)

FOREIGN PATENT DOCUMENTS

DE    199 28 133 A1    12/2000
EP    0933091 A2    8/1999
(Continued)

OTHER PUBLICATIONS

An Office Action issued by the Indian Patent Office dated Oct. 5, 2021, which corresponds to Indian Patent Application 201917023764 and is related to U.S. Appl. No. 16/469,979.
(Continued)

Primary Examiner — Nathan R Price
Assistant Examiner — Melissa A Snyder
(74) Attorney, Agent, or Firm — Studebaker & Brackett PC

(57) ABSTRACT

An enteral feeding apparatus includes a pod having an expansile pouch which defines a reservoir for enteral fluid and a gas impermeable barrier surrounding the pouch. The pod has an inlet port for delivery of enteral fluid into the pouch and an outlet port having a seal which is pierceable to release enteral fluid from the pouch for delivery to a PEG via a feeding line. The expansile pouch provides the sole force by which enteral fluid is delivered from the pouch through a regulator. The system can accommodate a range of enteral fluids with a wide range of viscosities.

13 Claims, 68 Drawing Sheets

(51) Int. Cl.
*A61M 39/08* (2006.01)
*A61M 39/24* (2006.01)
*B65D 83/00* (2006.01)

(52) U.S. Cl.
CPC .... *B05B 11/00412* (2018.08); *B65D 83/0055* (2013.01); *A61M 2039/085* (2013.01); *B65D 2203/10* (2013.01)

(56) References Cited

U.S. PATENT DOCUMENTS

| | | | |
|---|---|---|---|
| 5,993,425 | A | 11/1999 | Kriesel |
| 8,021,322 | B1 | 9/2011 | Francis |
| 2003/0202719 | A1* | 10/2003 | Wilkes ............... B29C 66/1122 383/120 |
| 2004/0138627 | A1 | 7/2004 | Forrest |
| 2008/0255498 | A1* | 10/2008 | Houle ............... A61C 17/0208 604/20 |
| 2009/0022985 | A1 | 1/2009 | Smith et al. |
| 2013/0178833 | A1* | 7/2013 | Sacchetti ............... B65H 54/04 604/151 |
| 2014/0207068 | A1 | 7/2014 | Silver |

FOREIGN PATENT DOCUMENTS

| | | | |
|---|---|---|---|
| WO | 95/14503 | A1 | 6/1995 |
| WO | 96/37253 | A1 | 11/1996 |
| WO | 2014/043499 | A1 | 3/2014 |
| WO | 2014/179594 | A2 | 11/2014 |
| WO | 2014/179594 | A3 | 11/2014 |

OTHER PUBLICATIONS

The extended European search report issued by the European Patent Office dated Dec. 7, 2021, which corresponds to EP 21197282.3-1001 and is related to U.S. Appl. No. 16/469,979.
International Search Report issued in PCT/EP2017/070692; dated Oct. 26, 2017.
Written Opinion issued in PCT/EP2017/070692; dated Oct. 26, 2017.
"Enteral Feeding Connectors (ENFit®)" StayConnected by GEDSA. [Online] http://stayconnected.org/enteral-enfit/.
Spectra Symbol, "Spectra SymbolFlex Sensor 4.5 Inch" [Online] https://www.amazon.com/SPECTRA-SYMBOL-FS-L-0112-103-ST-SYMBOLFLEX-SENSOR/dp/B005T8743E.
"Ultrasonic Flowmeter Technology," Universal Flow Monitors [Online] http://www.flowmeters.com/ultrasonic-technology.
"UF31210 Clamp-on Ultrasonic Flow Sensor," Strain Measurement Devices [Online] https://www.smdsensors.com/products/type/uf31210-clamp-on-ultrasonic-flow-sensor/.
"Bidirectional In Line Flow Meter," Strain Measurement Devices [Online] https://www.smdsensors.com/products/type/bidirectional-in-line-flow-meter/.
"SF800—Low Pressure Flow Meter," Swissflow The Art of Measurement [Online] http://www.swissflow.com/sf800.html.

* cited by examiner

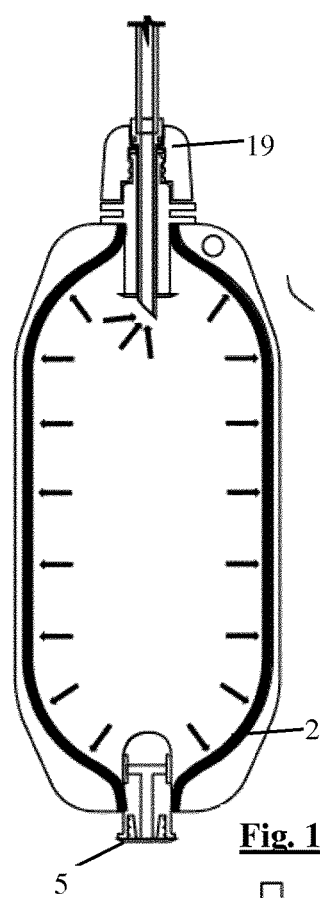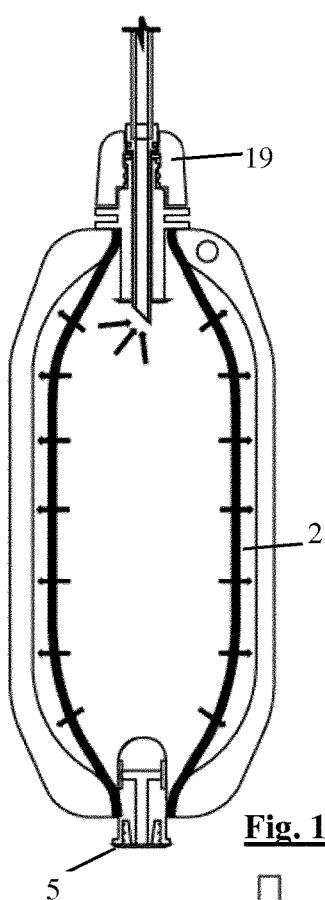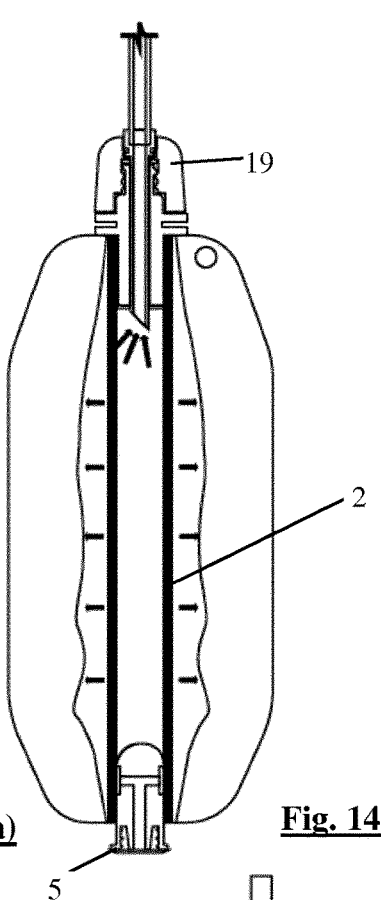
Fig. 12(a)  Fig. 13(a)  Fig. 14(a)
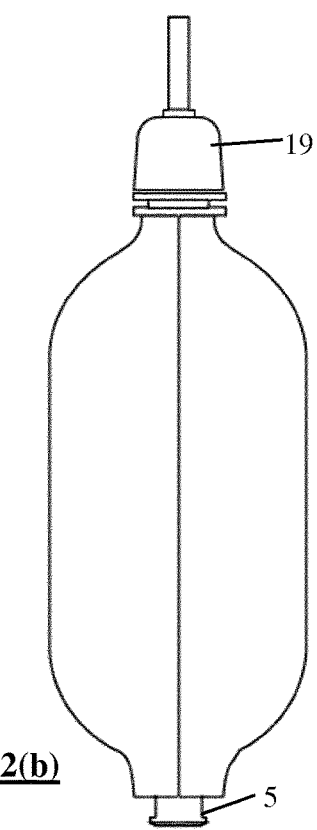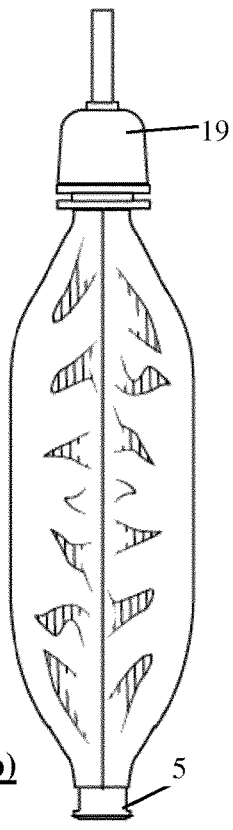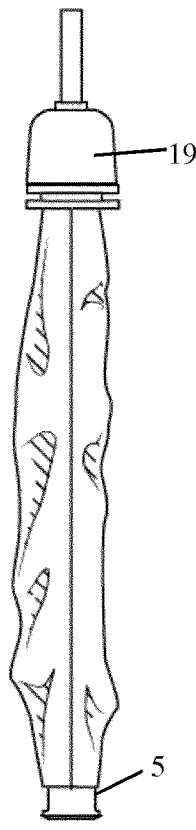
Fig. 12(b)  Fig. 13(b)  Fig. 14(b)

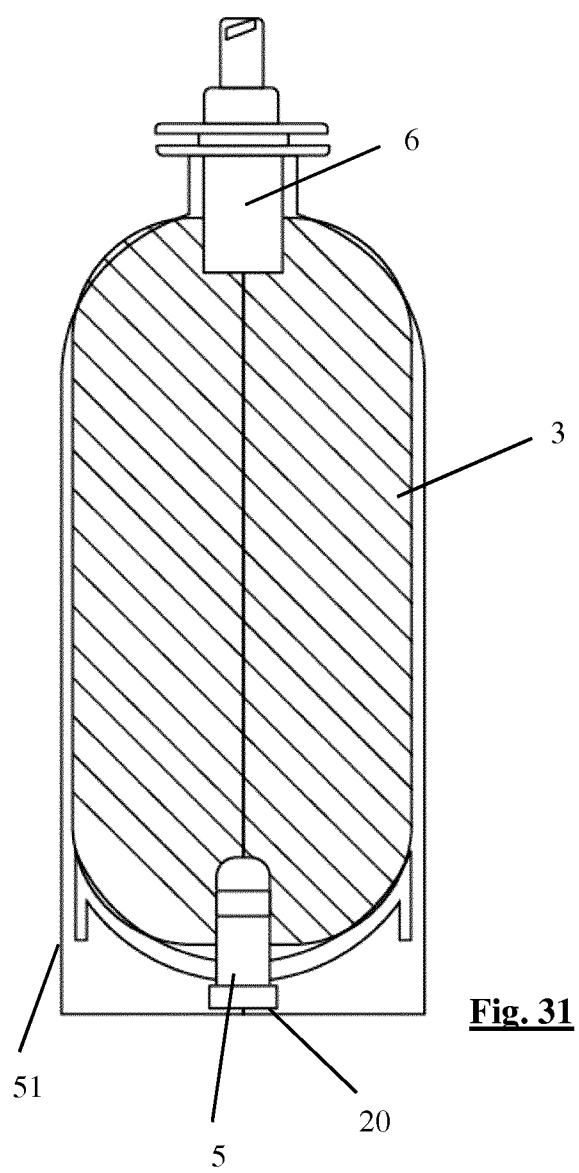
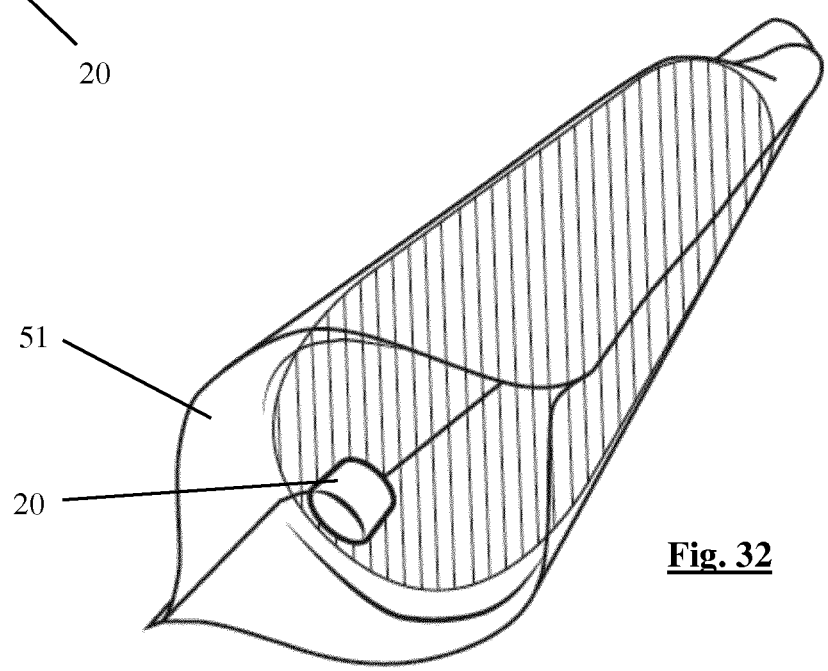
Fig. 31
Fig. 32

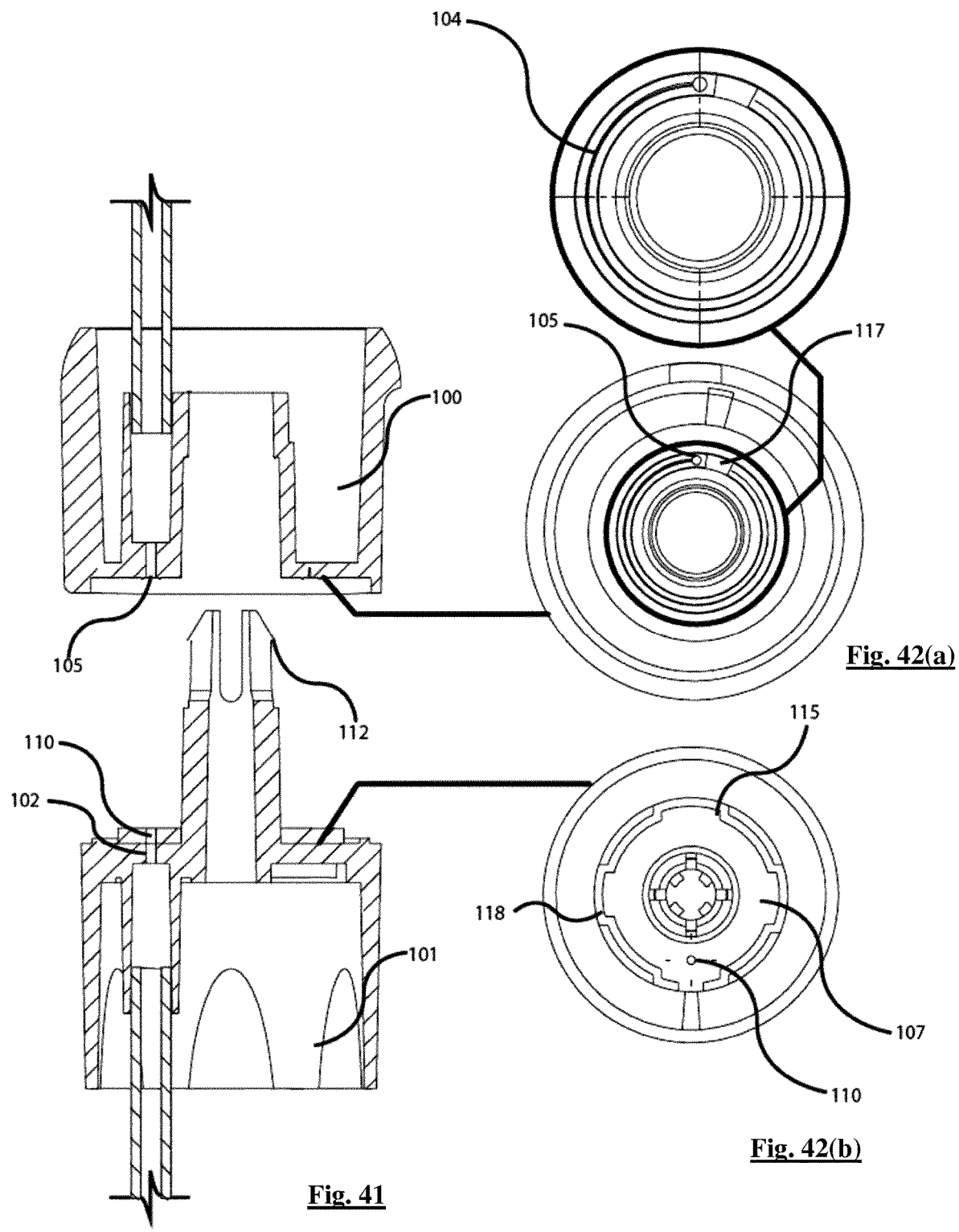

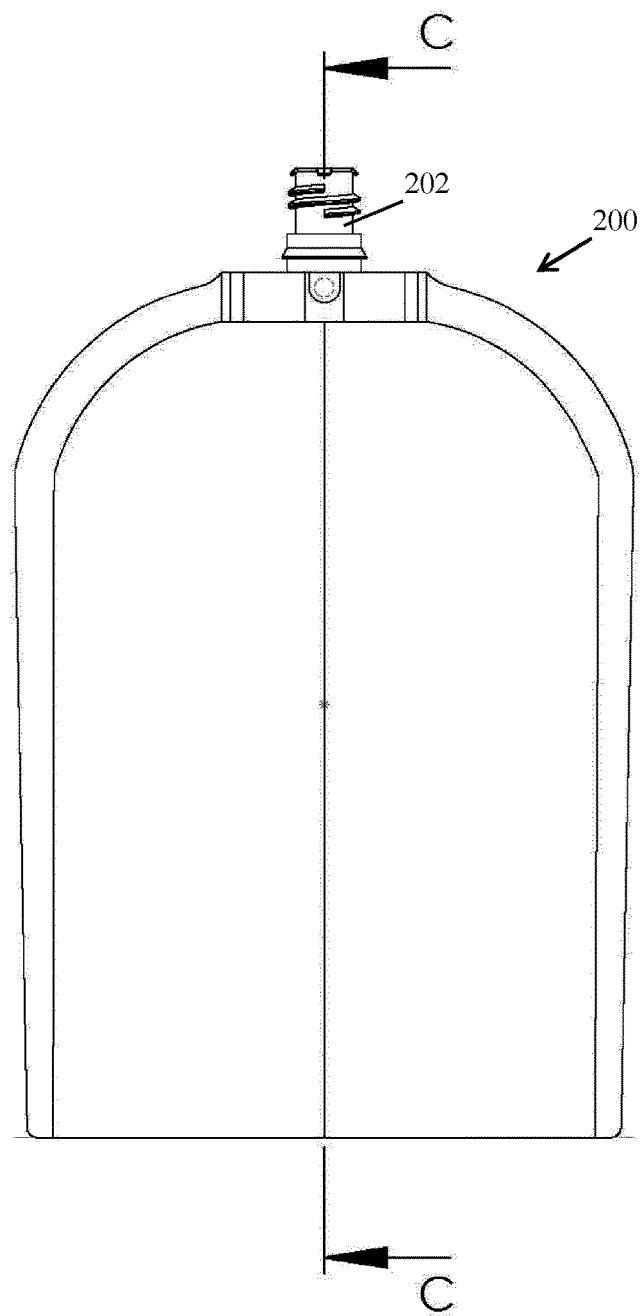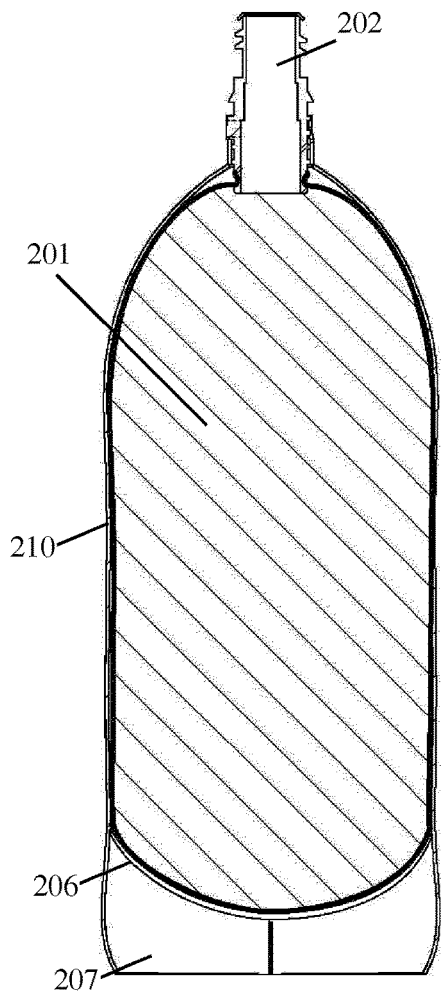
Fig. 68
Fig. 69

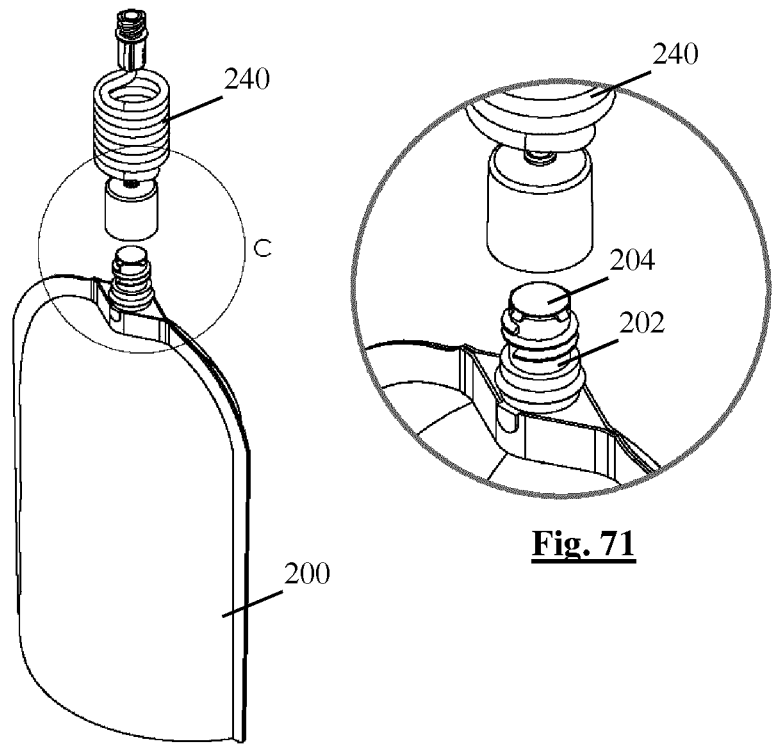
Fig. 70
Fig. 71
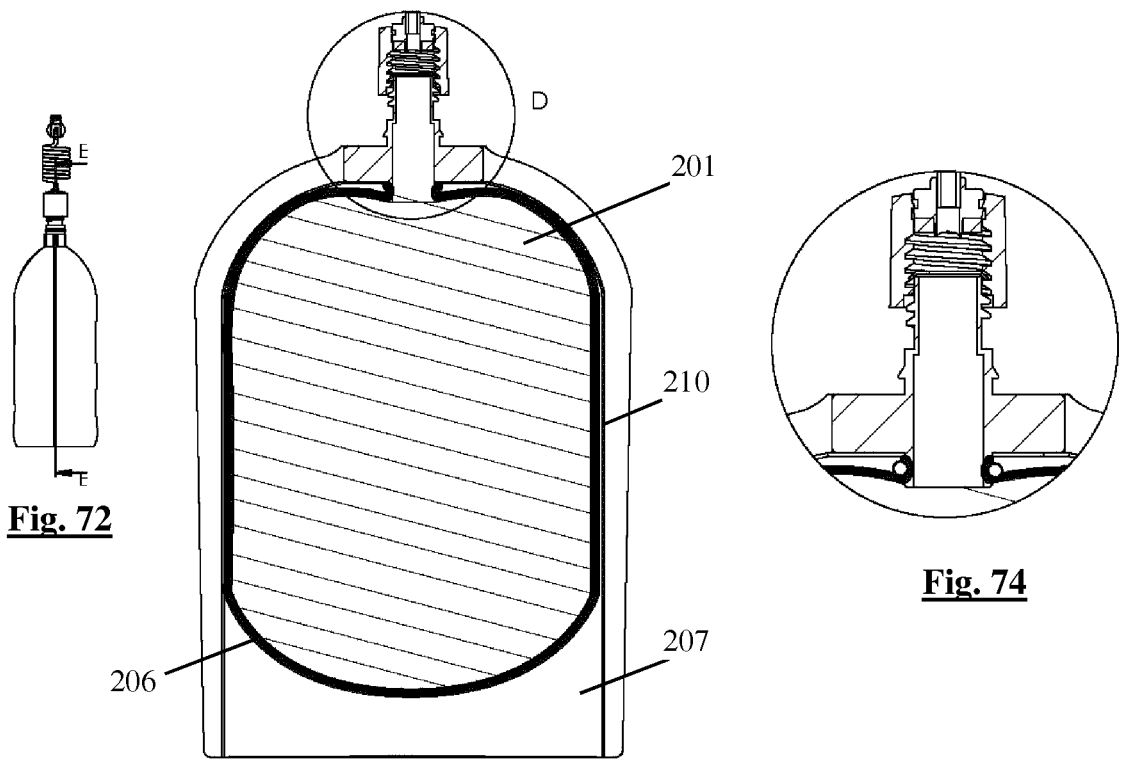
Fig. 72
Fig. 73
Fig. 74

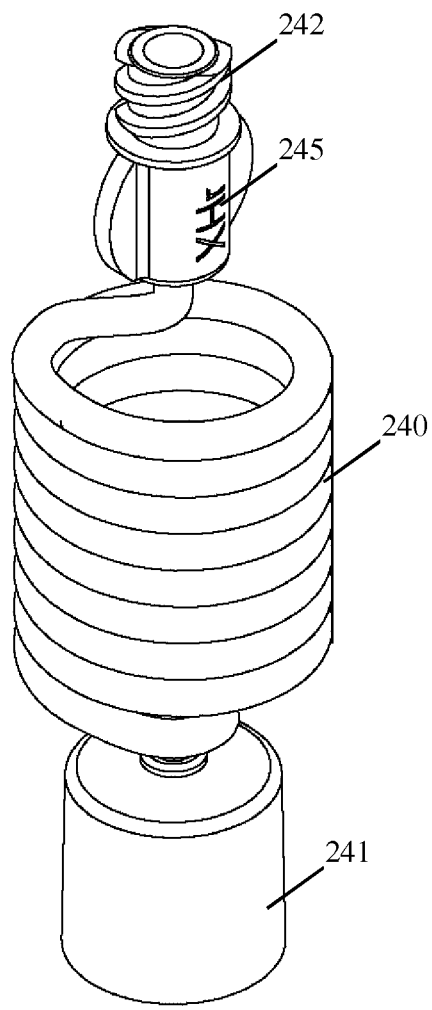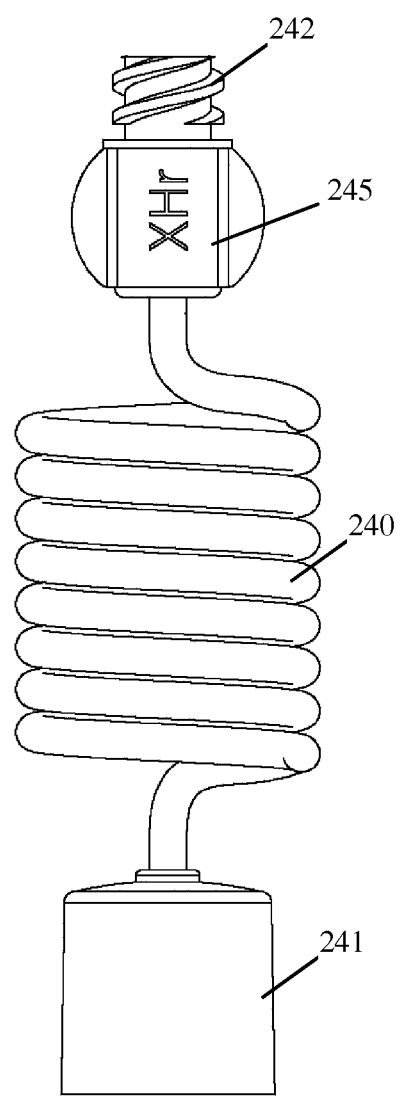
Fig. 100
Fig. 101

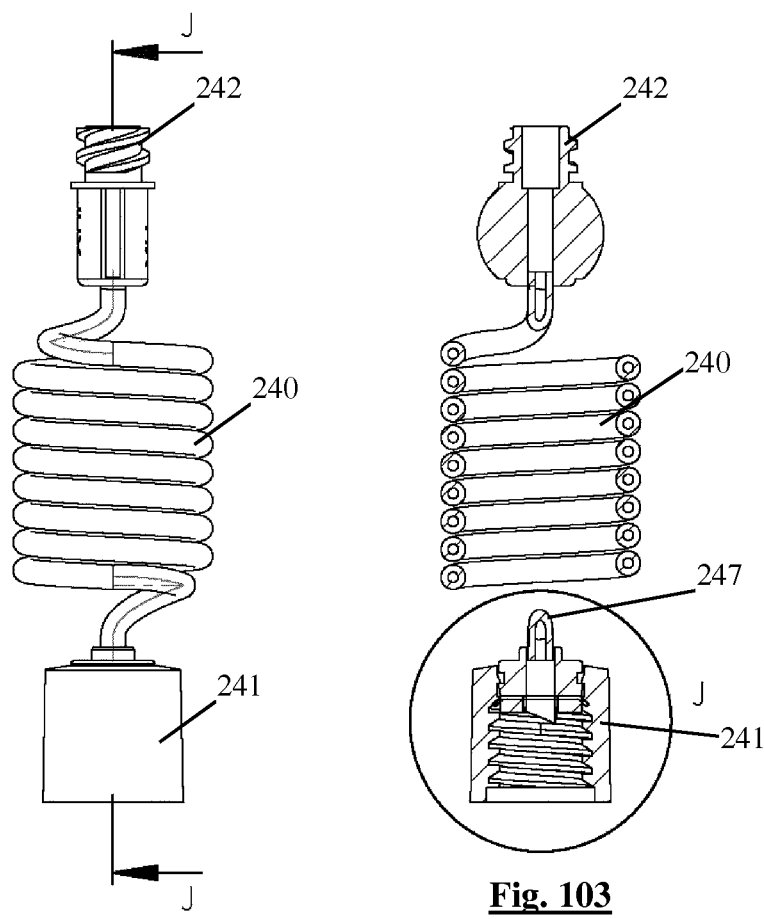
Fig. 102
Fig. 103
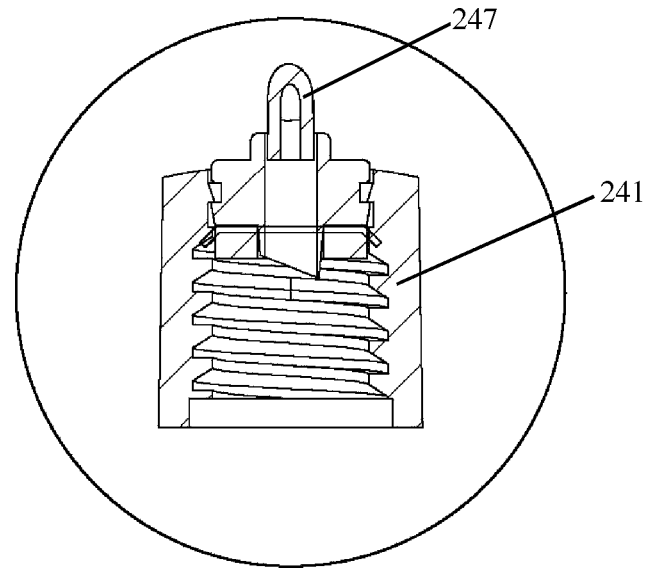
Fig. 104

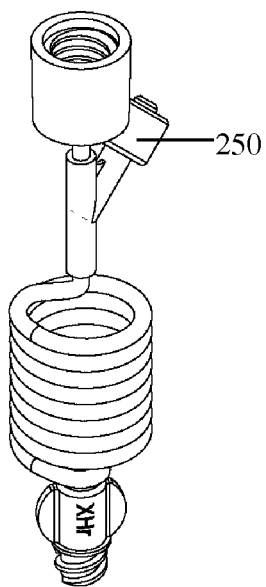
Fig. 109
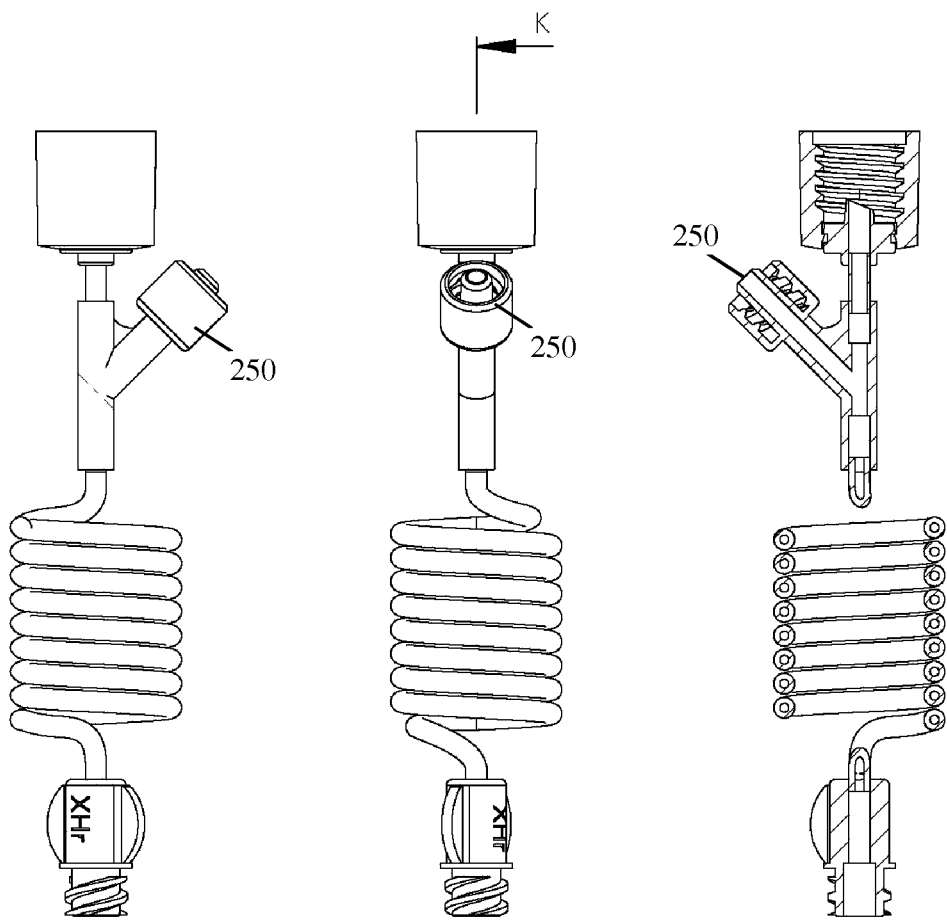
Fig. 110
Fig. 111
Fig. 112
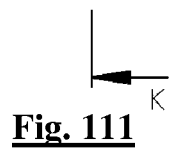

PORTABLE ENTERAL FEEDING APPARATUS

INTRODUCTION

Enteral feeding or tube feeding is used worldwide by people who are unable to voluntarily eat or swallow food. Enteral feeding delivers the required nutrition to these people using a pump driven electrically from a mains supply or a battery. The pump administers a prescription formula directly into the stomach or nasal system, through a tube which is surgically inserted.

A PEG (Percutaneous Endoscopic Gastronomy) is a fixture which is inserted into a patients stomach which allows a feeding tube coming from a pump to be attached for feeding to commence. Some of the reasons why patients require a PEG are head trauma, stroke, collagen vascular disorder and cancers such as head, throat or oesophageal. Other reasons behind requiring enteral feeding can occur from needing to gain weight via a pre port option, which is used by people who can't get the required calories from their normal diet; neurological conditions such as motor neuron disease, brain tumour, Parkinson's disease or as a result of a brain injury. Surgical conditions such as preoperative or postoperative surgery, burns, or pancreatitis; a psychiatric issue like anorexia nervosa; or disorder such as cystic fibrosis may also require enteral feeding.

Some of the problems with current technology used in enteral feeding include the noise and vibrations of the pump used to deliver the liquid formula, the difficulty that users can experience when setting up the pump and, most importantly, the restriction to the persons mobility. Conventional feeding systems involve pumps which are battery or electronically powered. Noise and vibrations are produced which can be very disturbing, especially when trying to sleep at night. When feeding at home, patients are required to be lying down or seated, then the pump is placed on an IV type stand with the bag held higher over the pump. A single serving of approximately 500 ml to 1000 ml can take from 4 to 24 hours to be administrated, but this is entirely dependent of the patient, as serving a feeding too fast can lead to stomach pains or vomiting, and releasing the formula too slow will have less effect and leave the patient tired and lacking in energy.

It is also necessary to have this setup beside their bed for night feeding. Slower feed rates are generally used at night for a longer release of food for the patient. Patients often find it difficult and irritating, when trying to sleep with the constant noise, vibration and also visual impact (lighting) of the pump.

When a patient is not at home they are required to use a special carry bag for the pump, formula, tubing and all other equipment needed. The conventional carry bag is approximately the same size of an average back pack. It allows the user to feed, while preforming some tasks but it is restrictive. Gravity is required to allow flow from a container for enteral fluid to a pump. The pump also requires an electricity supply and/or a battery pack. The units must also be programmed using a complex interface. The current portable systems are heavy and bulky which means that they are not very mobile and are not discrete.

STATEMENTS OF INVENTION

According to the invention there is provided a portable enteral feeding apparatus comprising a pouch which defines a reservoir for enteral fluid and having an outlet for delivery of enteral fluid from the pouch, the pouch being formed by an expansile element having an expanded filled configuration and a collapsed configuration, the expansion of the expansile element providing the sole force under which enteral fluid is delivered from the pouch. In one embodiment the apparatus further comprises a substantially gas impermeable barrier surrounding the pouch.

In one case, when the pouch is filled with enteral fluid, the pouch substantially conforms to the shape of the inner surface of the surrounding barrier.

In one case, as fluid is delivered from the pouch, a space is formed between the pouch and the barrier.

An exhaust passageway may be provided to facilitate exhaust of gas from between the outer barrier and the expansile element, on filling.

In one embodiment the barrier comprises a membrane. The membrane may comprise a laminate including a metallic layer. In some cases the membrane comprises a PET layer.

In some embodiments the enteral feeding apparatus comprises an inner barrier which is surrounded by the expansile element.

The inner barrier may have a collapsed empty configuration and an expanded filled configuration. The inner barrier may be folded, compressed, and/or rolled in the collapsed configuration and the membrane unfolds and/or unrolls on moving from the collapsed configuration to the expanded configuration.

In one case the inner barrier has an inner surface which is adapted for contacting with enteral fluid and an outer surface which substantially conforms to the inner surface of the expansile element in the expanded filled configuration.

In one embodiment the inner barrier comprises a membrane. The membrane may comprise PET.

The outer barrier may be formed from a membrane such as a laminate. The final shape may be manufactured from a blank which is sealed along adjoining edges. The barrier may comprise front and rear panels and foldable side panels.

In one case the apparatus is free-standing. The apparatus may comprise a bottom gusset.

In one embodiment the enteral feeding apparatus further comprises a regulator for regulating the flow of enteral fluid from the pouch.

In one case the regulator comprises a flow channel and means for adjusting the bore of the flow channel.

Alternatively or additionally the regulator comprises a friction regulator.

In one embodiment the regulator comprises a coiled tube. There may be a plurality of coiled tubes. The coiled tubes may be configured for engagement with one another to adjust the length of the regulator.

In one case the coil comprises an inlet port having engagement features for engagement with a Leur or ENFit connector.

In one case the coil comprises an outlet port having engagement features for engagement with a Leur or ENFit connector.

In one case a coil may have a side port for delivery directly into the flow line. This may be used for flushing or delivery of a medicament, for example.

In one embodiment the pressure applied by the expansile element in the expanded configuration is from 0.05 to 900 psi (0.000345 to 6.2053 MPa), from 0.05 to 90 psi (0.000345 to 0.62053), from 0.5 to 3.0 psi (0.003447 to 0.0206843 MPa), from 1.0 to 2.5 psi (0.006895 to 0.017237 MPa), or from 1.0 to 2.0 psi (0.006895 to 0.0137895 MPa).

In some embodiments the volume of the expansile element in the expanded filled configuration is from 50 ml to 1000 ml, 250 to 750 ml, 400 to 600 ml, or approximately 500 ml.

In some embodiments the wall thickness of the expansile element in the expanded filled configuration is from 0.01 to 1.0 mm, 0.05 to 1.0 mm, 0.1 to 0.5 mm, or approximately 0.2 mm. In one embodiment the secant modulus of elasticity of the expansile element in the expanded filled configuration at a circumferential extension of from 100% to 1000% is from 0.1 to 4.5 MPa.

In one case the secant modulus of elasticity of the expansile element in the expanded filled configuration at a circumferential extension of from 300% to 500% is from 0.1 to 1.6 MPa, from 0.1 to 1.0 MPa, or approximately 0.5 MPa.

In some embodiments the apparatus is configured to deliver a flowrate of from 1 to 1500 ml/hr, 50 to 1000 ml/hr, 250 to 750 ml/hr or approximately 500 m/hr.

In one case the expansile element comprises a silicon elastomer.

The expansile element may comprise a two component silicone rubber that vulcanises at room temperature.

The enteral feeding apparatus may further comprise an indicator such as a smart label or a Near Field Communication tag.

In some cases the enteral feeding apparatus further comprises a sensor for detecting properties associated with enteral food.

In some cases the sensor may, for example be a weight sensor, a volume sensor, a pressure sensor, and/or a flow sensor.

In one embodiment the outlet port comprises a seal. The seal may be of a pierceable material such as a foil.

In some embodiments the delivery port comprises engagement features for engagement with a Leur or ENFit connector.

There may be a removable cap for the outlet port.

In one case the portable enteral feeding apparatus comprises an inlet port for delivery of enteral fluid into the pouch. The inlet port may comprise engagement features for engagement with a Leur or an ENFit connector. The inlet port may comprise a seal.

In some cases the inlet port comprises a valve.

In one case the inlet port comprises a non return valve.

In one embodiment the portable enteral feeding apparatus comprises mounting means for mounting the apparatus to a stand.

In one case the apparatus comprises a spacer located within the elastomeric element. The spacer may comprise an elongate rod.

The invention also provides an enteral feeding system comprising an enteral feeding apparatus of the invention and a feeding tube having a Leur or ENFit connector at a first end for connection to the pouch outlet and a Leur or ENFit connector at a second end for connection to a PEG fixture.

The system may comprise a regulator for regulating the flow of enteral fluid from the pouch.

The invention also provides an enteral feeding system comprising an enteral feeding apparatus of the invention and a regulator for regulating the flow of enteral fluid from the pouch.

In one case the regulator comprises a flow channel and means for adjusting the bore of the flow channel.

Alternatively or additionally the regulator comprises a friction regulator.

In one embodiment the regulator comprises a coiled tube.

The enteral feeding system may comprise a plurality of coiled tubes.

In one case the coiled tubes are configured for engagement with one another to adjust the length of the regulator.

In some cases the coil comprises an inlet port having engagement features for engagement with a Leur or ENFit connector.

In some cases the coil comprises an outlet port having engagement features for engagement with a Leur or ENFit connector.

According to the invention there is provided a portable enteral feeding apparatus comprising a pouch which defines a reservoir for enteral fluid, an outlet port for delivery of enteral fluid from the pouch, the apparatus having an expansile element which is adapted to provide the force by which enteral fluid is delivered from the pouch through the outlet port.

In one embodiment the pouch comprises the expansile element, the pouch having an expanded filled configuration and a collapsed configuration.

The expansile element may comprise an expansile polymeric material.

In some embodiment the enteral feeding apparatus further comprises a substantially gas impermeable barrier surrounding the pouch.

In one case, when the pouch is filled with enteral fluid, the pouch substantially conforms to the shape of the inner surface of the surrounding barrier.

As fluid is delivered from the pouch, a space may be formed between the pouch and the barrier.

In some embodiments the barrier comprises a membrane such as a gas impermeable membrane, for example, a metallic foil.

In one embodiment the apparatus is free-standing.

The apparatus may have a base support.

In some embodiments the enteral feeding apparatus further comprises an indicator such as Near Field Communication tag.

In one embodiment the enteral feeding apparatus further comprises a sensor for detecting properties associates with enteral food.

The sensor may be a weight sensor, a volume sensor and/or a pressure sensor.

In one case the outlet port comprises a seal. The seal may be of a pierceable material such as a foil.

In one embodiment the delivery port comprises engagement features for engagement with a Leur or ENFit connector for connection to an enteral tube feeding fixture.

In one case the portable enteral feeding apparatus comprises a removable cap for the outlet port.

In some embodiments the portable enteral feeding apparatus comprises an inlet port for delivery of enteral fluid into the pouch.

The inlet port may comprise engagement features for engagement with a Leur or an ENFit connector.

In one case the inlet port comprises a seal.

The portable enteral feeding apparatus may comprise mounting means for mounting the apparatus to a stand.

The invention also provides an enteral feeding system comprising an enteral feeding apparatus of the invention and a feeding tube having a Leur or ENFit connector at a first end for connection to the pouch outlet and a Leur or ENFit connector at a second end for connection to a PEG fixture.

In one embodiment the enteral feeding system further comprises a regulator for regulating the flow of enteral fluid to the PEG.

BRIEF DESCRIPTION OF THE DRAWINGS

The invention will be more clearly understood from the following description of an embodiment thereof, given by way of example only, with reference to the accompanying drawings, in which:

FIGS. 12, 13 and 14 illustrate the collapsing of the pouch, in use;

FIGS. 30 to 32 illustrate another enteral feeding apparatus according to the invention;

FIGS. 37 to 44 illustrate a regulator of a feeding set according to the invention;

FIG. 68 is a view similar to FIG. 66 with the filling port sealed;

FIG. 69 is a cross sectional view on the line CC in FIG. 68;

FIG. 70 is an exploded view of a pouch with a coil regulator;

FIG. 71 is an enlarged view of detail C of FIG. 70;

FIG. 72 is a view of the pouch;

FIG. 73 is a cross sectional view on the line EE of FIG. 72;

FIG. 74 is an enlarged view of detail D of FIG. 73;

FIGS. 94 to 101 are views of various regulator coils;

FIG. 102 is another view of a regulator coil;

FIG. 103 is a cross sectional view on the line JJ of FIG. 102;

FIG. 104 is an enlarged view of detail J of FIG. 104;

FIGS. 109 to 112 are various views of another regulator coil;

DETAILED DESCRIPTION

Figure 1:
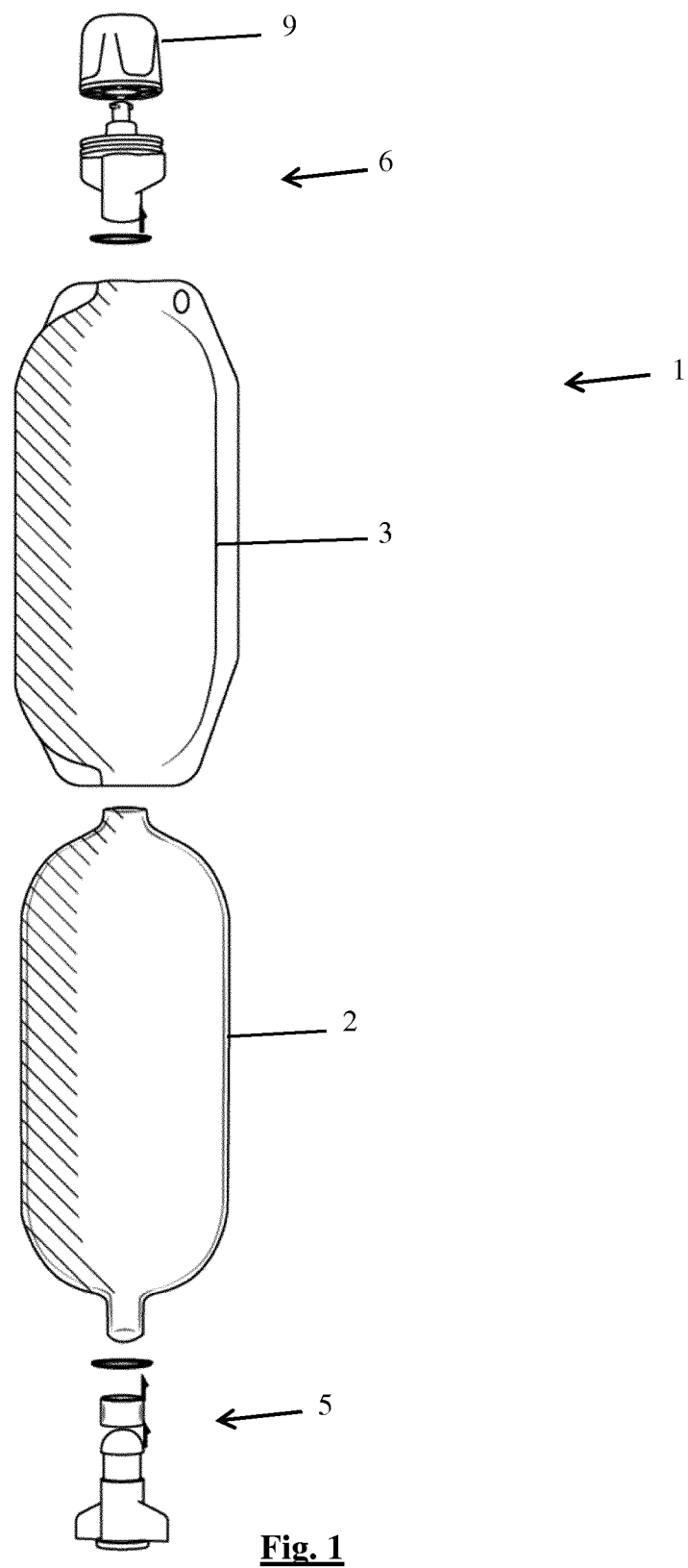
FIG. 1 is an isometric exploded view of an enteral feeding apparatus according to the invention.
Figure 2:
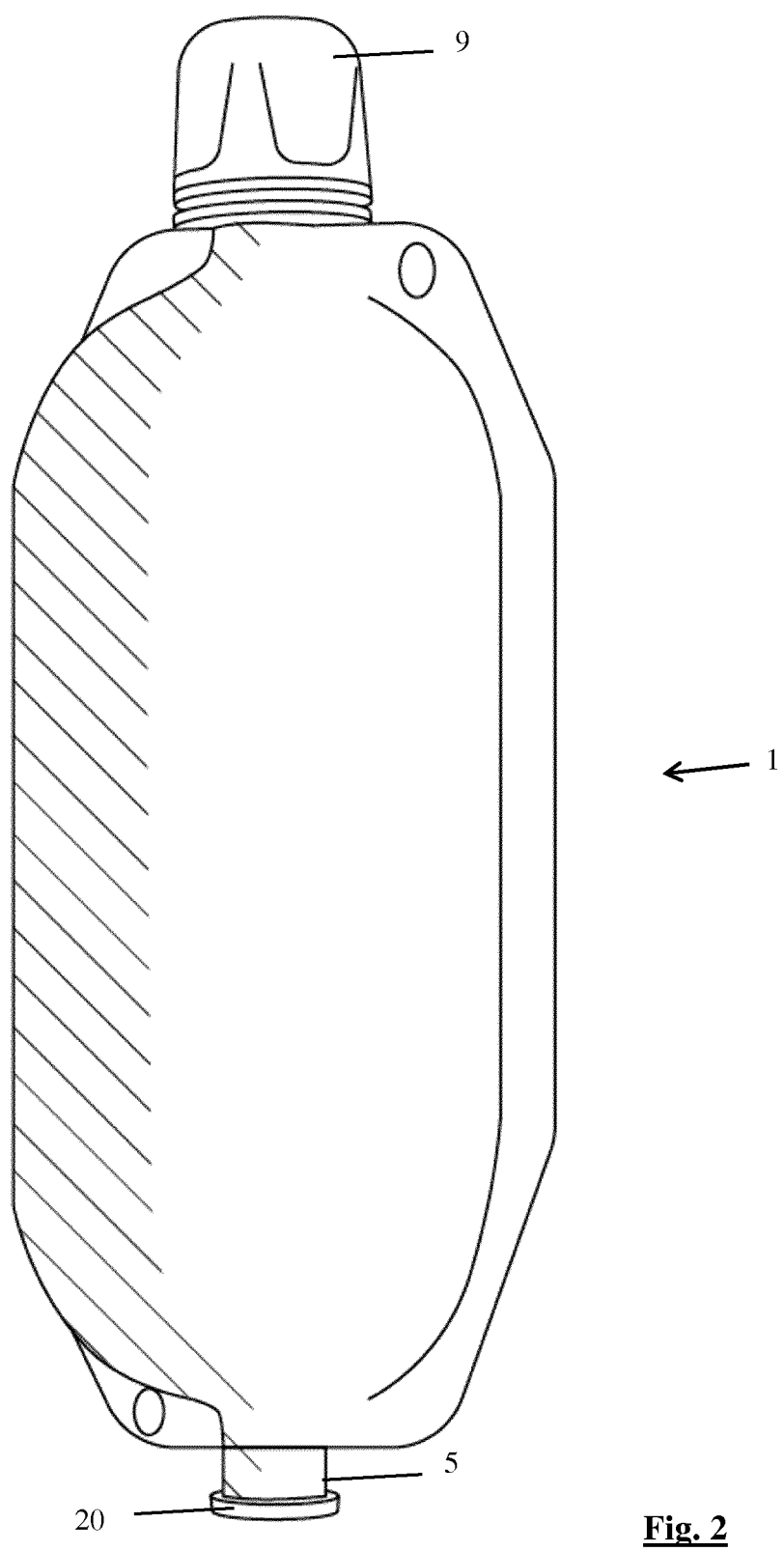
FIG. 2 is a view of the assembled apparatus of FIG. 1.
Figure 3:
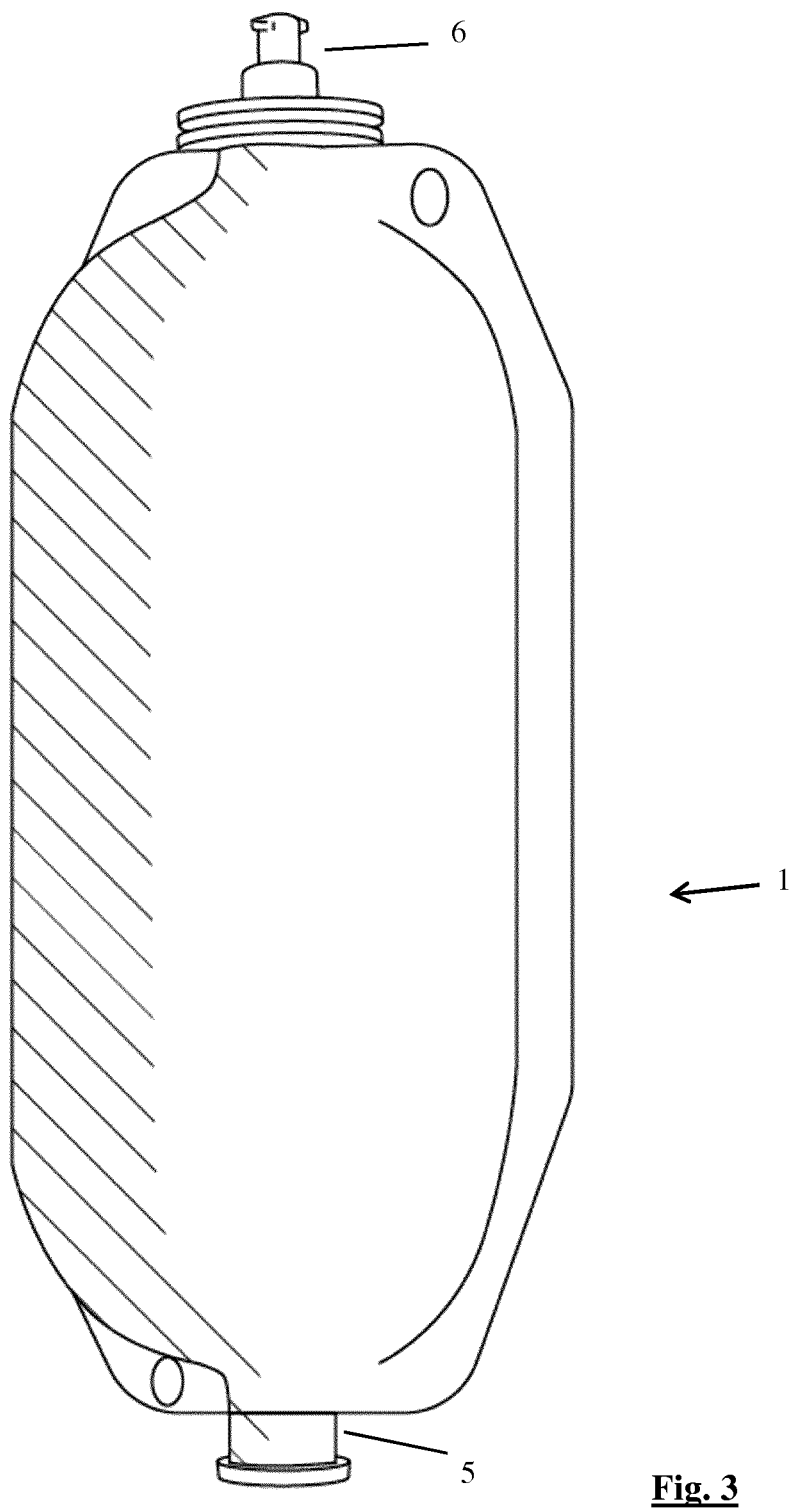
FIG. 3 is another view of the apparatus with a cap for the delivery port removed.
Figure 4:
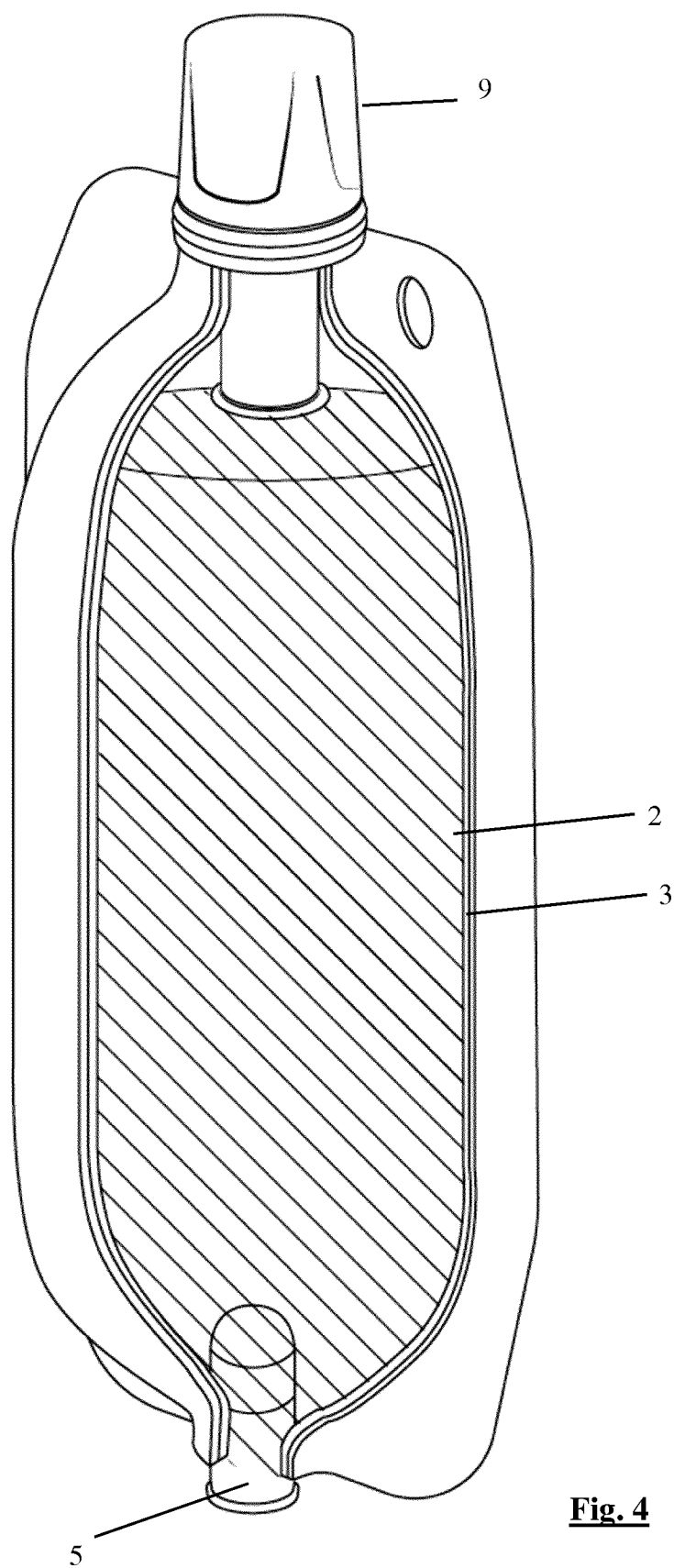
FIG. 4 is a partially cut-away view of the apparatus.
Figure 5:
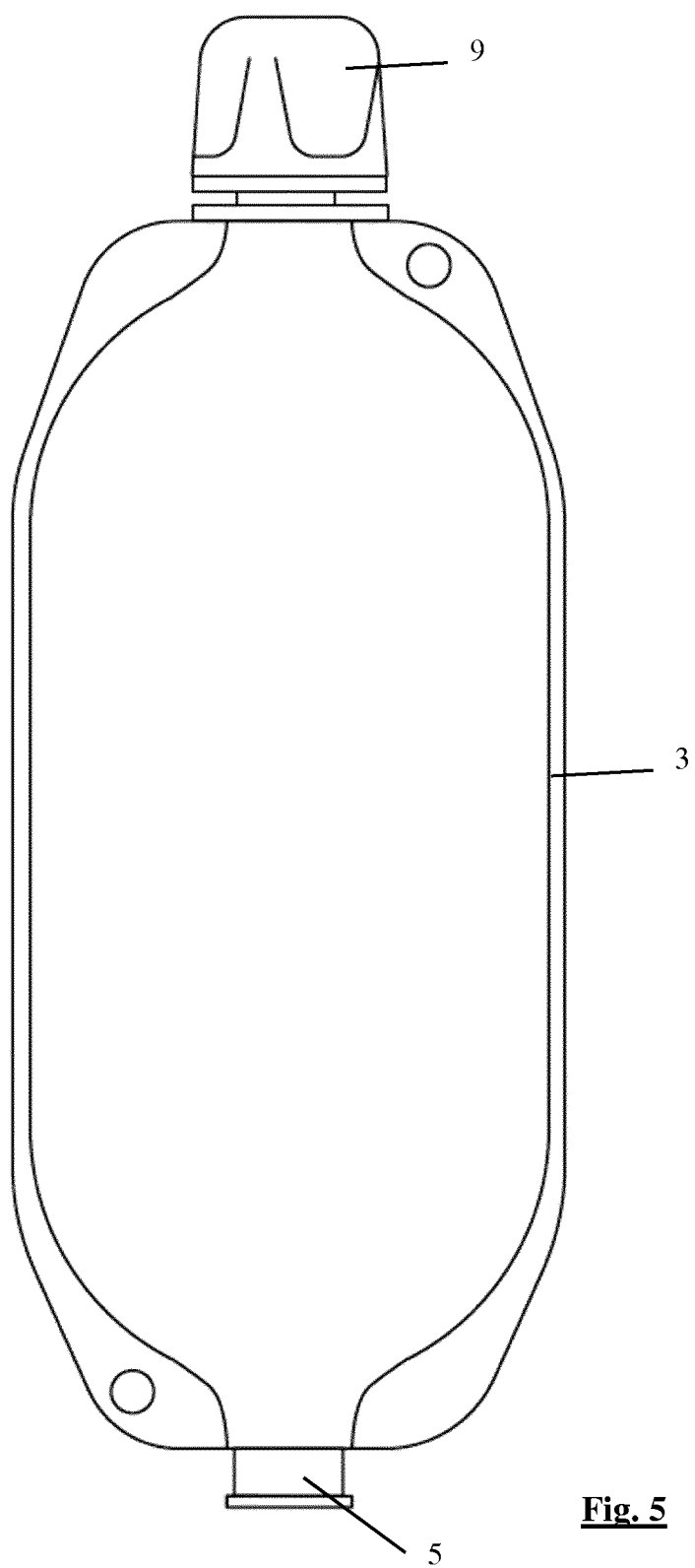
FIG. 5 is a view of an outer barrier of the apparatus.

The invention provides patients with an enteral feeding system that is comfortable, portable and adaptable to both therapy and lifestyle.

Referring to the drawings, there is illustrated an enteral feeding apparatus 1 in the form of a pod which may be pre-loaded or self filled with enteral fluid. The apparatus comprises an expansile pouch 2 which defines a reservoir for enteral fluid and a barrier 3 which surrounds the pouch 2. The apparatus comprises an inlet port 5 for delivery of enteral fluid into the pouch 2 and an outlet port 6 for delivery of enteral fluid from the pouch 2. The outlet port 6 includes a seal such as a foil 7 which is pierceable to release enteral fluid from the pouch 2. A removable cap 9 closes the outlet port 6.

The pouch 2 is expansile from a collapsed empty configuration to an expanded filled configuration. The expansile pouch 2, when filled, provides the force by which enteral fluid is delivered from the pouch through the outlet port 6. As enteral fluid is delivered from the pouch it starts to collapse. The barrier 3 is substantially impermeable to gas and protects the contents of the expansile pouch from spoilage in storage caused by air passing through the wall of the expansile pouch. The barrier 3 is also partially collapsible, however, in one case the barrier collapses to a larger volume than that of the pouch as it collapses. In this way, a space is defined between the pouch and the barrier into which gas (such as Nitrogen used in filling) from the pouch passes and is retained by the barrier. The barrier may comprise a membrane which is substantially gas impermeable. For example, the barrier may comprise a foil, especially a metallic foil such as an aluminium foil.

The outlet 6 from the feeding pod is connected to a feeding tube 10 which has a Leur or ENFit connector 11 for connection to an inlet 12 to a PEG (percutaneous endoscopic gastronomy) fixture. ENFit connectors are described, for example, at http://stayconnected.org/applications/enteral/.

A regulator 15 is provided on the feeding line. In one case the regulator is adapted to adjust the bore of the passageway through which the fluid passes. The regulator 15 is adjustable between at least three different positions corresponding to an off position, a fully on position, and at least one intermediate position.

As the reservoir is being filled with the enteral fluid through the inlet port 5, the elastomeric material of the pouch 2 expands. When the reservoir is filled, a cap or seal 20 is placed on the inlet. A gas escape route may be provided.

FIG. 1 is an exploded view which illustrates the inner pouch 2, external barrier 3, inlet port 5 and outlet port 6 including the removable cap 9.

FIGS. 2 to 5 illustrate the assembled apparatus.

Figures 6A, 6B, 6C:
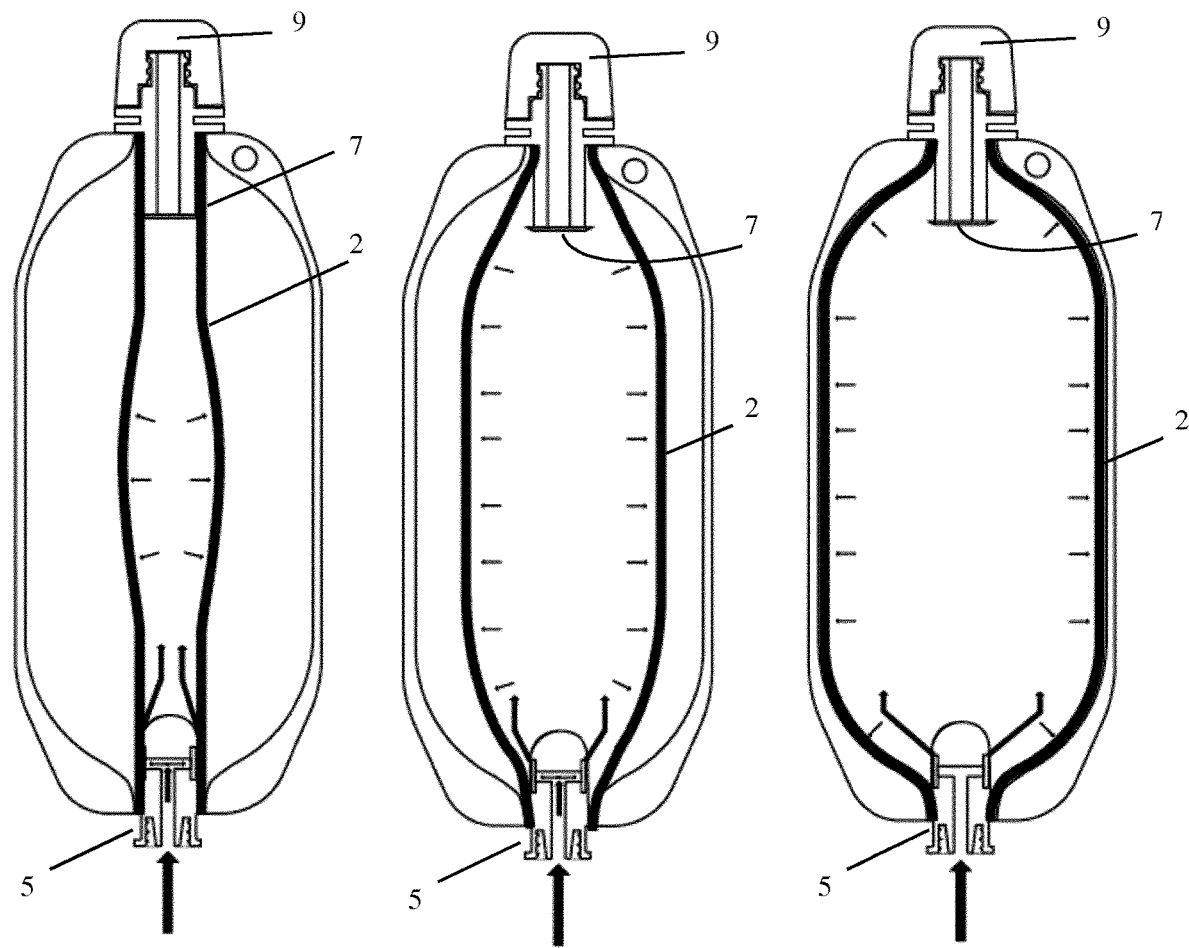
FIGS. 6(a) to 6(c) illustrate the filling of the pouch.

FIGS. 6(a) to 6(c) illustrate the filling of the pouch through the inlet port 5.

Figure 7:
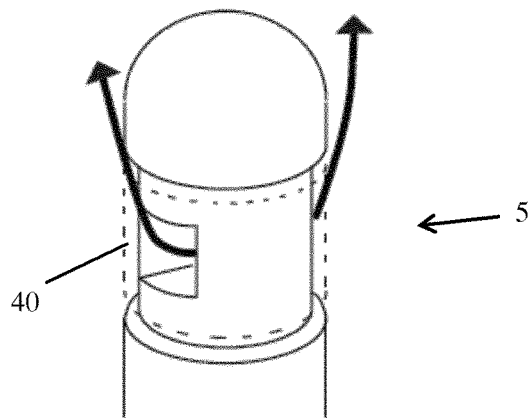
FIG. 7 is an enlarged view of a valve at the inlet port.
Figure 8:
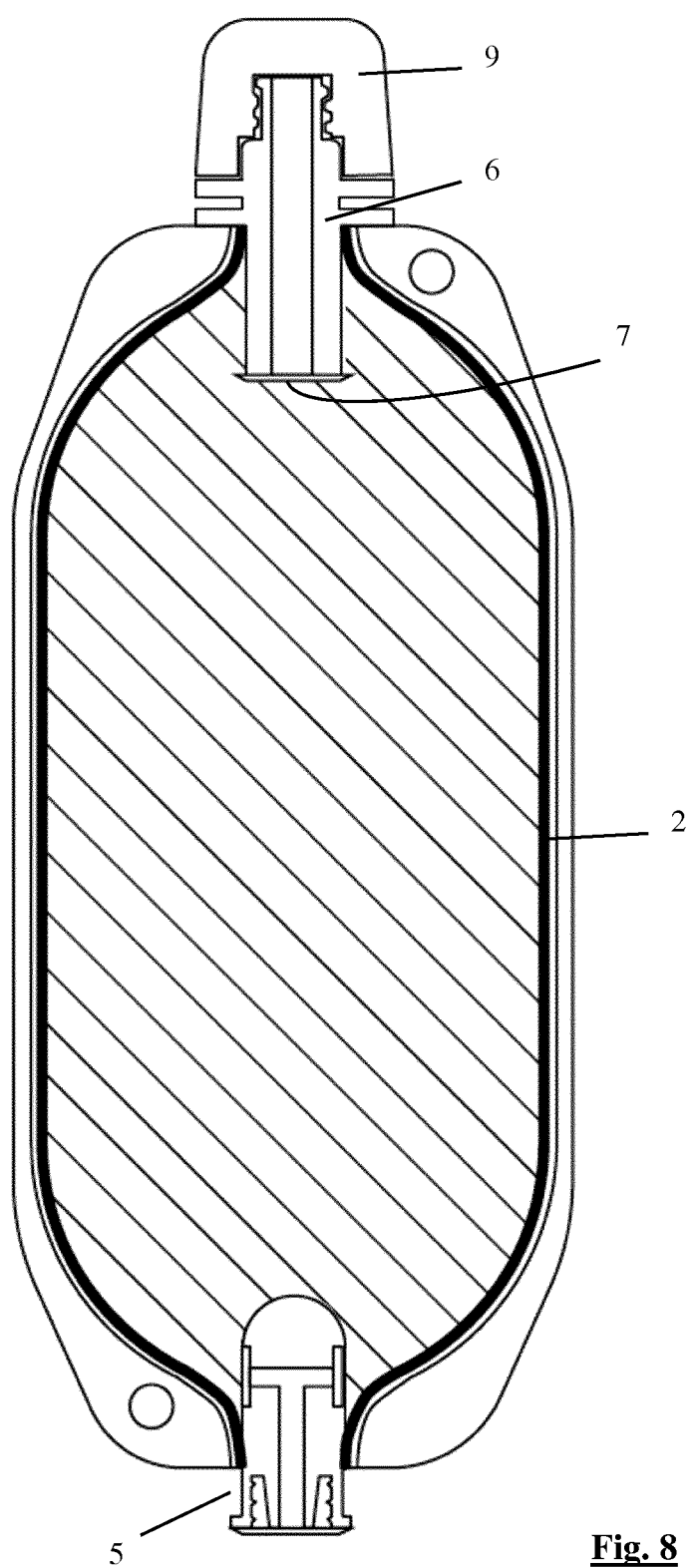
FIG. 8 is a cross sectional view of a filled pouch surrounded by a barrier.
Figure 9:
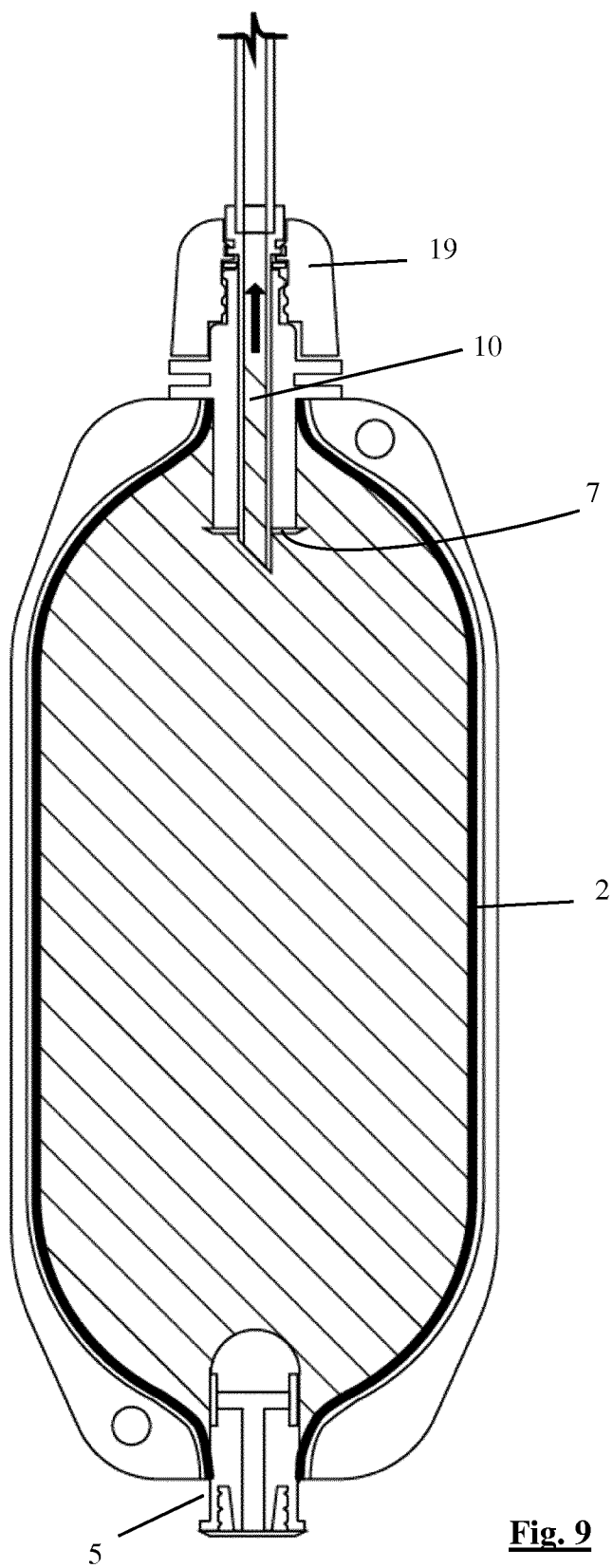
FIG. 9 is a cross sectional view illustrating the puncturing of a seal of the delivery port.
Figure 10:
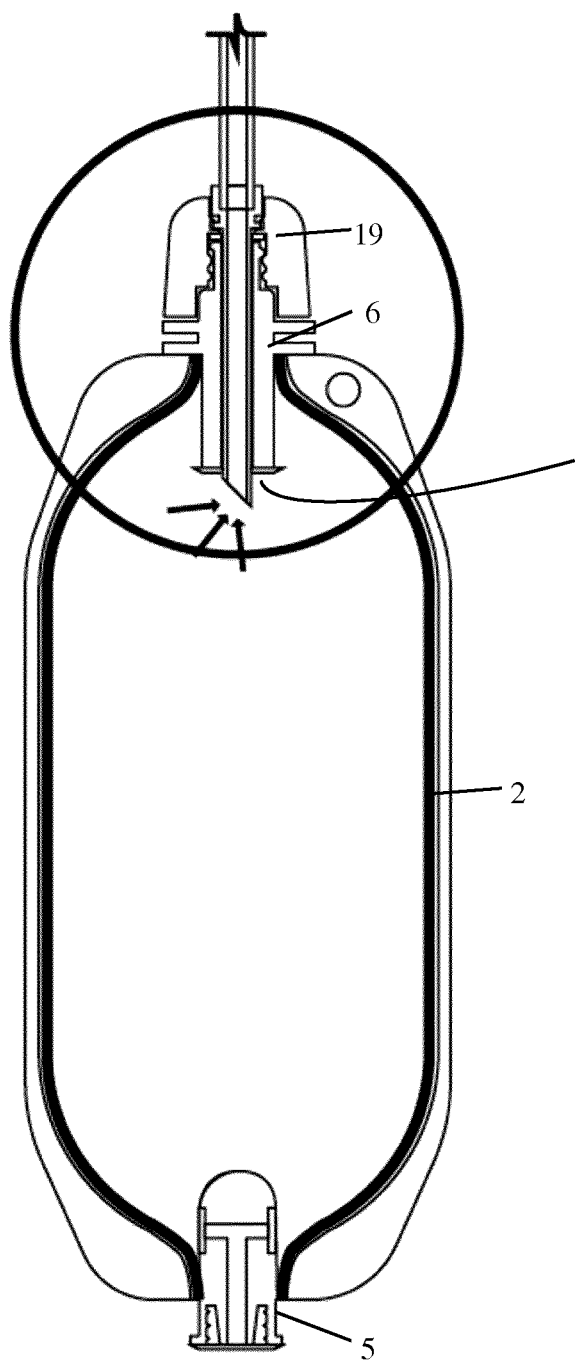
FIGS. 10 and 11(a) to 11(c) are views illustrating puncturing of the seal.
Figure 11A:
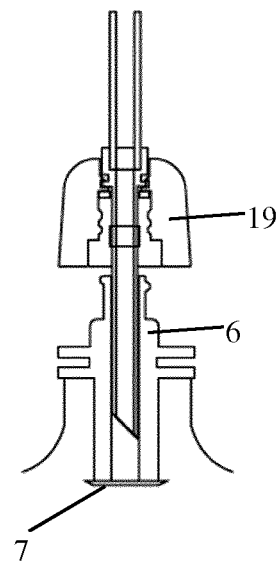
Figure 11B:
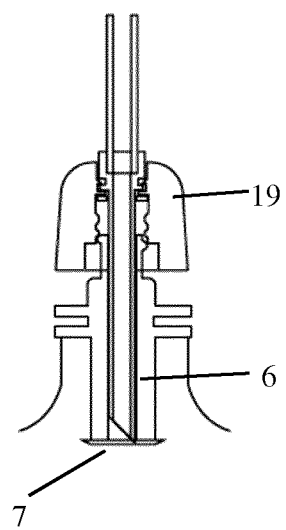
Figure 11C:
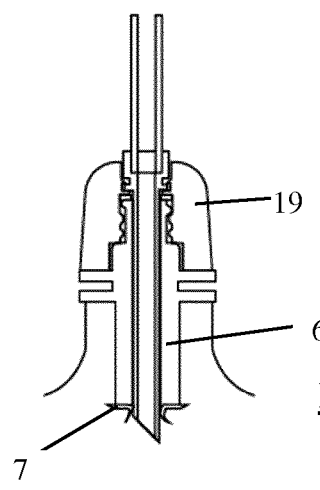

FIG. 7 shows a non-return valve/seal 40 at the inlet port 5.

FIGS. 8 to 11 illustrate various steps in inserting a feeding tube through the seal of the outlet port. The point of the piercing cap 19 is engineered to pierce the seal 7 on its last half revolution when the threads are intact as best seen in FIG. 11(c). The cap may include a compression seal/washer.

FIGS. 12 to 14 illustrate the gradual collapse of the pouch 2 as enteral fluid passes out through the outlet port caused by the expansile force of the pouch. It will be noted that as the pouch 2 collapses, the barrier 3 also collapses but to a much lesser degree than the collapse of the pouch. In this way a space is defined between the outer wall of the collapsing pouch and the inner wall of the partially collapsing barrier.

Figure 15:
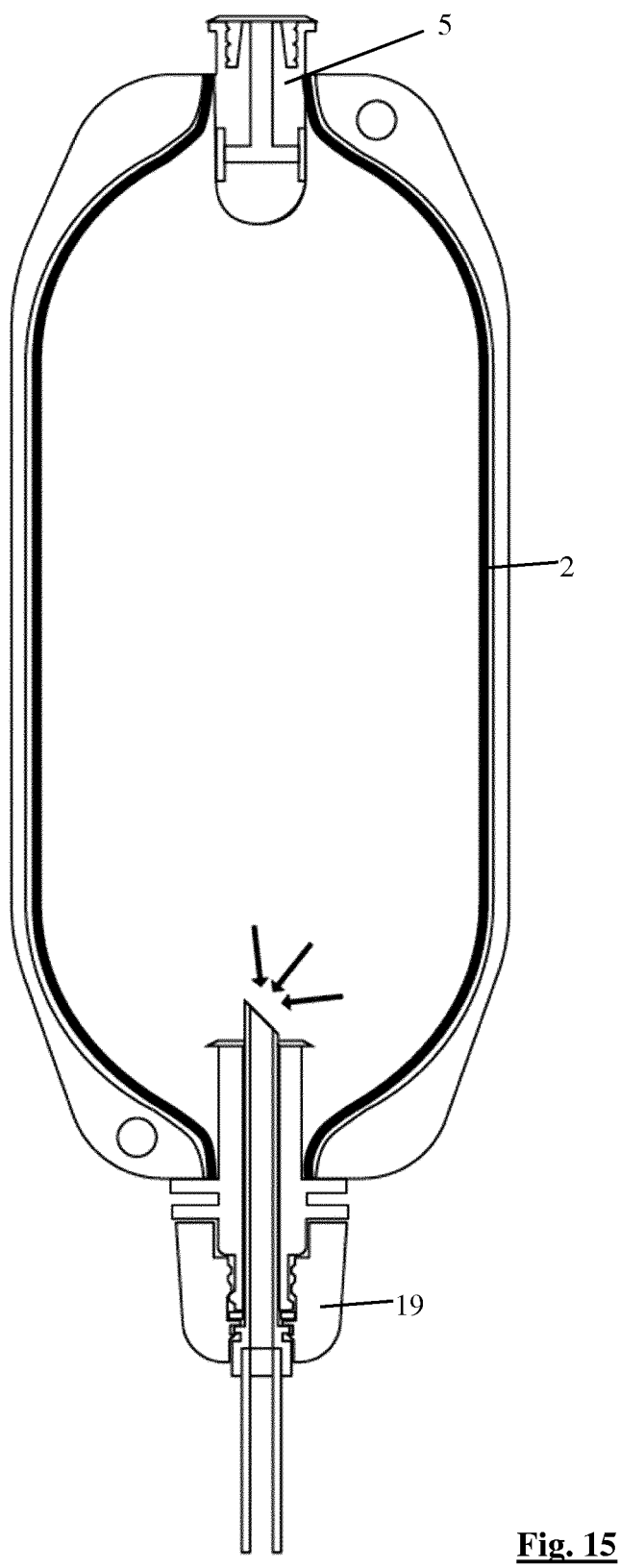
FIG. 15 illustrates the apparatus in a delivery configuration in another orientation.

Enteral fluid is delivered from the pouch by the expansile force of the pouch regardless of the orientation of the pouch. Gravity is not required. A different orientation of the pouch is illustrated in FIG. 15 by way of example.

Figure 16:
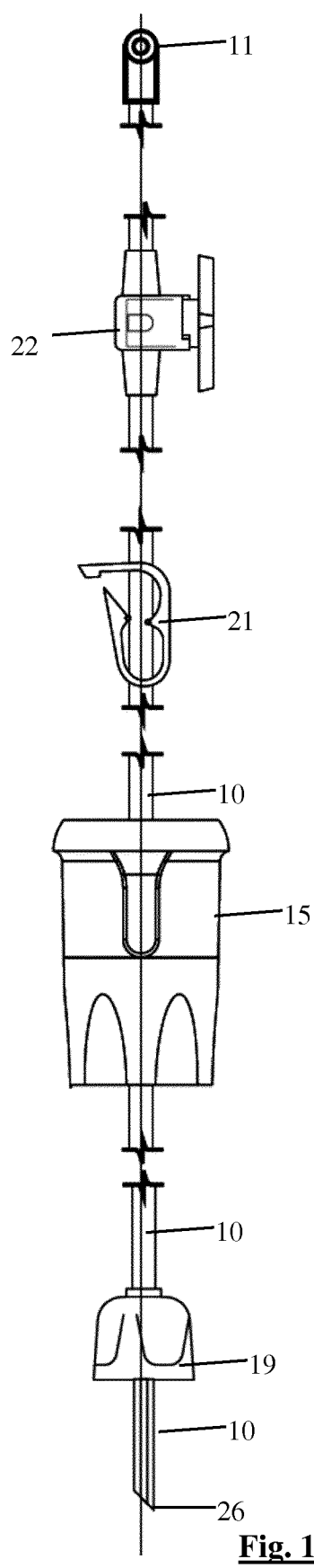
FIGS. 16 and 17 are exploded views illustrating the connection of the apparatus to a PEG feeding set.
Figure 17:
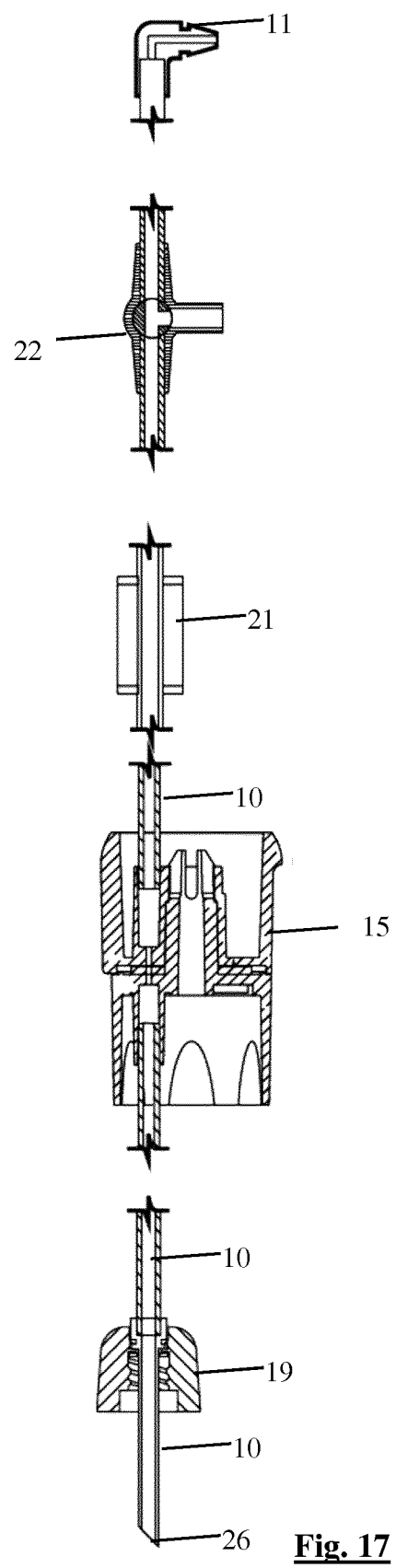
Figure 18:
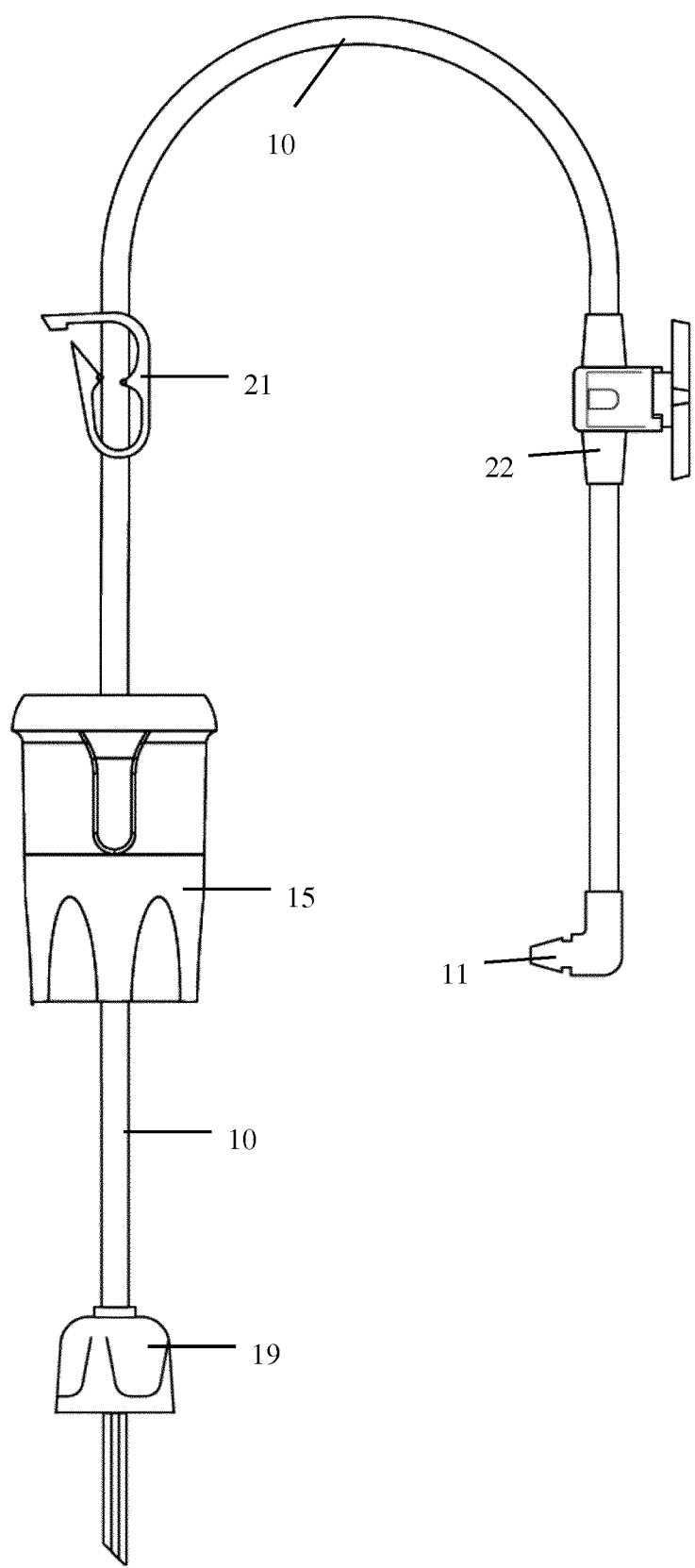
FIG. 18 is a view of the feeding set of FIGS. 16 and 17 assembled.

An enteral feeding set for use with the pouch of the invention is illustrated in FIGS. 16 to 18. The feeding set comprises a tube 10 having a connector 11 at one end for connection to a PEG inlet 12. The tube 10 extends through a cap 19 at the opposite end and terminates in a pointed end 26 which is used to pierce the seal 7 at the pod inlet 6. The flow of enteral feed through the tube 10 may be regulated using an in-line regulator 15. The tube set also includes a control tap 22 and a pinch tube stopper 21.

The enteral feeding apparatus may be used in a sequence which is illustrated in FIGS. 19 to 29.

Figure 19:
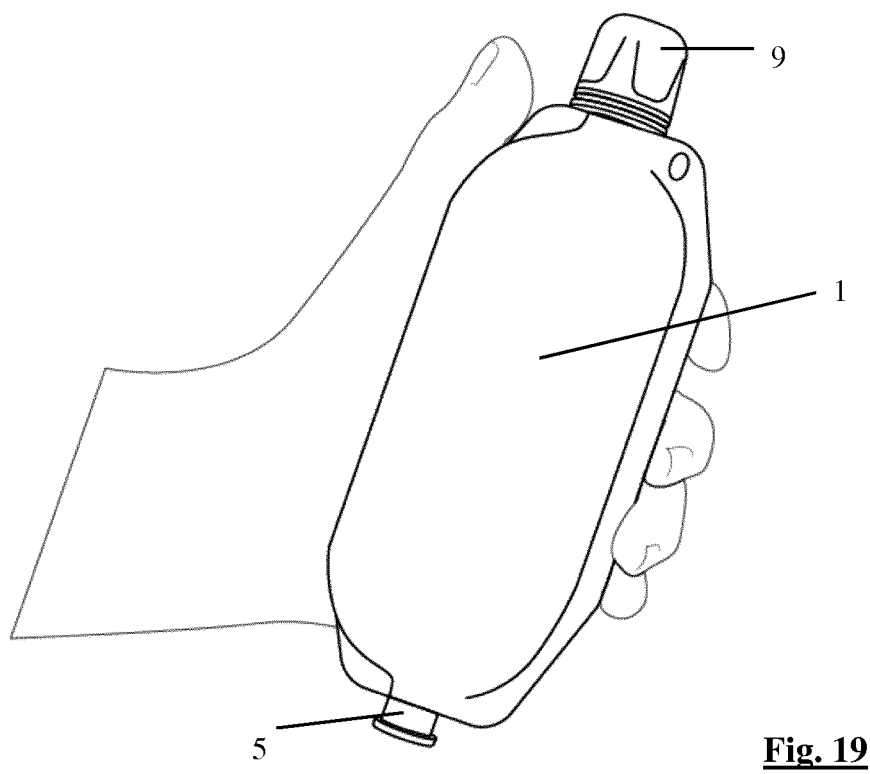
FIGS. 19 to 29 illustrate various steps in use of the enteral feeding apparatus.
Figure 20:
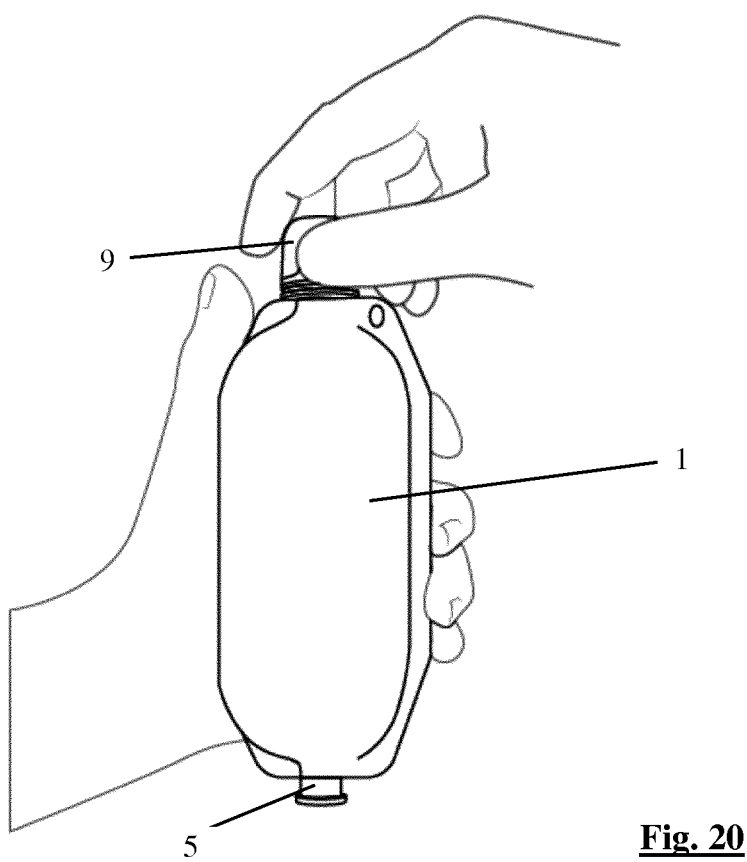
Figure 21:
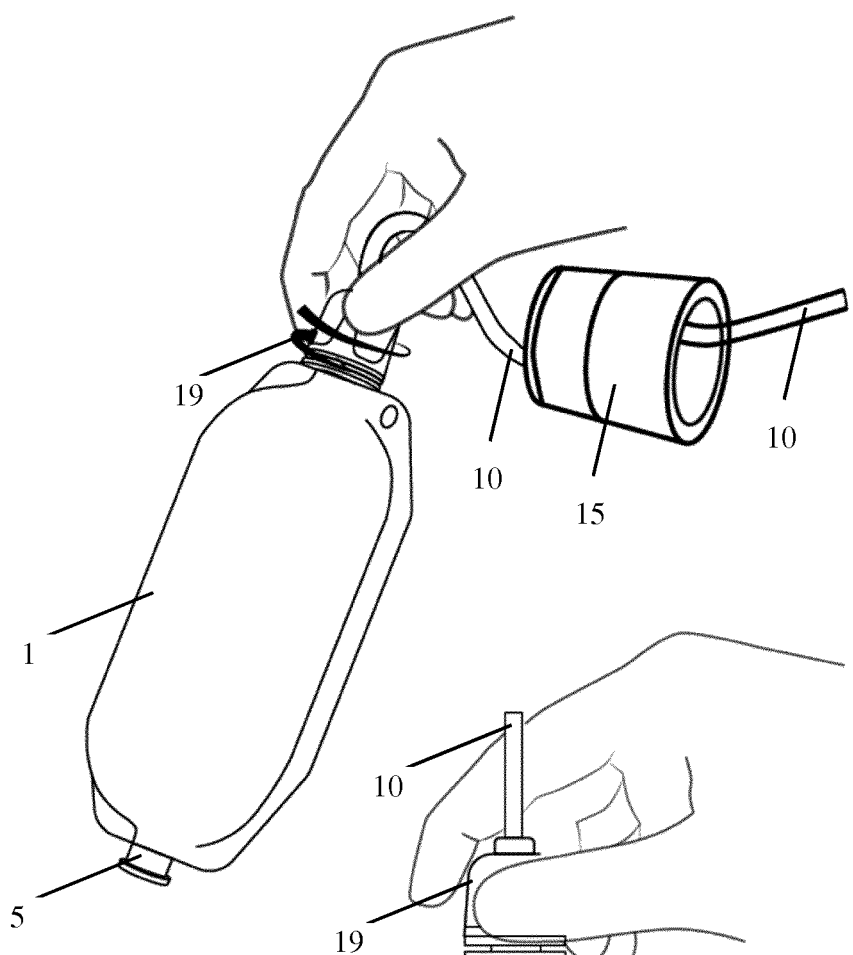

FIG. 19 shows a filled pod 1 ready for use. The user first removes the cap 9 from the outlet port (FIG. 20) and attaches the enteral feeding set (FIG. 21). Final rotation of the tube cap 19 causes seal 17 at the outlet port to be pierced.

Figure 22:
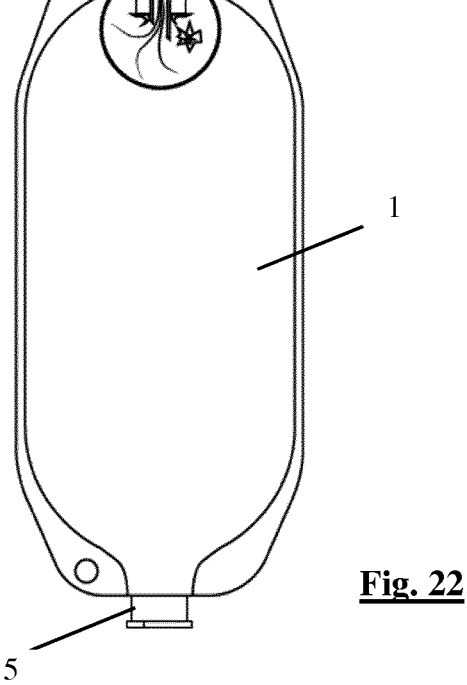

FIG. 22 illustrates the start of release of enteral fluid from the pod when the foil seal 7 has been pierced.

Figure 23:
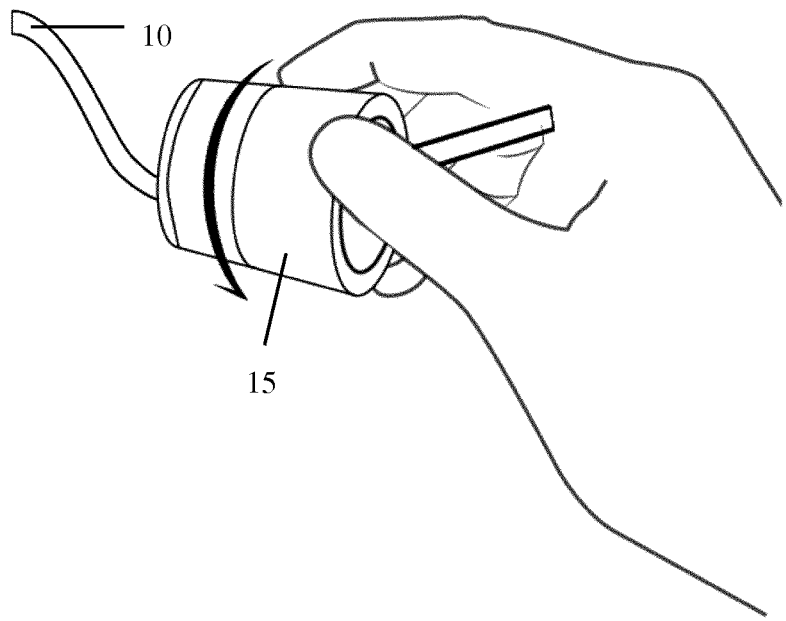

FIG. 23 shows the user twisting the regulator 15 to the prime function after the feeding tube set has been connected to the ENFit connection.

Figure 24:
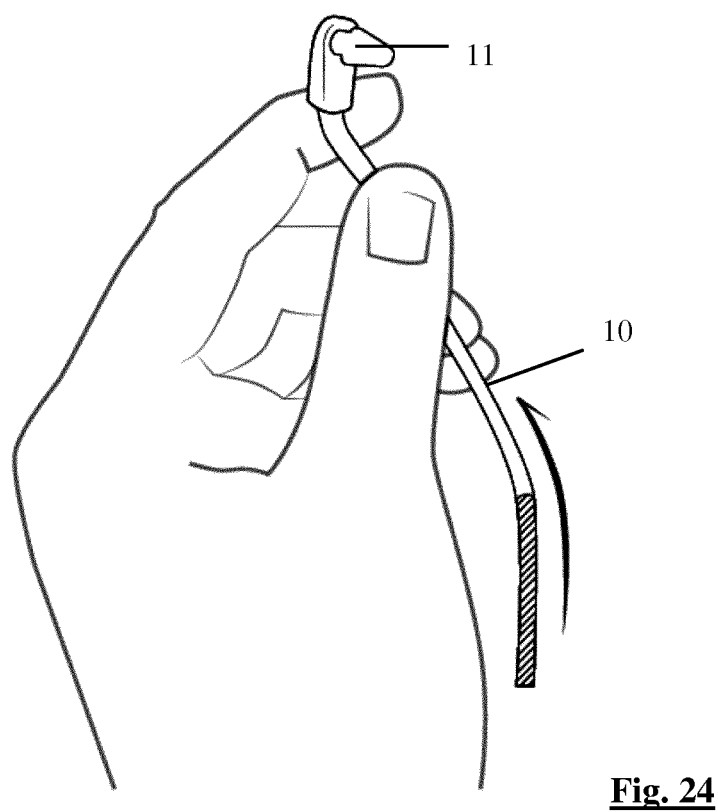

FIG. 24 shows the feed moving at a fast pace through the tubing 10 to the PEG connection 11 at the end of the feeding tube set. The user can visually inspect the movement of feed through the tube 10 and when near the PEG connection 11 the system is primed for feeding.

Figure 25:
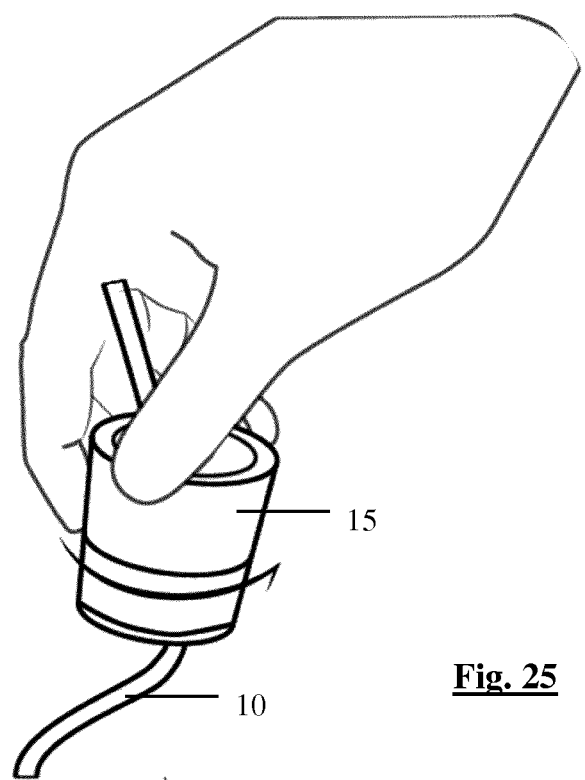

FIG. 25 shows the user turning the regulator 15 to select the desired flow rate, typically, between 50 ml to 250 ml per hour.

Figure 26:
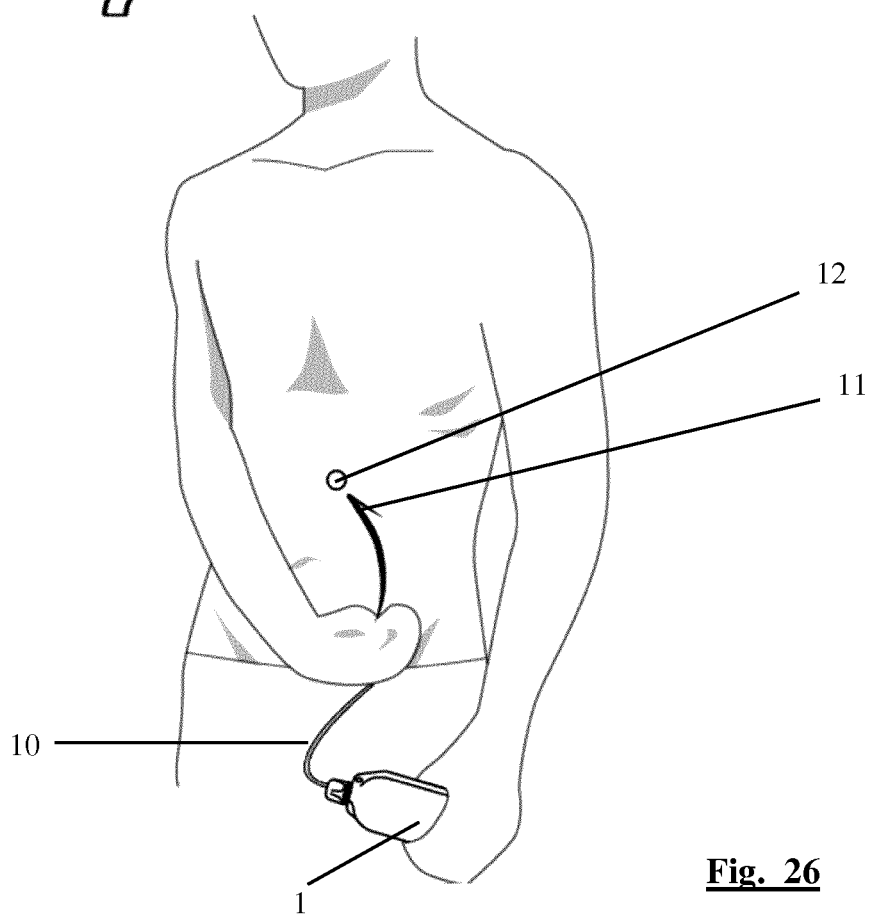

FIG. 26 shows the PEG connection/food pod being connected to the PEG implant. The food pod 1 is pumping feed directly into the stomach and is active. The food pod 1 can then be concealed or placed in a desired location.

Figure 27:
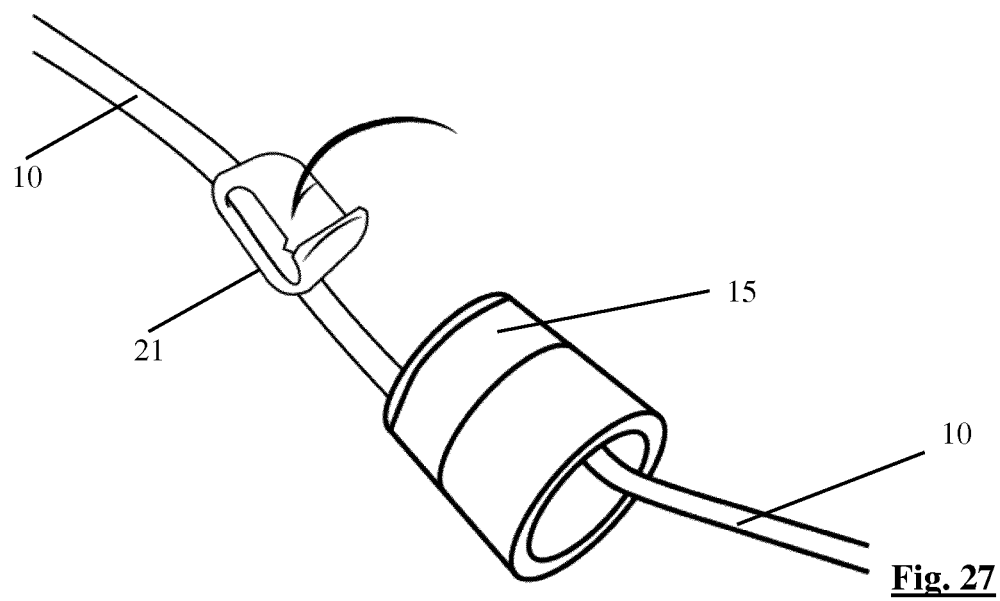

FIG. 27 shows a pinch tube stopper 21 that may be used to stop flow going through the tube 10. When the food pod has finished and is empty the stopper 21 is activated to prevent spillage from the PEG site. The image also shows, when fully primed during the priming stages, the food pod flow can be stopped with a stopper 21 that stops all enteral fluids from passing further through the tubing.

Figure 28:
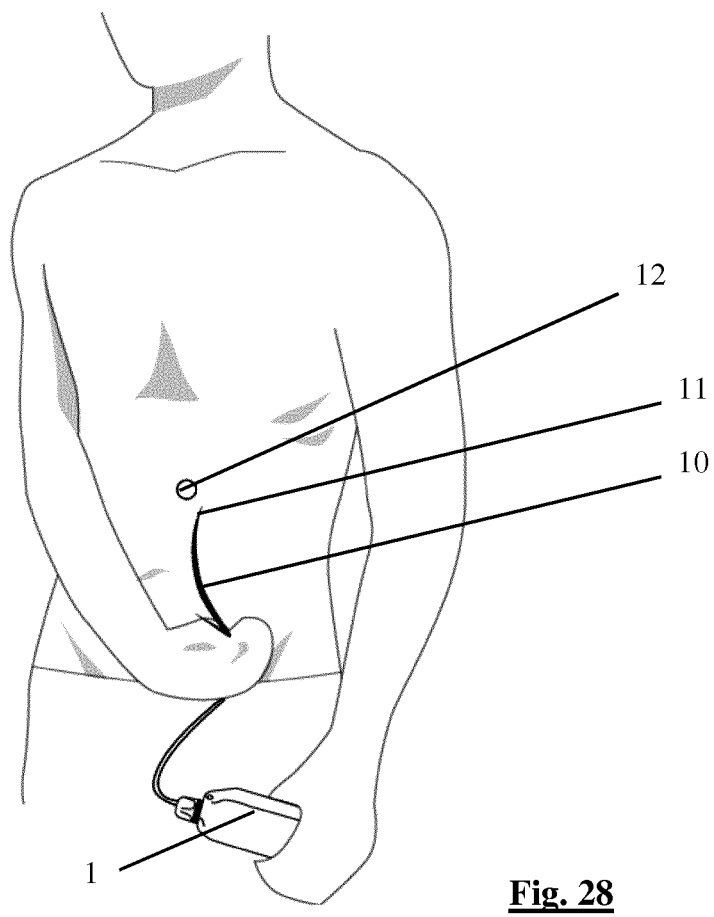

FIG. 28 shows the user disconnecting the food pod 1 from the PEG site. The user can disconnect the feeding tube set as the same feed set can be used within 24 hours (e.g. if a user uses three 500 ml food pods in a day it can be reused for each one). The feed set may be cleaned and flushed by connecting a syringe to the same ENFit connection that is connected to the food pod.

Figure 29:
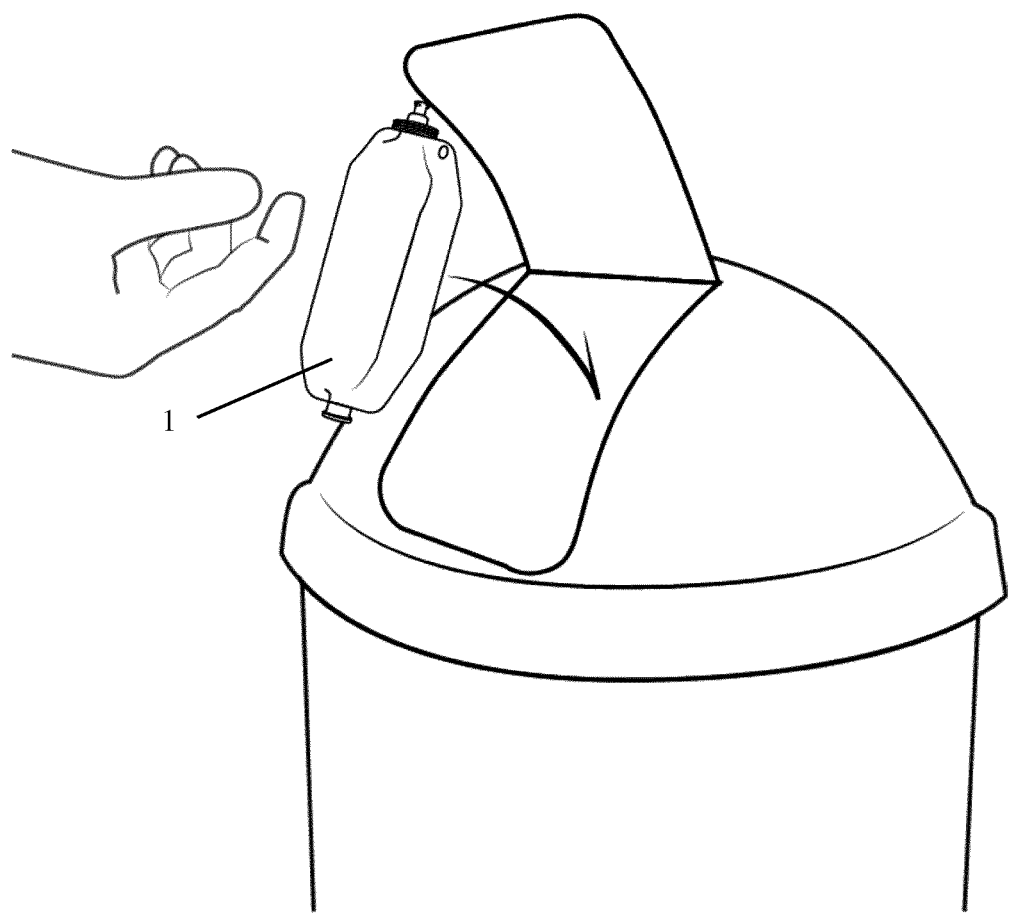

When finished, the food pod 1 may be disposed of as shown in FIG. 29.

The enteral feeding apparatus of the invention is small and tidy and offers the patient a much easier and faster setup, and less restriction when undertaking simple everyday jobs. The apparatus is light in weight and is easy for a user to carry around during the day. At night the apparatus has zero noise or vibrations leading to a better night's sleep.

The pouch is used to store the enteral fluid and apply pressure for delivery of enteral fluid from the device. The material of the pouch can be natural and/or synthetic (e.g. silicon, latex, polyurethane and isoprene rubber). The type of elastomer, number of elastomeric layers and the geometry of the reservoir pouch may be selected to regulate the pressure produced on the fluid in the manner of a stretched balloon.

Figure 30:
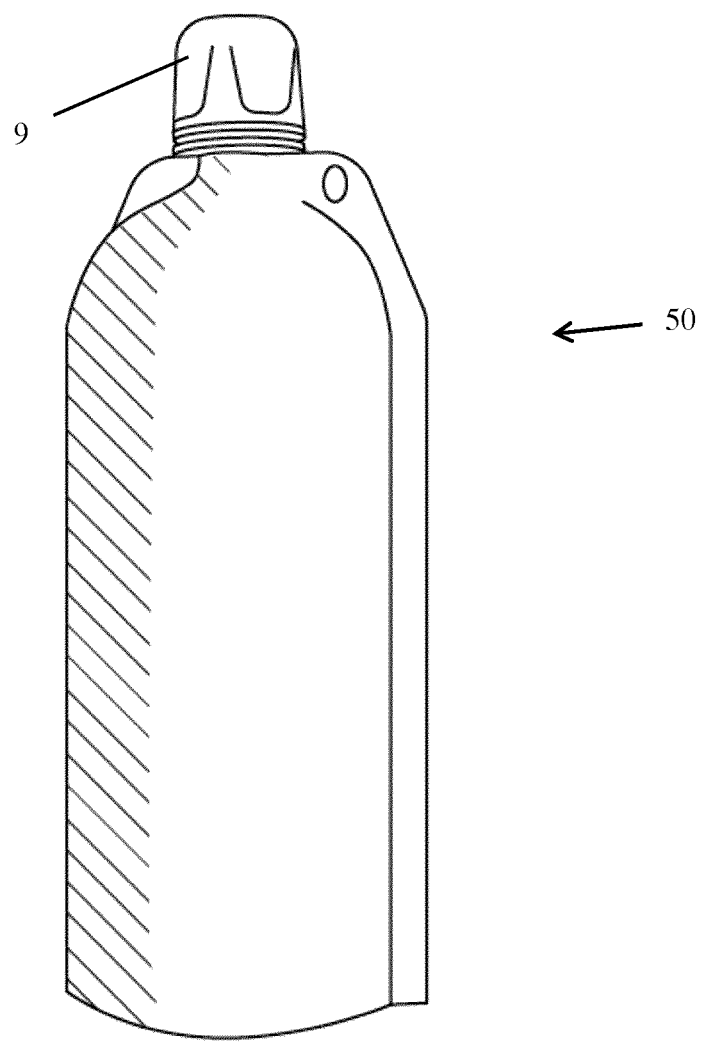

Referring to FIGS. 30 to 32 there is illustrates another enteral feeding pod 50 according to the invention. The pod 50 is similar to that described above and like parts are assigned the same reference numerals. In this case the pod 50 is free-standing. The pod has peripheral walls 51 that extend downwardly from the main body. The walls 51 terminate in a common base plane. The region bonded by the walls 51 in this case also accommodates the inlet port cap 20.

The additional advantage of this arrangement is that the pod can be readily mounted on any flat surface with enhanced flexibility for the user.

Figure 33:
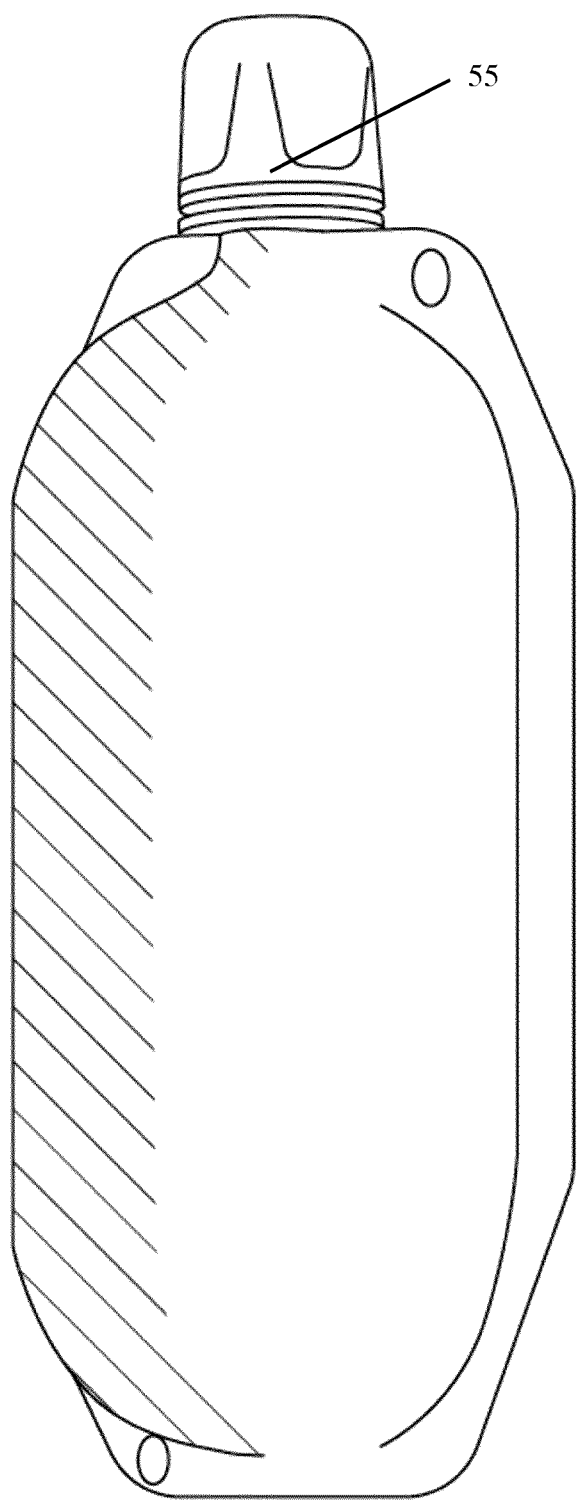
FIG. 33 illustrates another food pod according to the invention.

Referring to FIG. 33 there is illustrated another food pod according to the invention. The pod is similar to that described above except that in this case there is a common inlet/outlet 55 through which feed is introduced into and delivered from the pod.

Figures 34, 35:
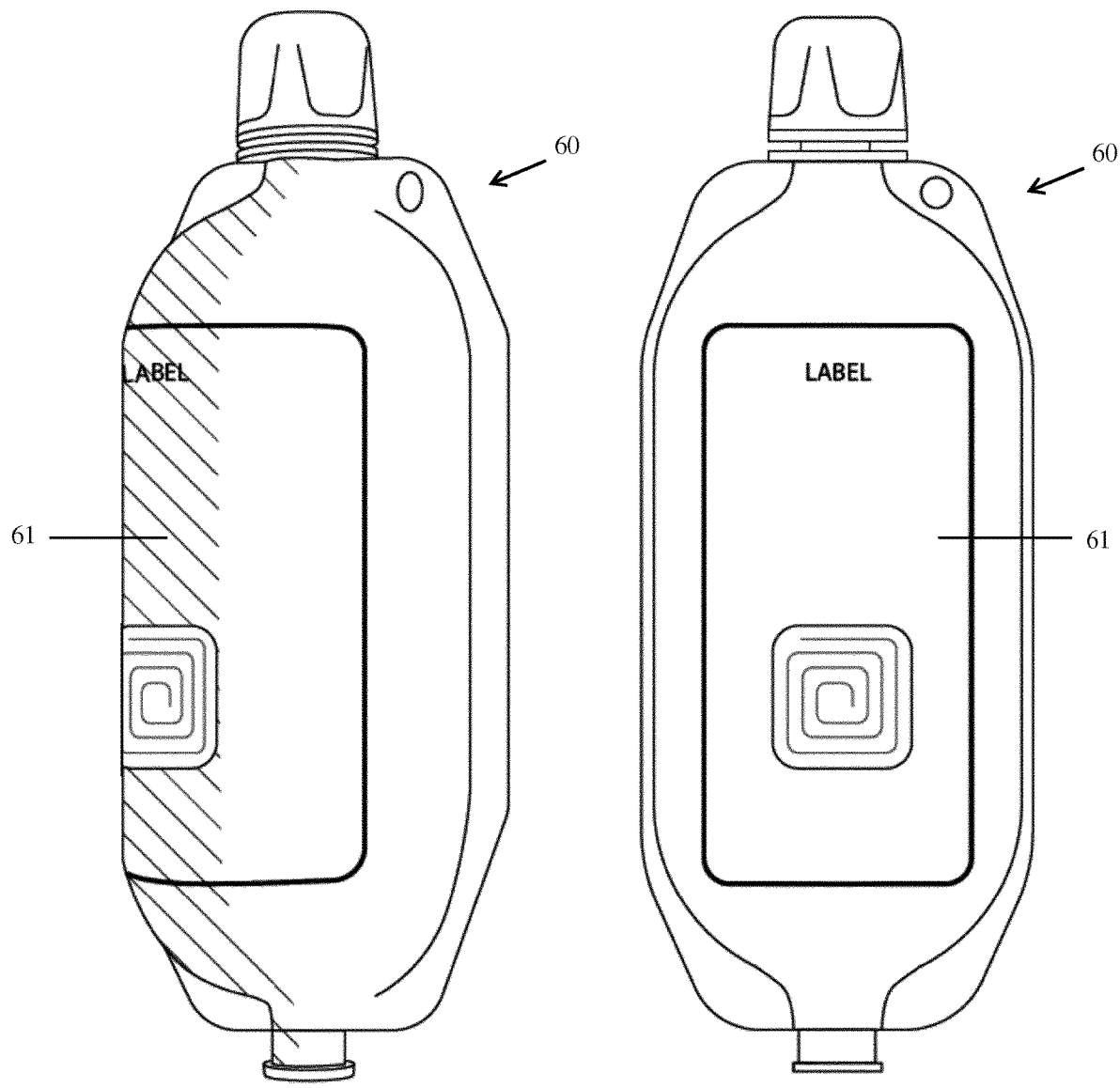
FIGS. 34 and 35 show a further enteral feeding apparatus with near field communication tags on the labelling.

FIGS. 34 and 35 show another enteral feeding pod 60 which includes a label 61 which include but not limited to a Near Field Communication tag 120 that allows to transmit small amounts of data through a distance of in some cases about 4 cm. Other suitable systems include RFID.

Figure 36:
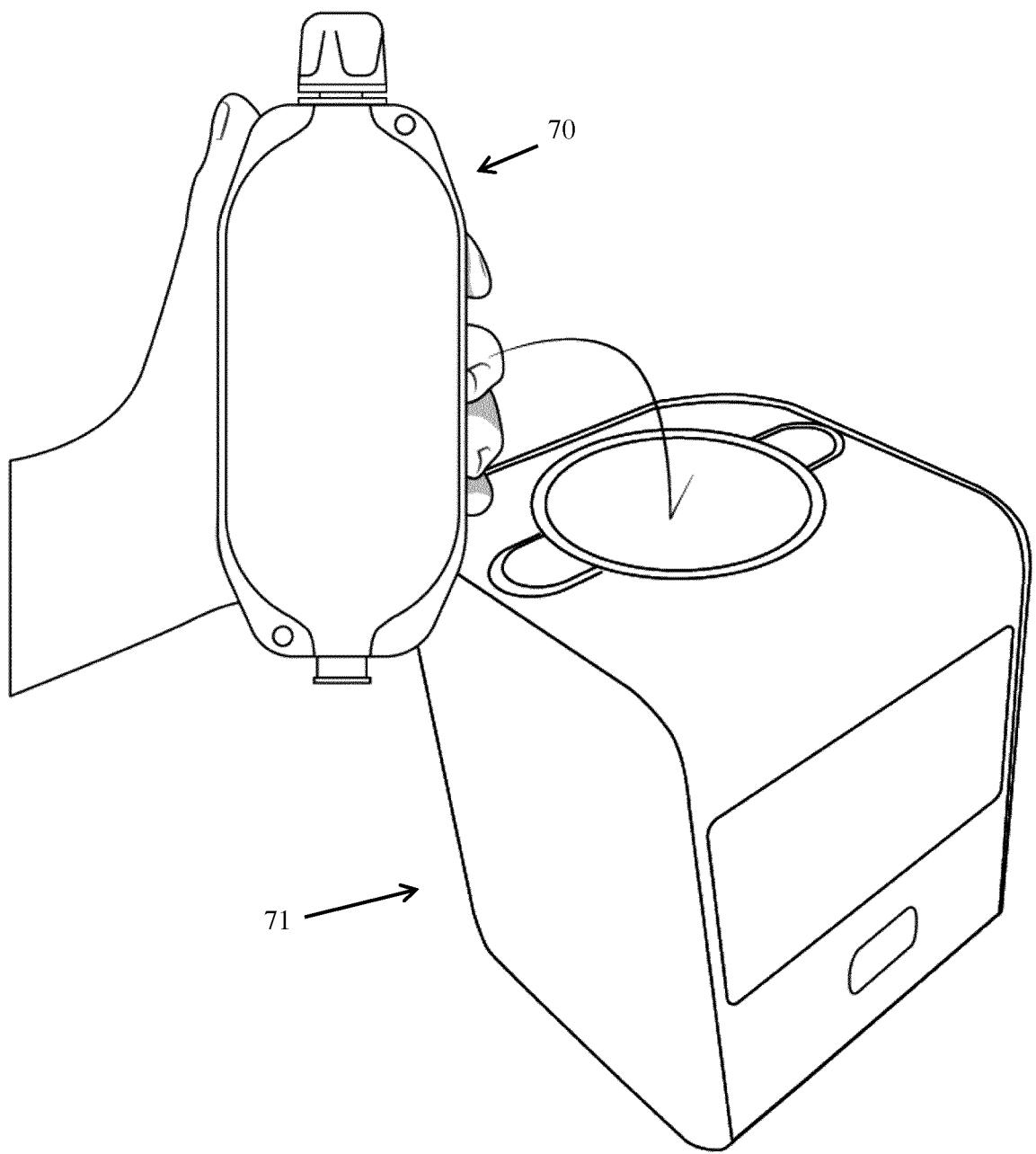
FIG. 36 illustrates a food pod of the invention being mounted to a docking station.
Figures 37, 38:
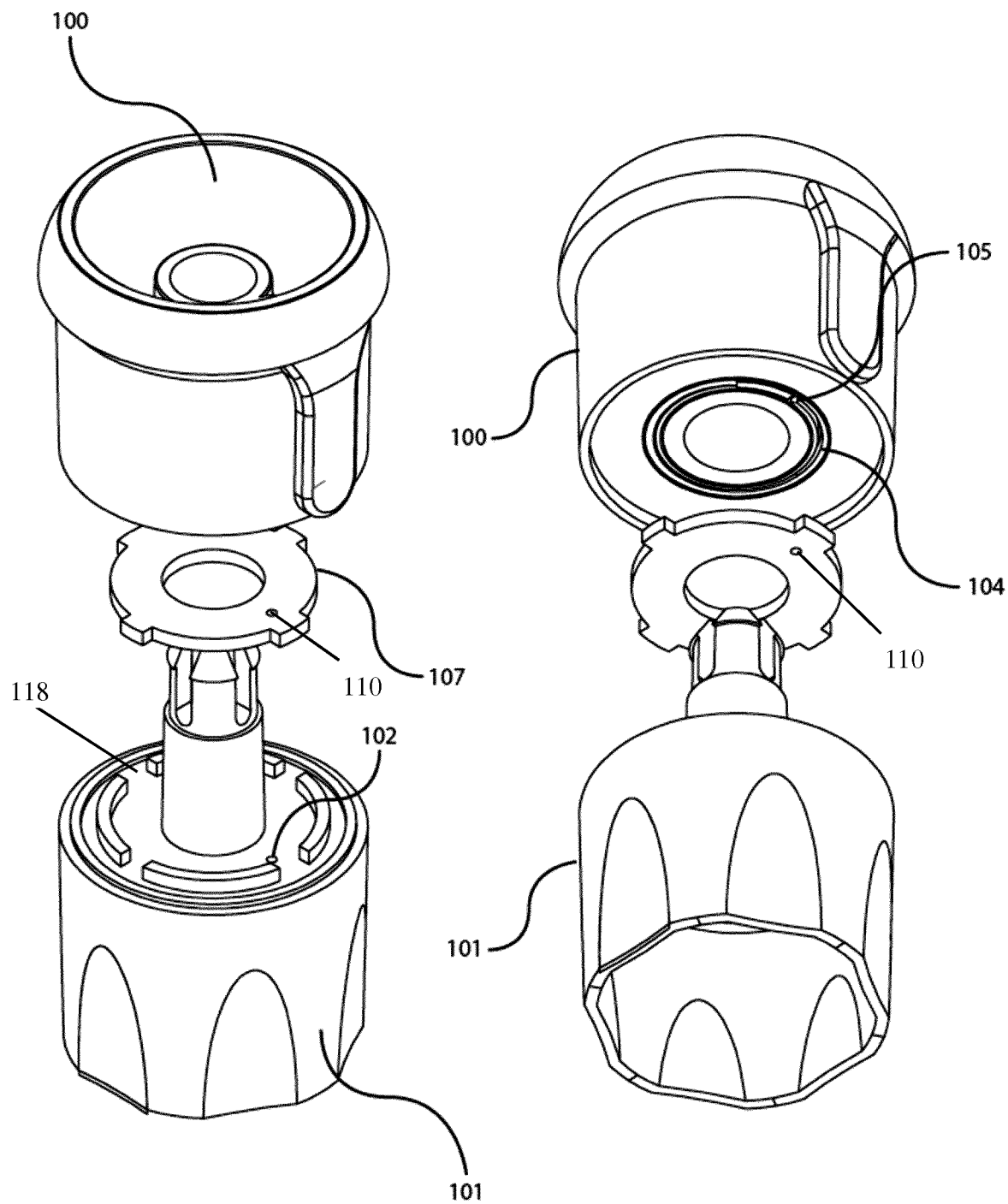
Figure 39:
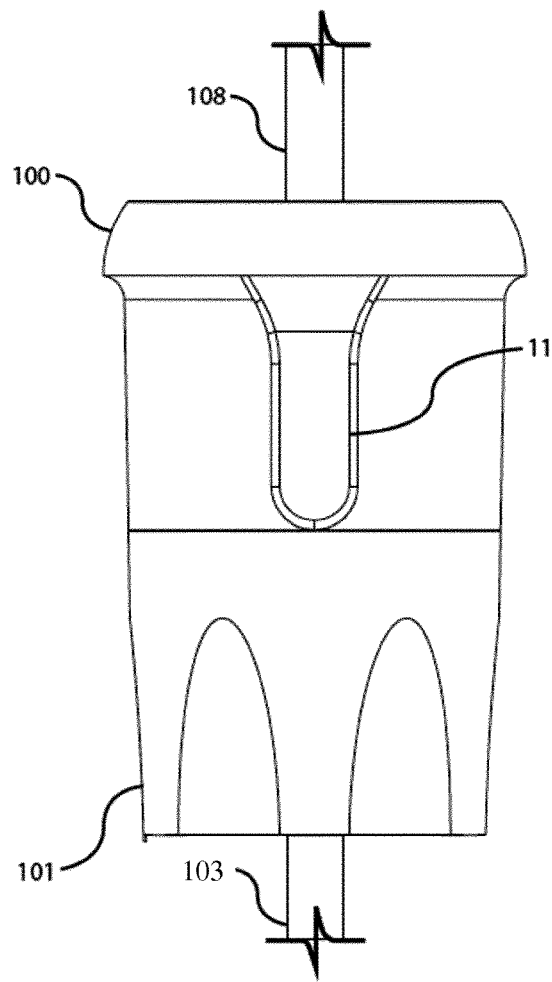

FIG. 36 shows an enteral feeding pod 70 being mounted to a docking station 71. The docking station 71 is used for monitoring feed rates at static locations such as bedside and chairside. The docking station 71 provides feedback and alarms to users and carers via interface, cloud and/or networks.

FIGS. 37 to 44 illustrate a regulator which may be used in the enteral feeding system of the invention.

The regulator 15 comprises a top fitting 100, a bottom fitting 101, a central washer 107, inlet tubing 103 and outlet tubing 108. The top cap has a flow channel 104 extending within the body of the top fitting 100. There is an inlet bore 102 to allow enteral fluid to enter in between the top fitting 100, the bottom fitting 101 and allow passage through the washer 107 at a bore hole 110. The enteral fluid must pass through the regulator in the following order to facilitate flow regulation: inlet tubing 103, the inlet bore 102, the washer bore 110, the channel 104 the outlet bore 109 and the outlet tubing 108.

This restricting flow channel 104 is configured to restrict the flow of enteral fluid through the inlet bore 102 dependent on the degree of rotation of the top regulator cap 100 relative to the to the bottom cap. The restricting channel 104 extends less than 360° (for example 350° or 340°) around the inside of the regulator 15. In this way flow from the inlet bore 102 of the bottom cap 101 is fully blocked for at least one position of the regulator cap 100. In another position of the regulator cap (for example FIG. 44(*b*) 125°) the restricting channel 104 does not restrict full flow of enteral fluid from the inlet bore 102 of the bottom cap 101 to the outlet bore 105 in the body of the top cap 100.

Figure 40:
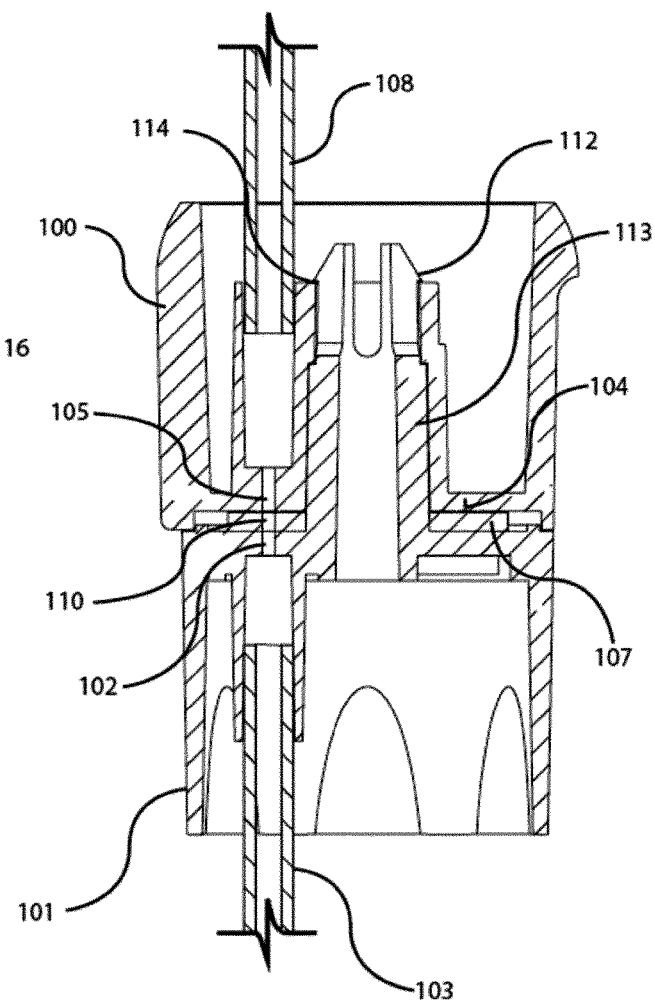
Figure 43:
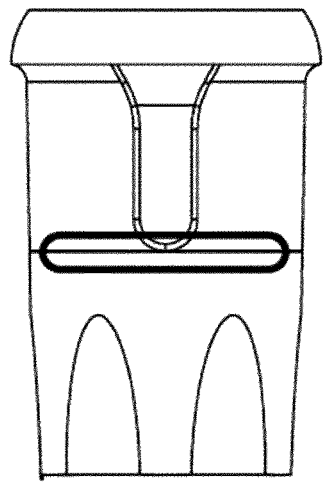

Referring in particular to FIG. 40 it will be noted that the bottom cap 101 has snap fit formations 112 on a central column 113 end which engage in complementary snap fit formations 114 on the inside of the top cap 110. The washer 107 is located between the end of the central column 113 and the top cap 100. The washer 107 has a flange part 115 that engages over the formations and into a corresponding groove 118 in the bottom fitting 101. On assembly, an inlet bore 102 from the inlet tubing 103 is aligned with a washer bore 110 through the washer 107. When the regulator is at full flow the inlet bore 102 is in turn aligned with the outlet bore 105 to the outlet tubing 108 through the regulator cap.

The regulator top cap 100 is snap fitted to the bottom cap 101. This is illustrated at FIG. 40 which shows how the washer 107 is positioned from a plan view in FIG. 42(*b*). The nutritional feed flows from the reservoir 2 through the outlet port 6 to the inlet tubing 103 to the inlet bore 102. As the top cap 100 twists (FIGS. 23, 44(*a-d*)), this allows the flow to be activated. On the top cap 100 there is an outlet bore 105 which defines the channel 104 that runs around the inner face of the top cap 100. This channel 104 allows the nutritional feed to flow depending on the degree to which the top cap 100 is turned and how wide the slot 104 is at a particular position of the cap. The nutritional feed then proceeds to the outlet tubing through 105 and then to the exit 11 (FIG. 24).

Figures 44A, 44B:
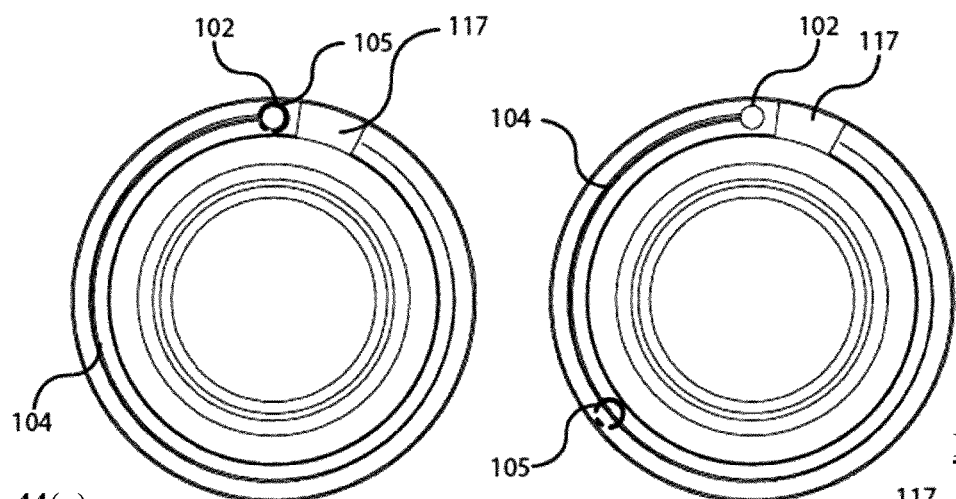
Figures 44C, 44D:
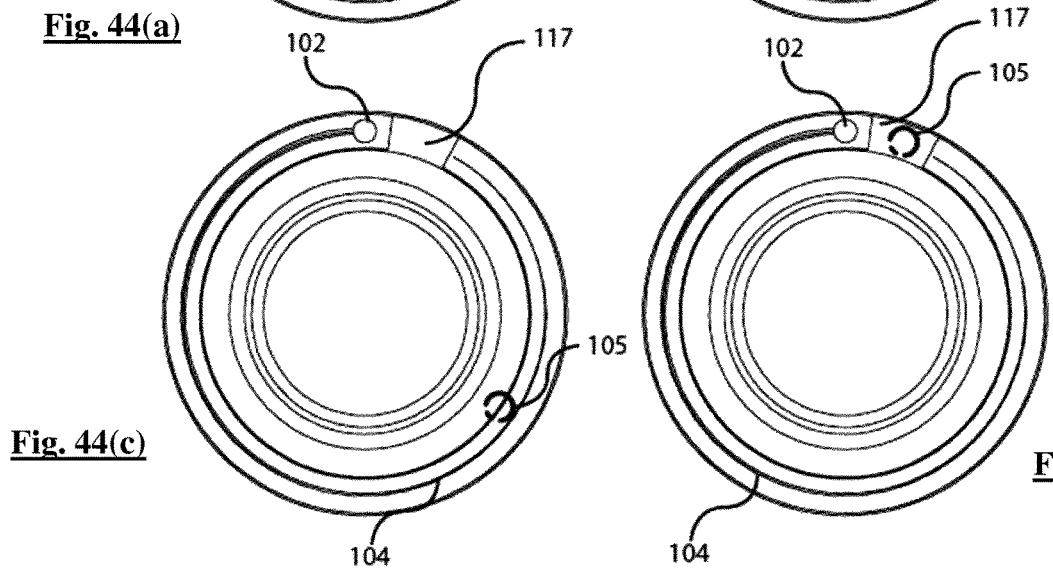

FIG. 44(*c*) shows the regulator turned on to 33% which allows a limited amount of feed to flow. The fluid passes through the washer bore 110 and then is met by the narrowing channel 104. In FIG. 44(*c*) the nutritional feed will hit a narrow part of channel 104 and flow is restricted. In FIG. 44(*b*) fluid is regulated to 66% of fluid flow. The regulator cap has been rotated further so the fluid that has passed through seal channel 102 has now hit a wider point compared to FIG. 44(*c*) in the narrowing channel 104. FIG. 44(*a*) shows the regulator fully open and the bores 102 and 105 are aligned providing an unobstructed passage through the regulator 15. In this position there is no restriction on the pressure of the fluid so the fluid will then be at 100% flow rate.

FIG. 44(*d*) shows the regulator in a closed position (with no fluid exiting the device). This is due to a block at 117 (because channel 104 only extends around less than 360°) that does not allow any fluid to pass through. FIG. 44(*c*) shows the regulator in a position 33% opened. The blocker at 117 stops the flow from taking the shorter route to 105 so it follows the slot 104 the longer way around to 105. The channel 104 dimensions widen as it goes around anti-clockwise. FIG. 44(*b*) shows the regulator in a position 66% opened. The slot 104 is now at a wider opening compared to FIG. 44(*c*) this allows a higher rate of flow to pass through it. The fluid still flows in an anti-clockwise motion from 102 to 105.

FIG. 44(*a*) shows the regulator cap fully opened (100%). In this position all of the openings 102 and 105 align.

The regulator may have a lock feature so that when the prime position has been passed it cannot be twisted back to freeflow. When changing flow rate the regulator may have a haptic feedback making it stiff to change flow rate to stop accidental flow changes.

Figure 45:
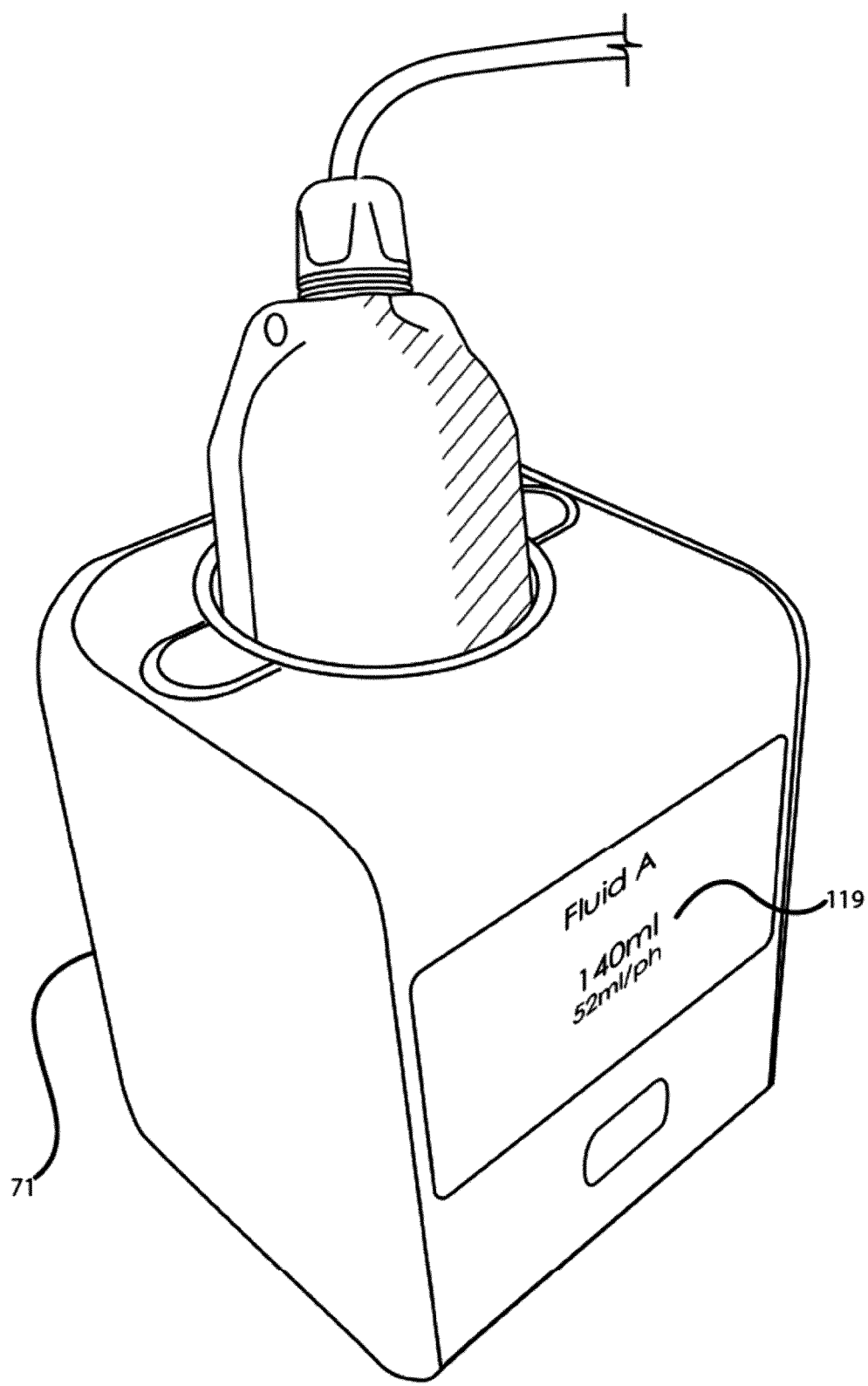
FIG. 45 is a view of a food pod and a docking station with a screen display.
Figure 46:
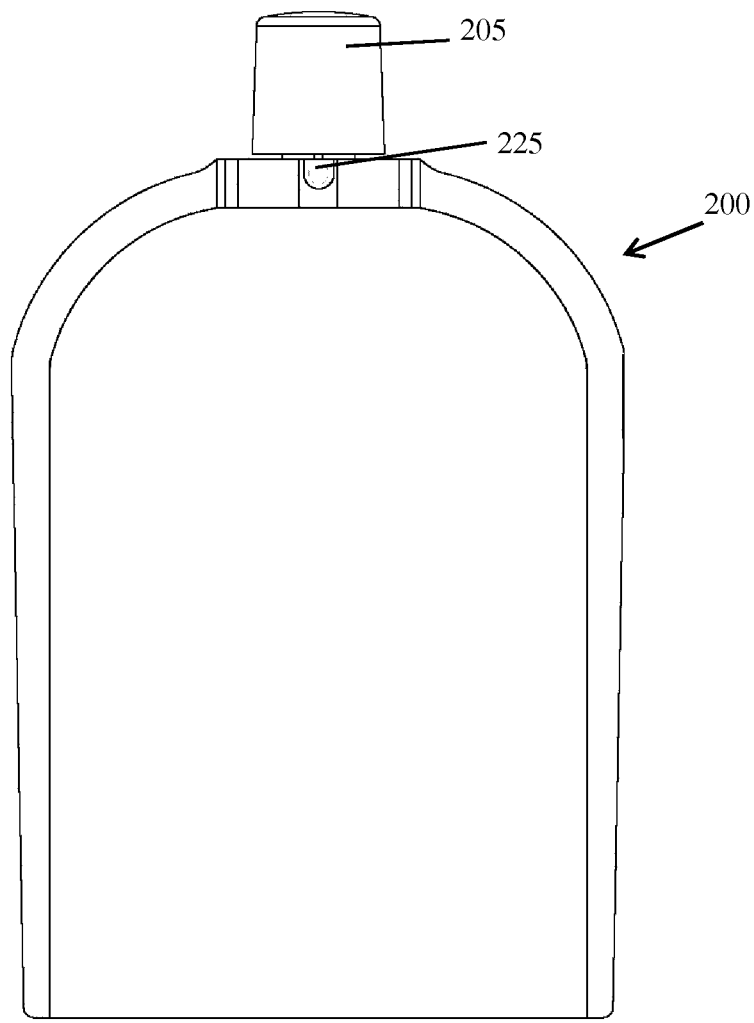
FIGS. 46 and 47 are views of enteral feeding pouch of the invention.
Figure 47:
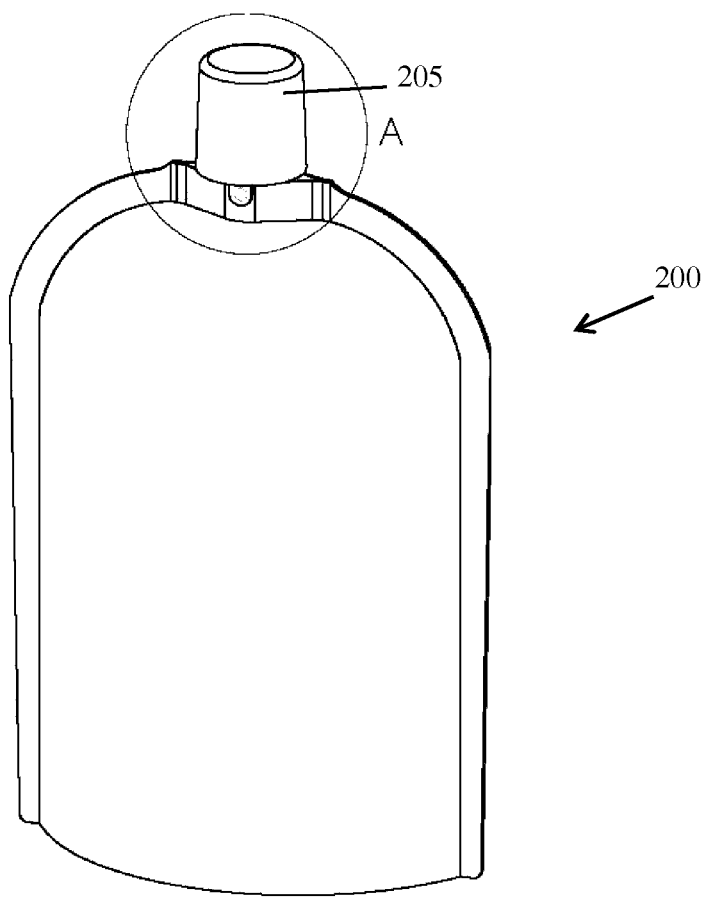
Figure 48:
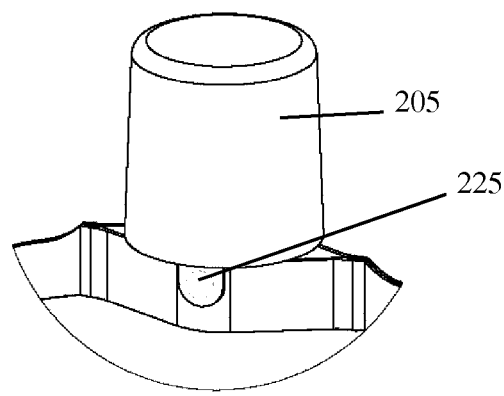
FIG. 48 is an enlarged view of detail A of FIG. 47.
Figure 49:
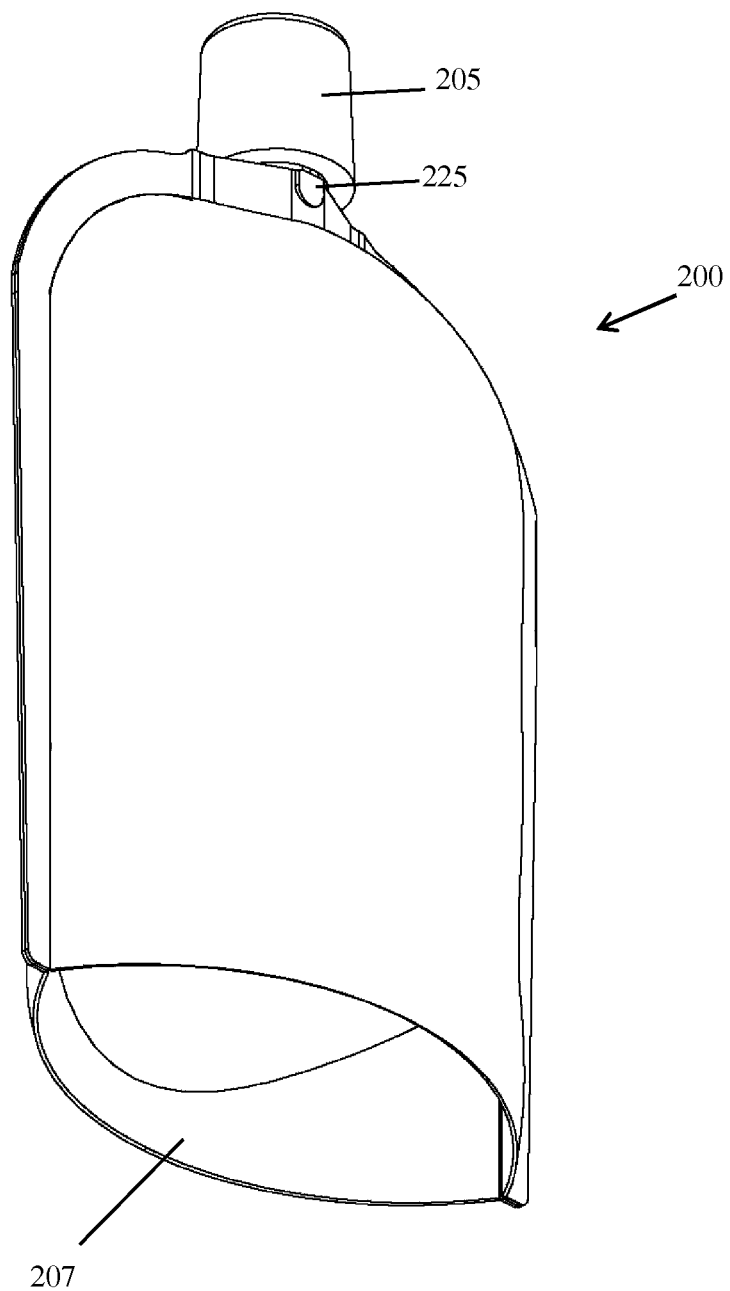
FIG. 49 is an isometric view of the pouch of FIGS. 46 and 47.
Figure 50:
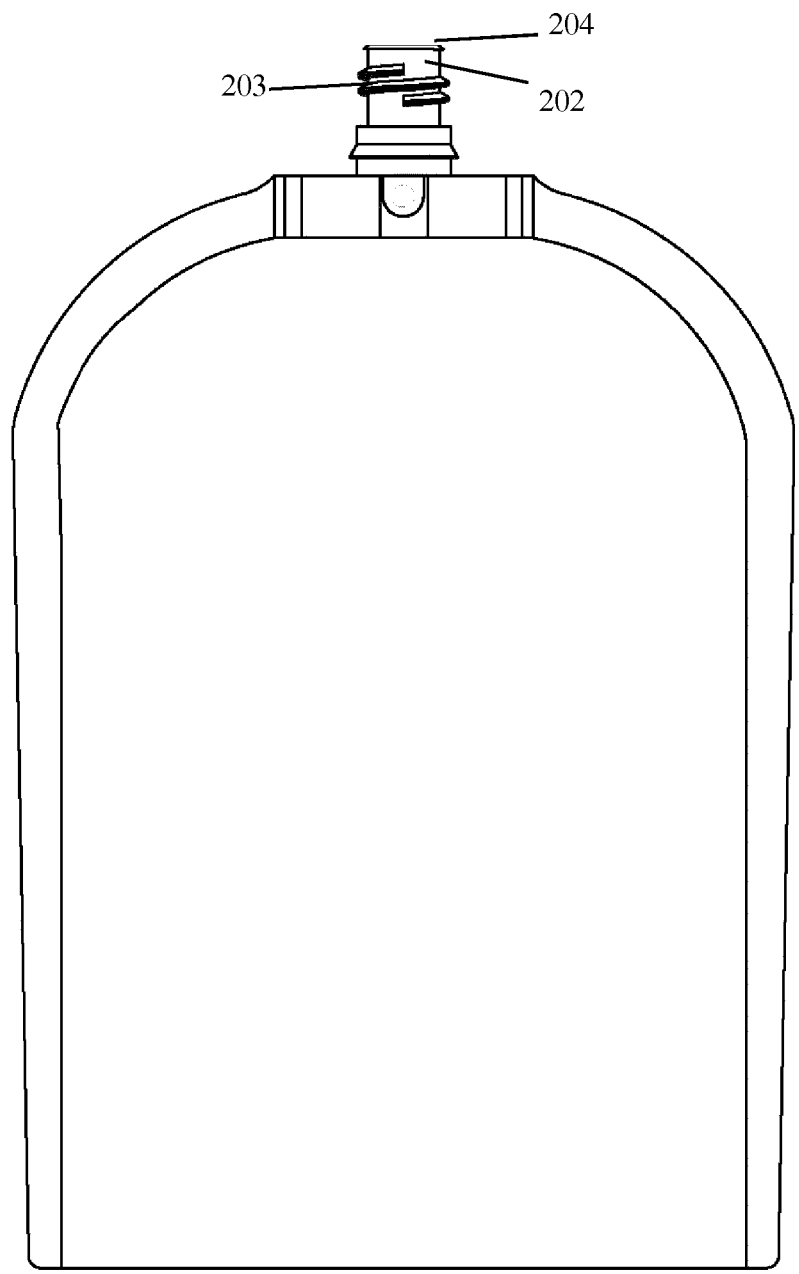
FIGS. 50 and 51 are views of the pouch of FIGS. 46 to 49 with a cap removed.
Figure 51:
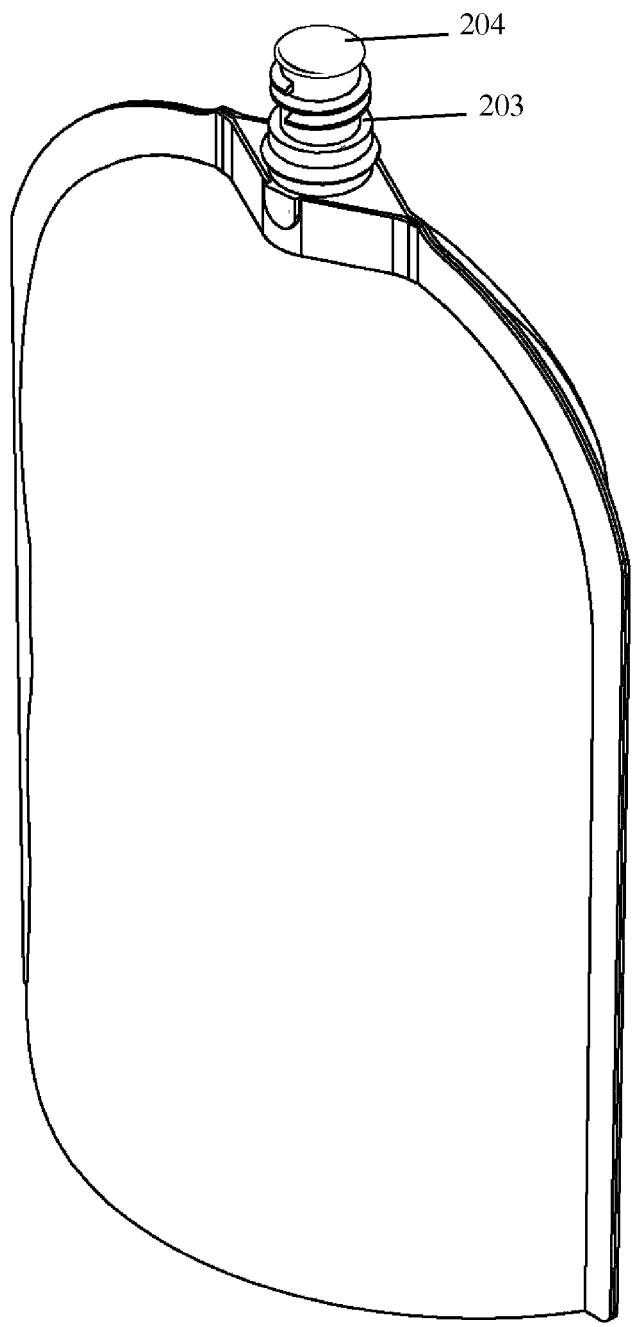
Figures 52, 53:
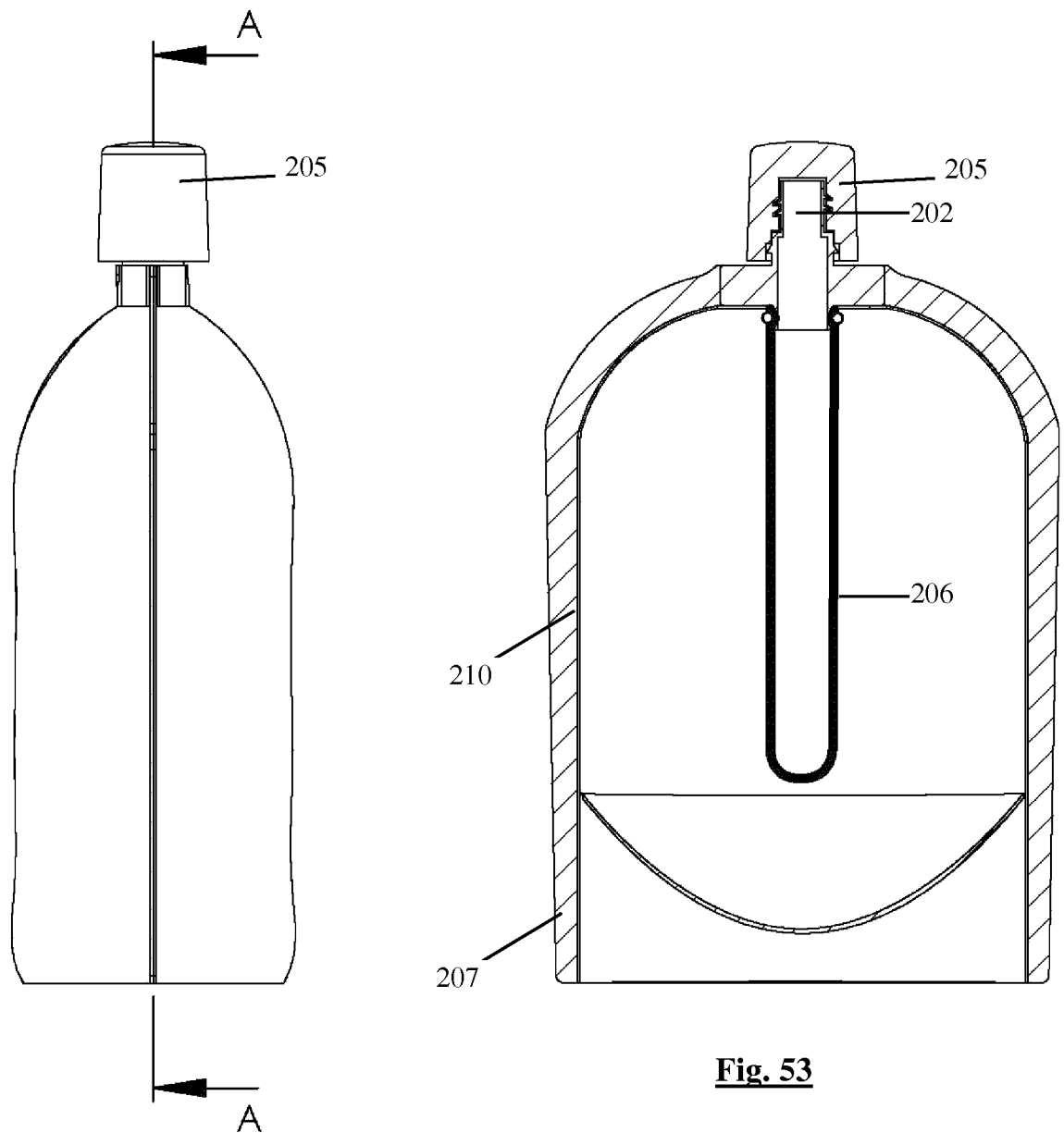
FIG. 52 is a side view of the pouch.
FIG. 53 is a cross sectional view on the line AA in FIG. 52.
Figure 54:
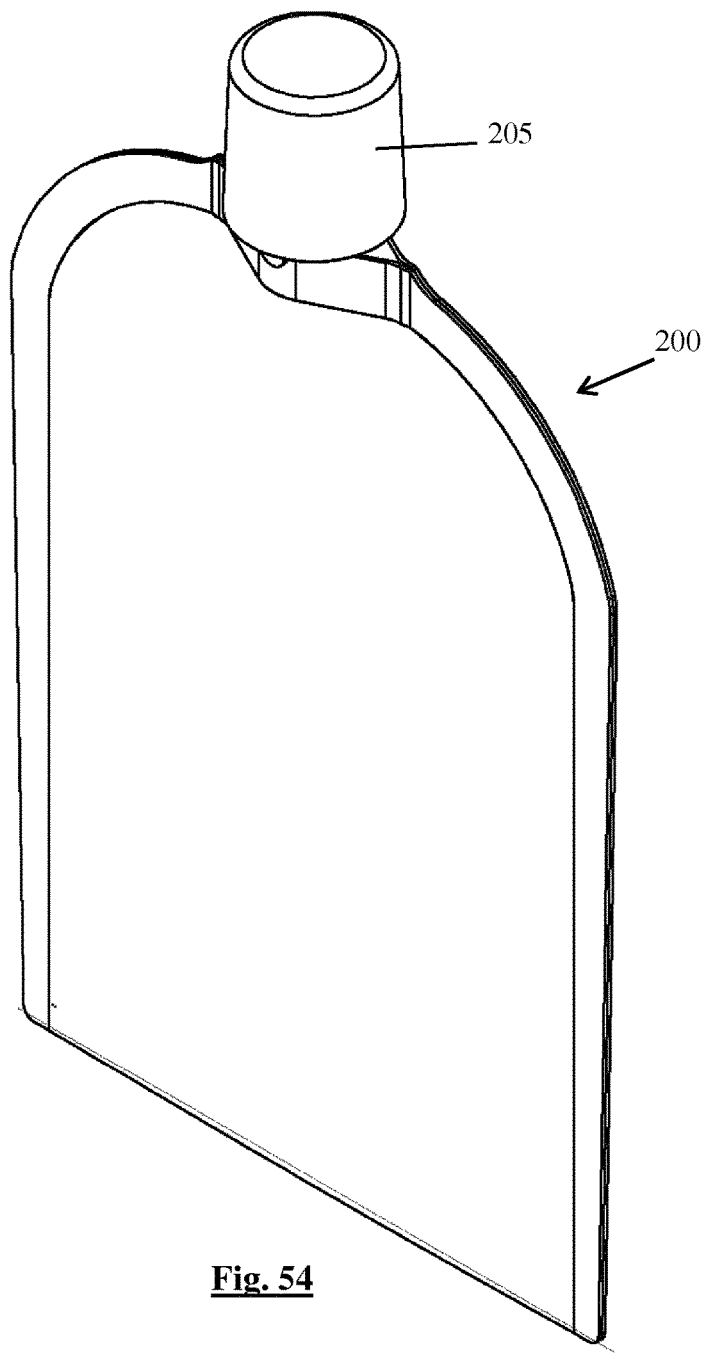
FIGS. 54, 55 and 56 are further views of the pouch.
Figure 55:
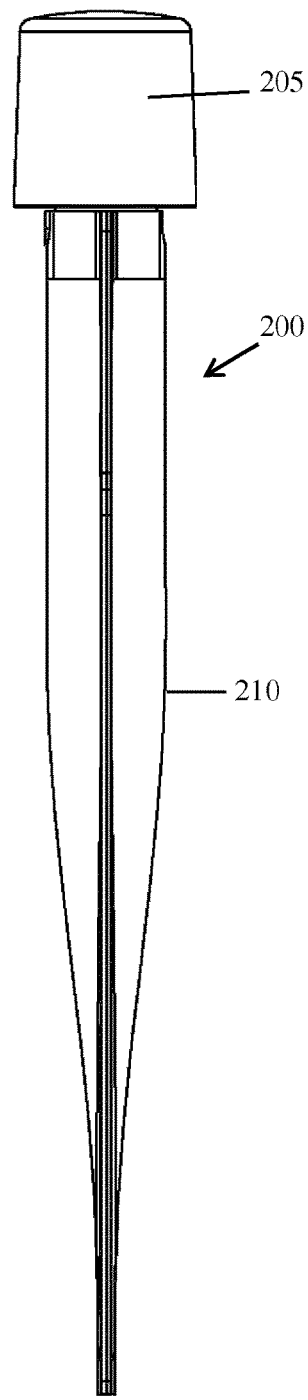
Figure 56:
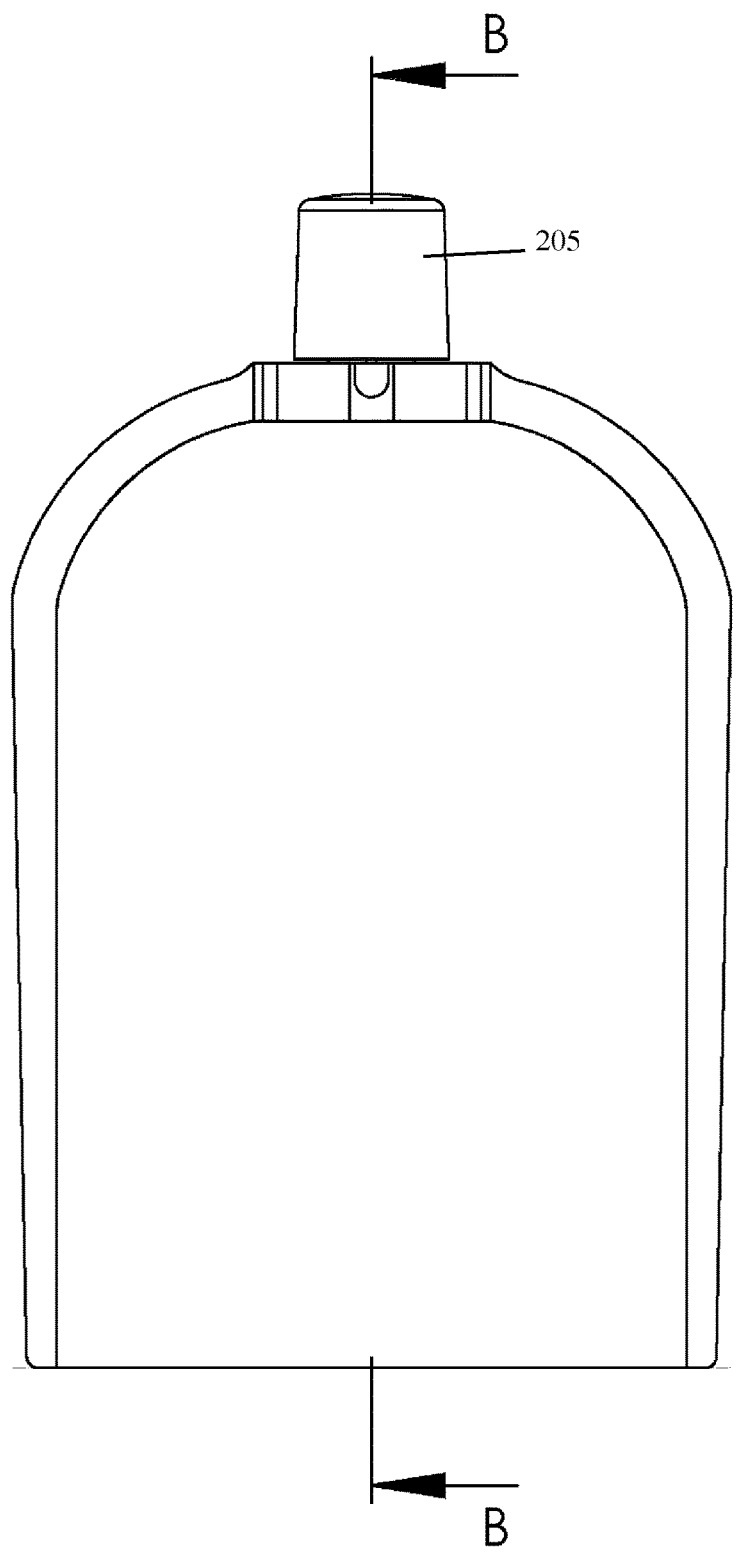
Figure 57:
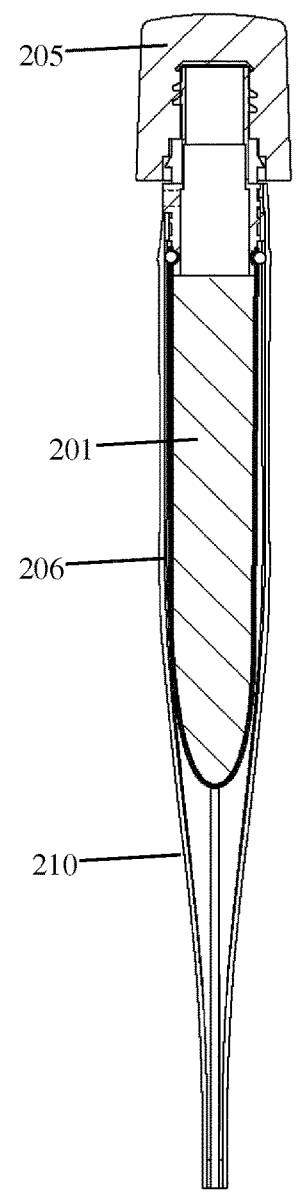
FIG. 57 is a cross sectional view on the line BB in FIG. 56.
Figure 58:
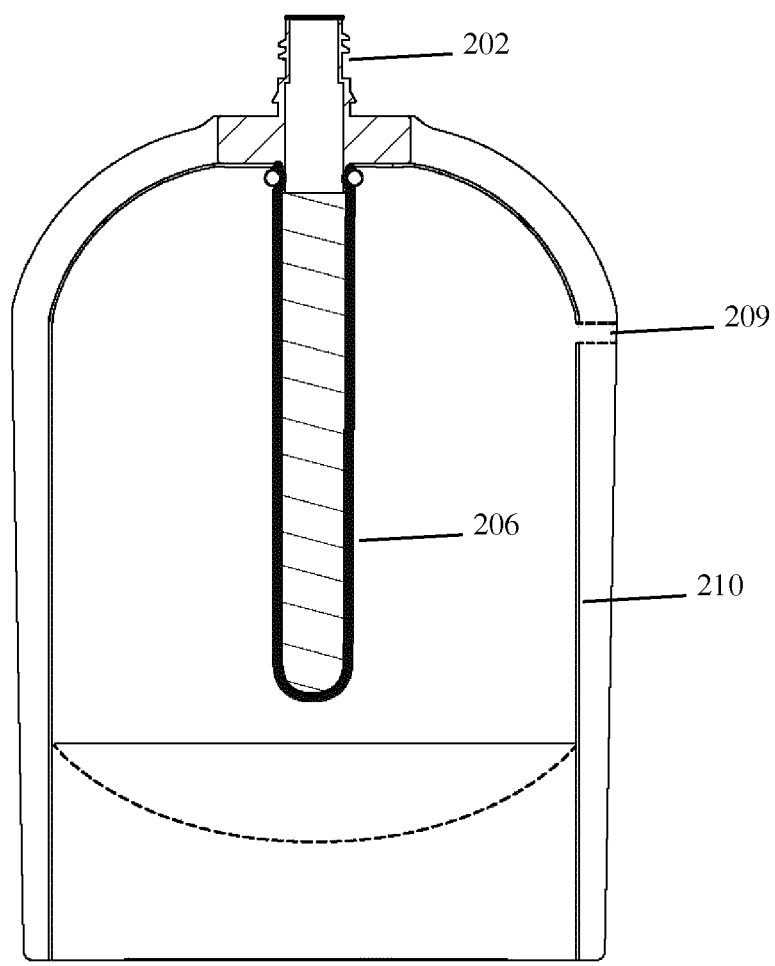
FIGS. 58 to 62 are partially cross sectional vies of the pouch during filling with enteral feed.
Figure 59:
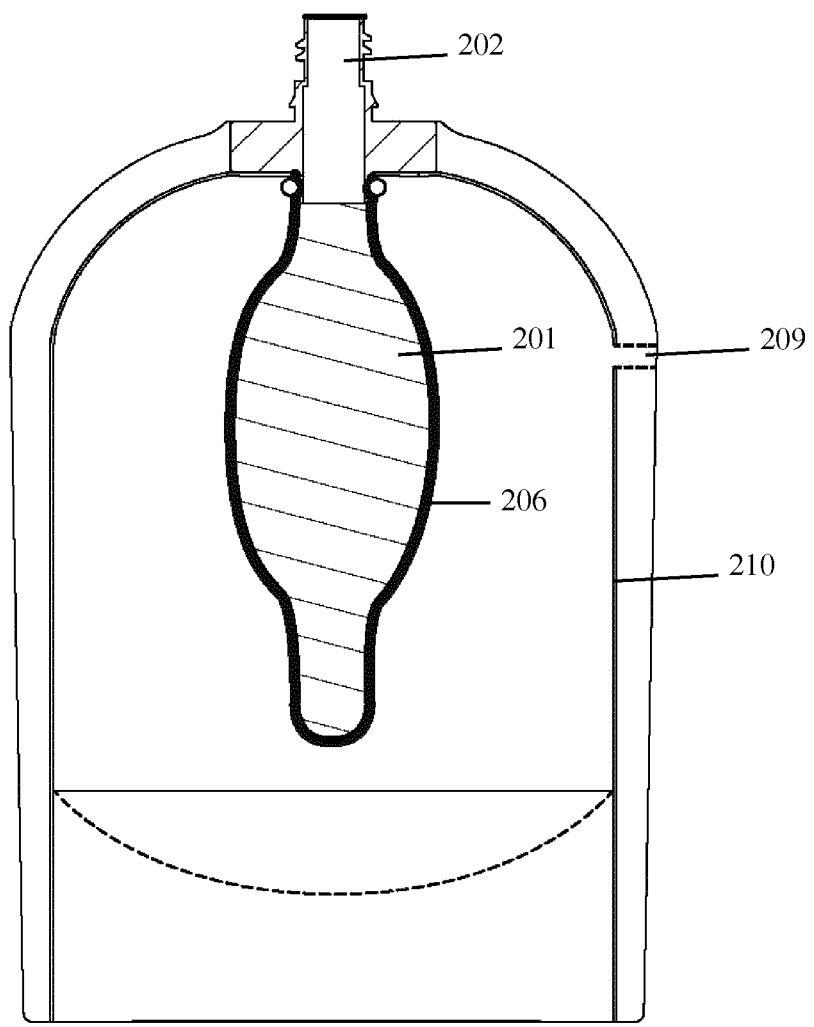
Figure 60:
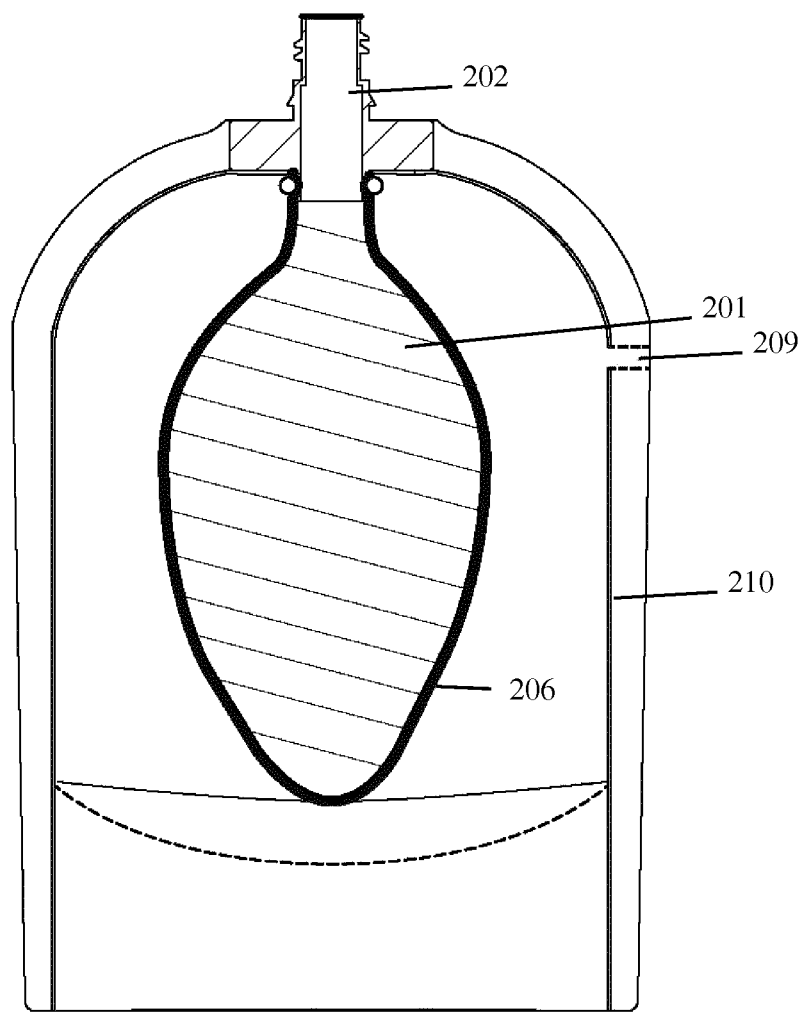
Figure 61:
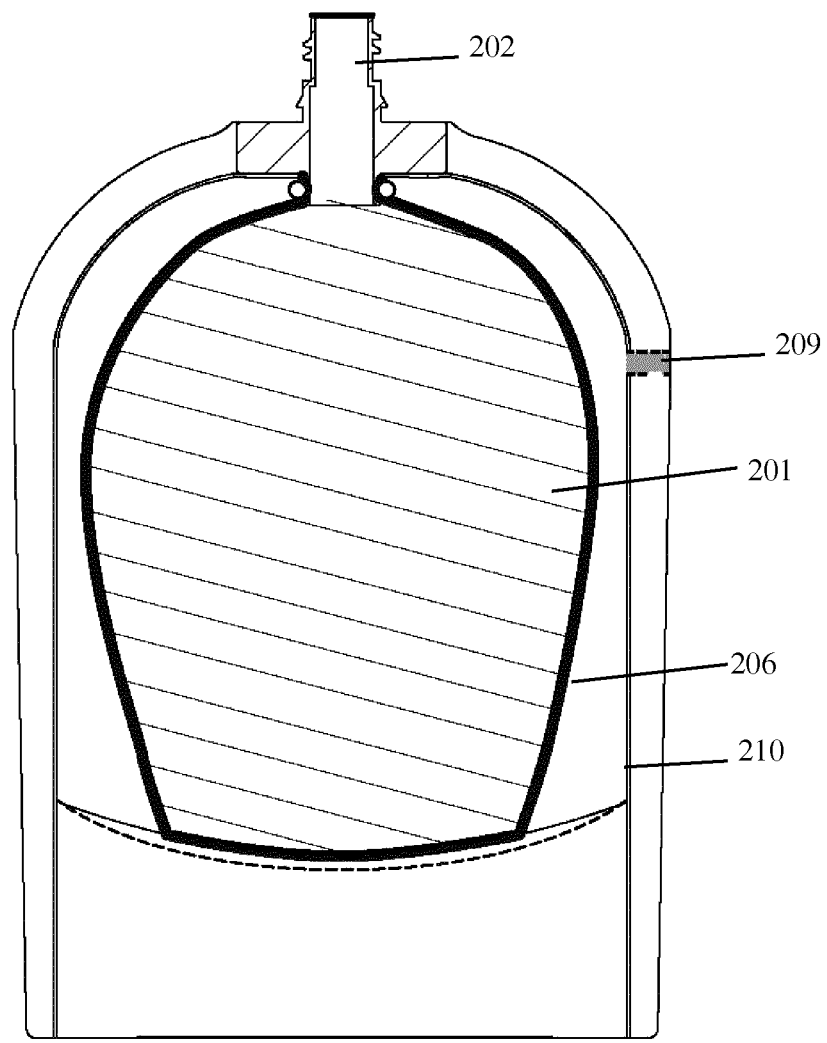
Figure 62:
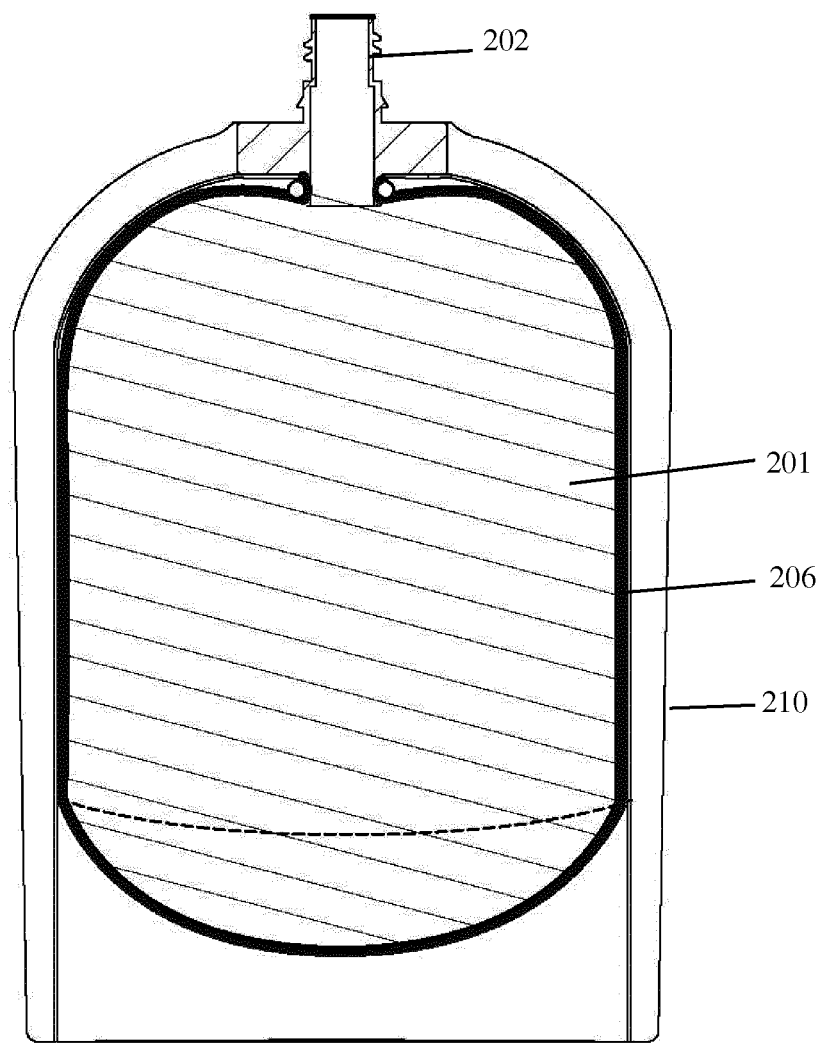
Figure 63:
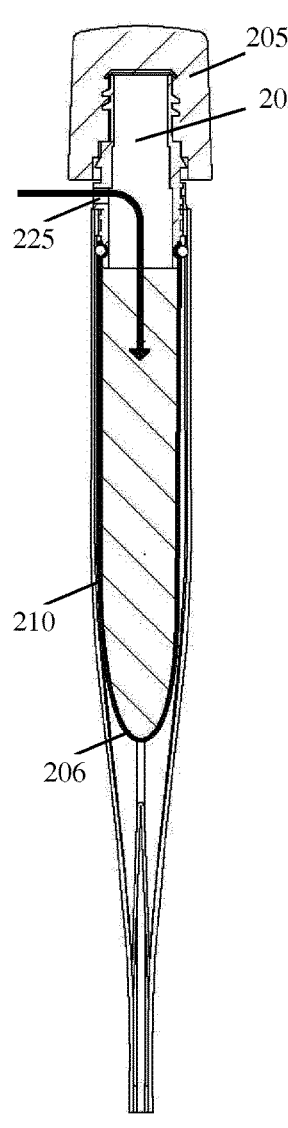
FIGS. 63 to 65 are side sectional views illustrating the filling of the pouch.
Figure 64:
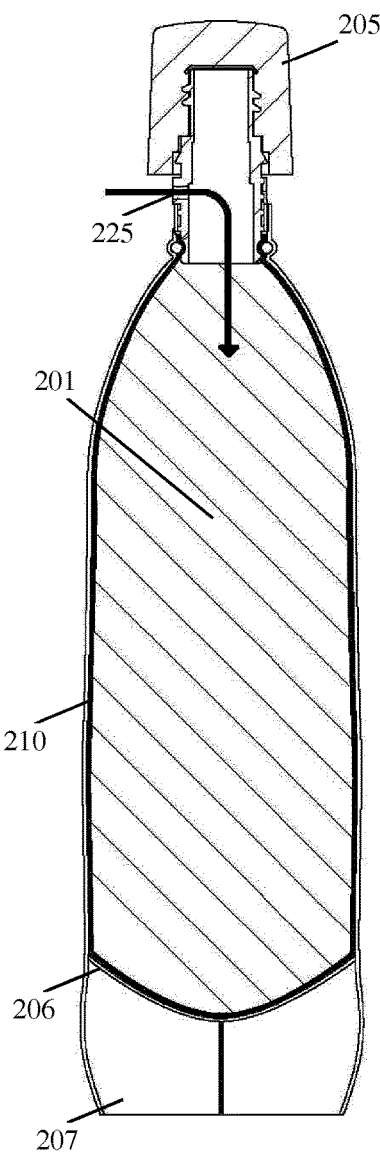
Figure 65:
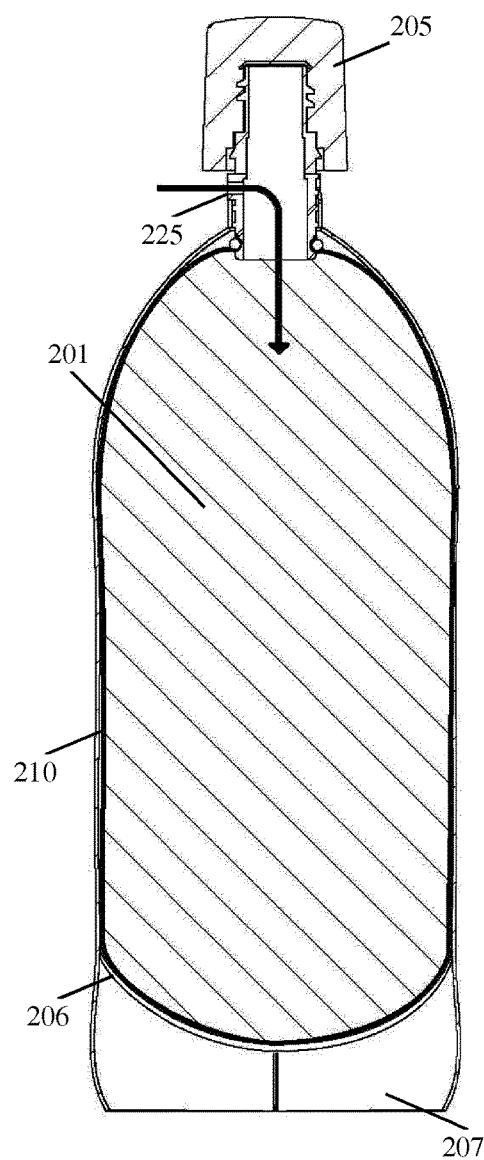
Figure 66:
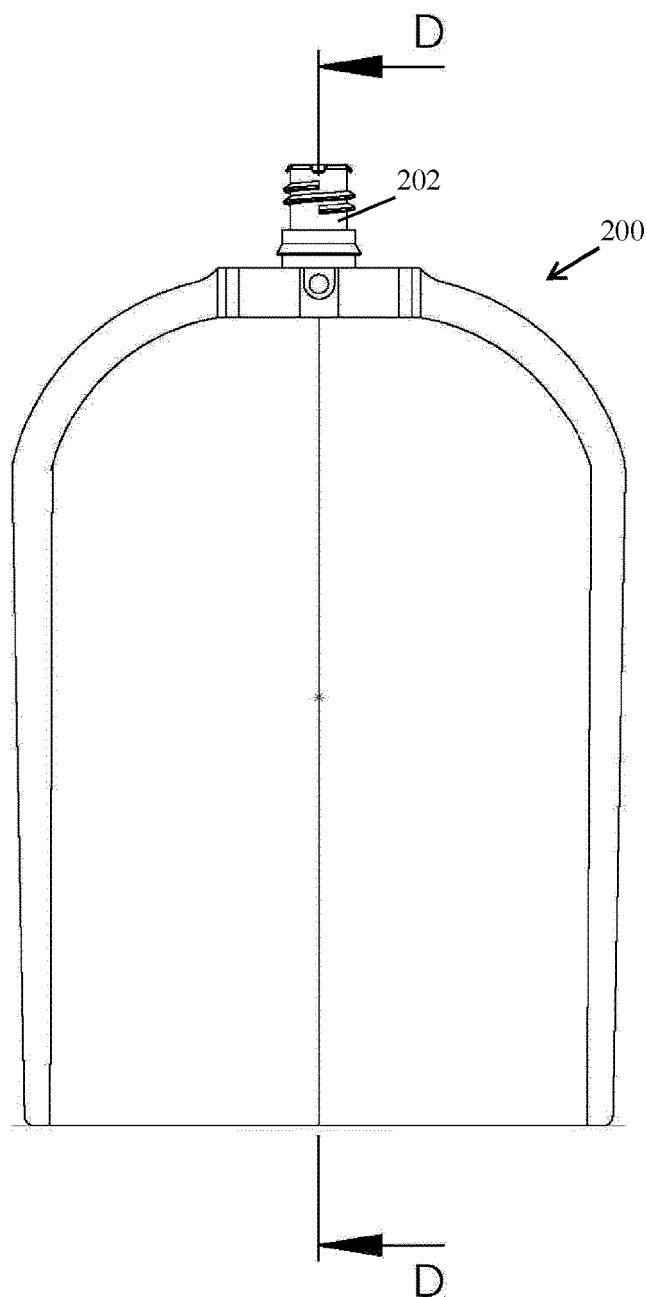
FIG. 66 is a front view of the filled pouch with a cap removed.
Figure 67:
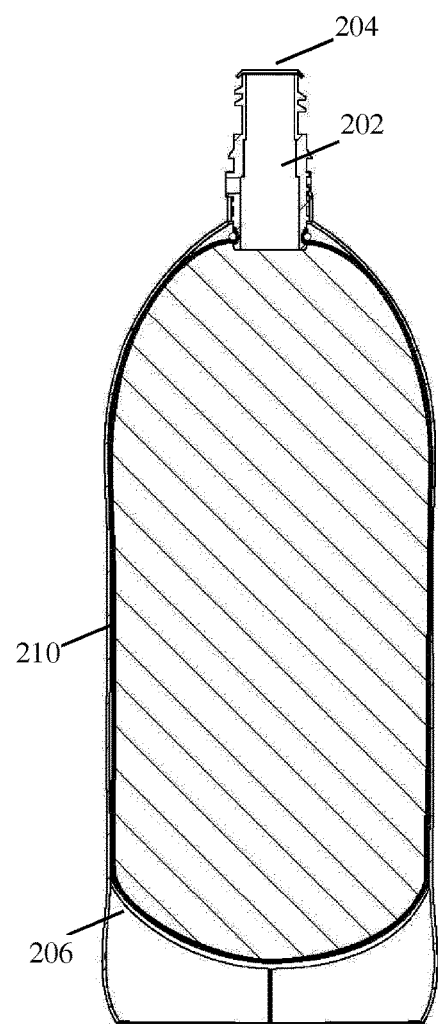
FIG. 67 is a cross sectional view on the line DD in FIG. 66.
Figure 75:
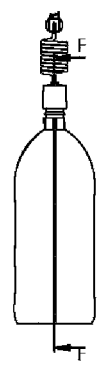
FIG. 75 is a view of the pouch.
Figure 76:
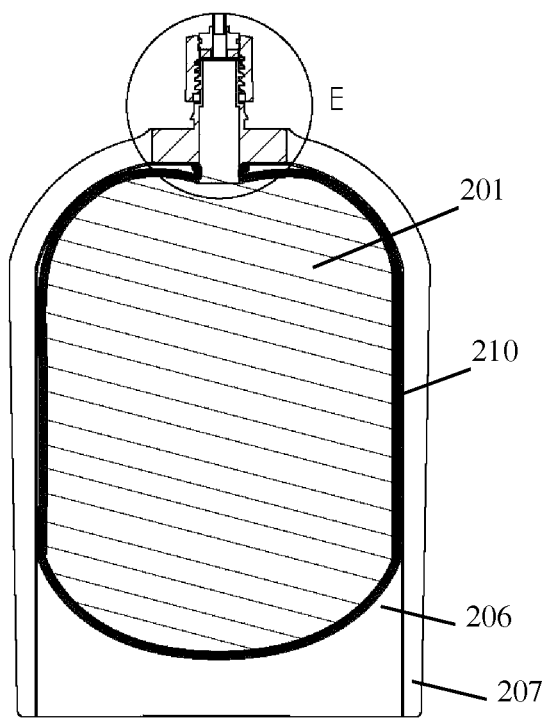
FIG. 76 is a cross sectional view on the line FF of FIG. 75.
Figure 77:
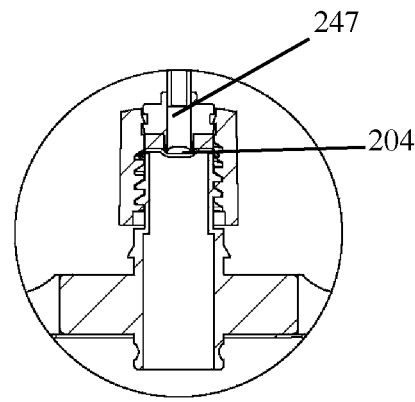
FIG. 77 is an enlarged view of detail E of FIG. 76.
Figure 78:
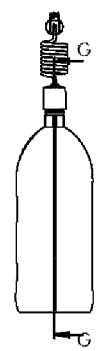
FIG. 78 is a view of the pouch.
Figure 79:
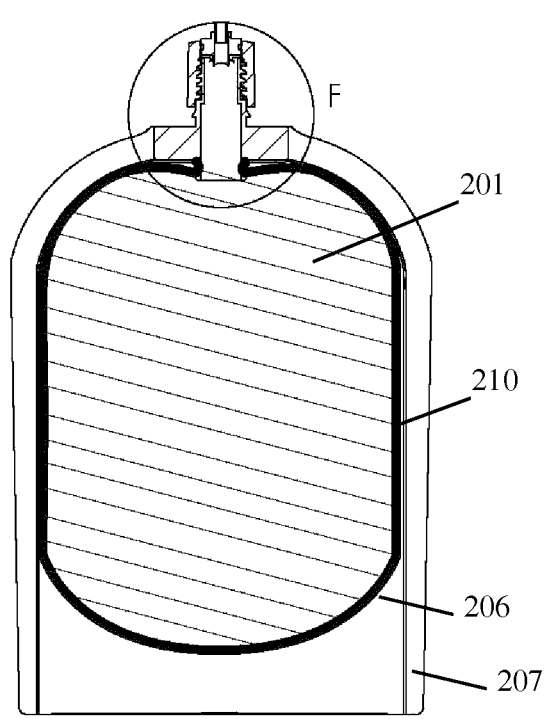
FIG. 79 is a cross sectional view of the line GG of FIG. 78.
Figure 80:
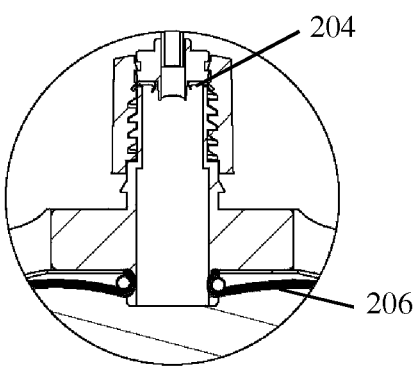
FIG. 80 is an enlarged view of detail F of FIG. 79.
Figure 81:
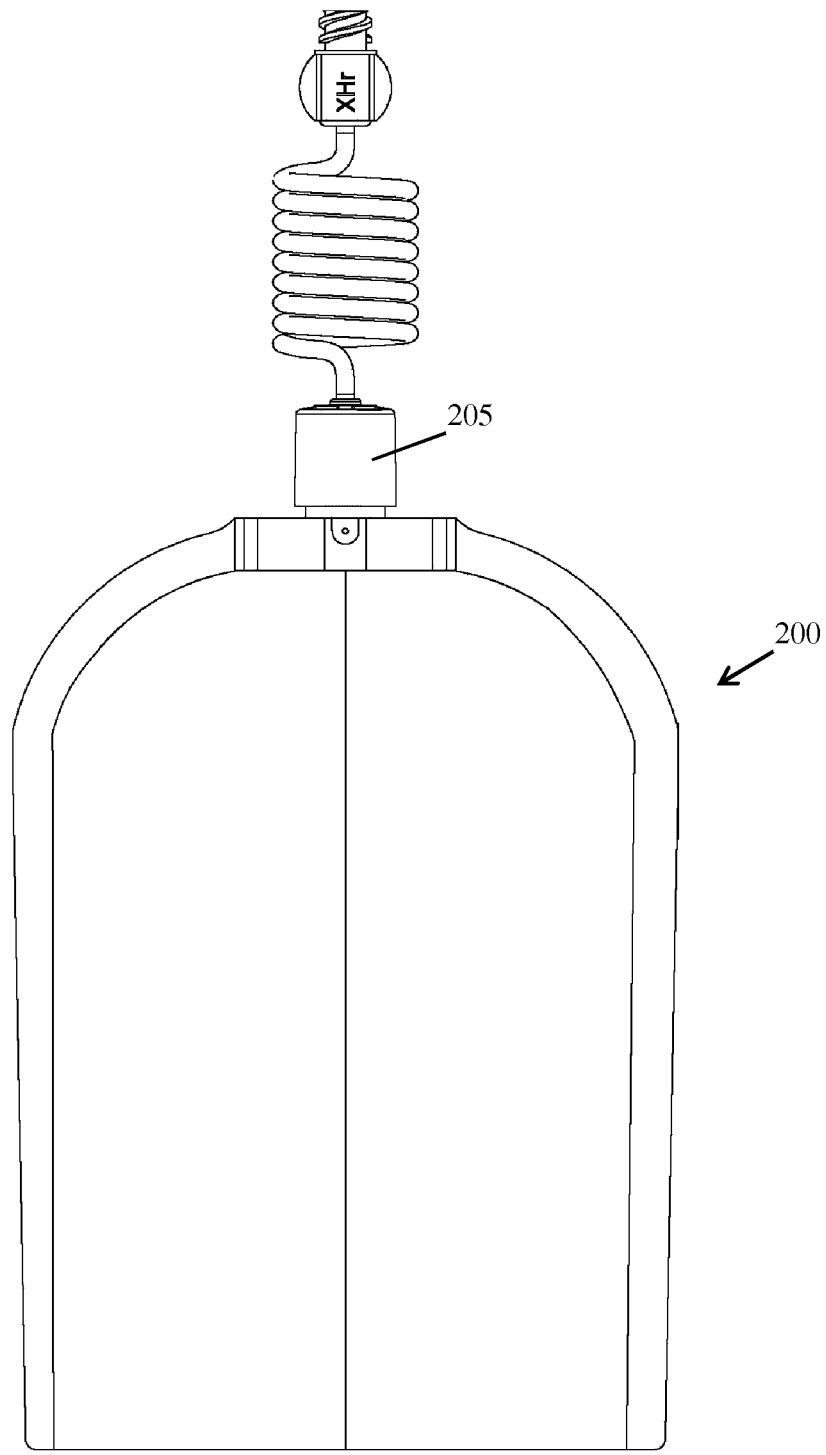
FIG. 81 is a view of the pouch with a regulator coil attached.
Figure 82:
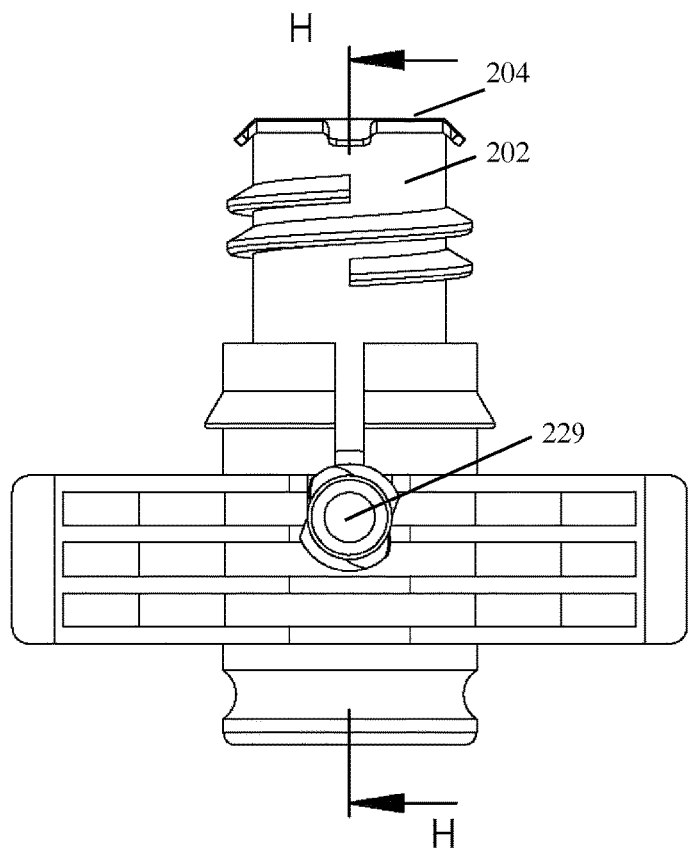
FIG. 82 is a front view of an inlet and outlet part for a pouch.
Figure 83:
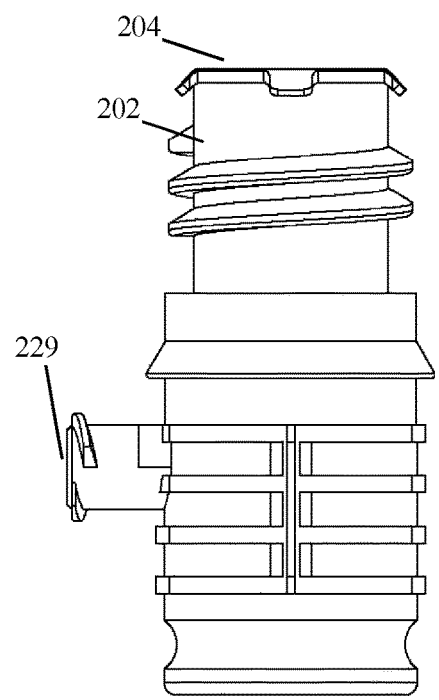
FIG. 83 is a side view and 84 is a top plan view of the part of FIG. 82.
Figure 84:
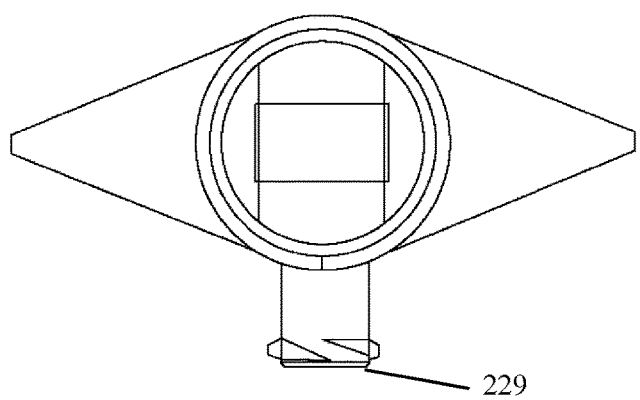
Figure 85:
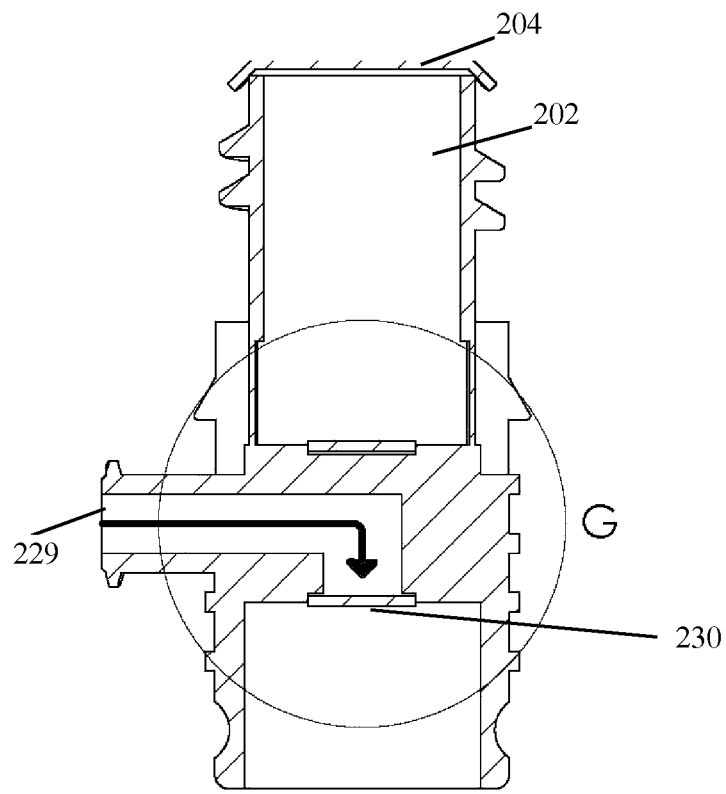
FIG. 85 is a cross sectional view on the line HH of FIG. 82.
Figure 86:
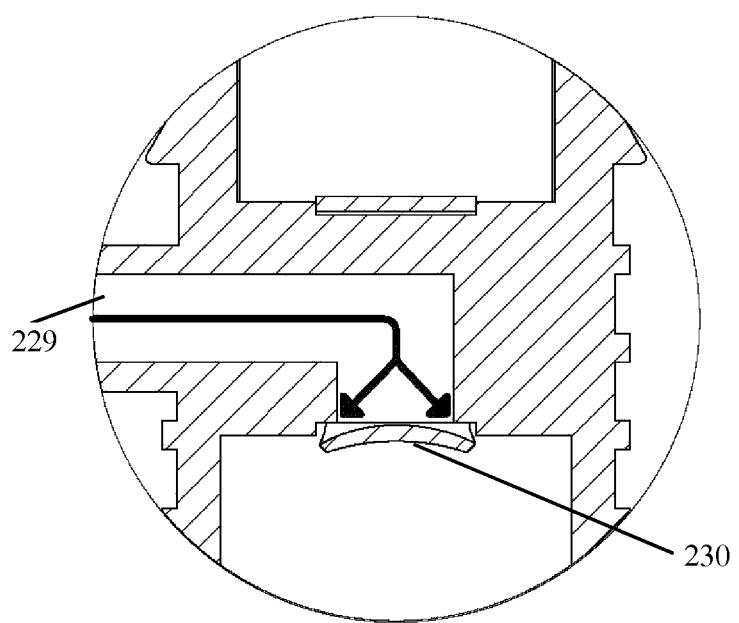
FIG. 86 is an enlarged view of detail G of FIG. 85.
Figure 87:
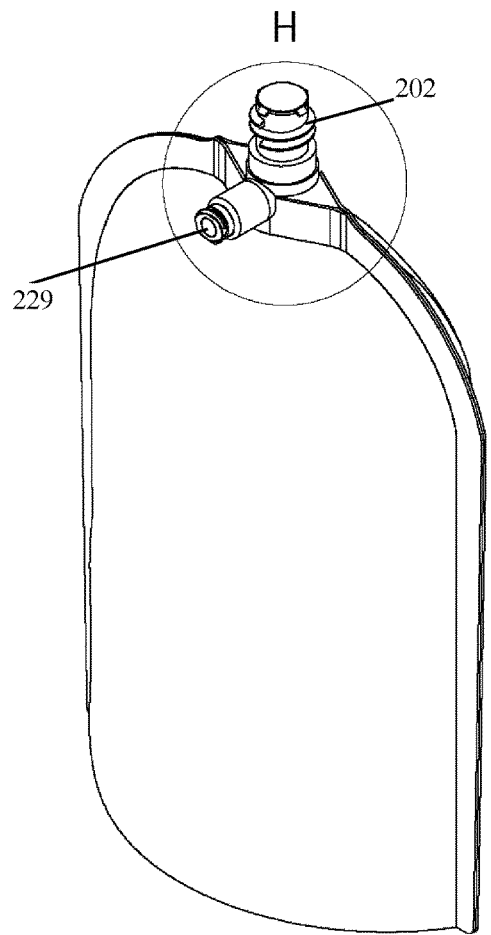
FIG. 87 is a view of a pouch with the inlet and outlet part fitted.
Figure 88:
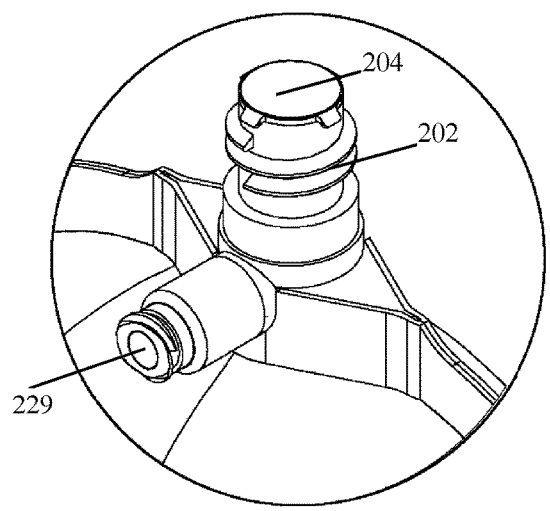
FIG. 88 is an enlarged view of detail H of FIG. 87.
Figure 89:
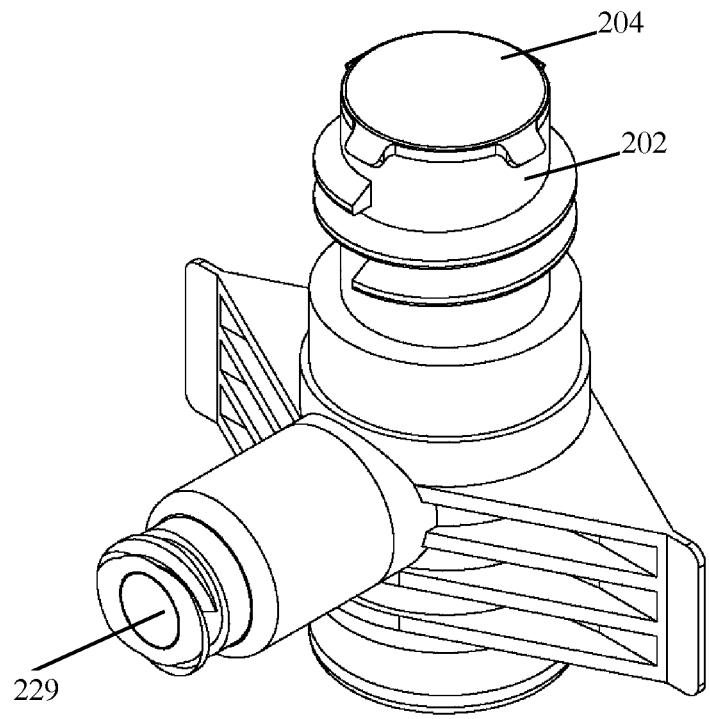
FIG. 89 is a view of another inlet and outlet part for a pouch.
Figure 90:
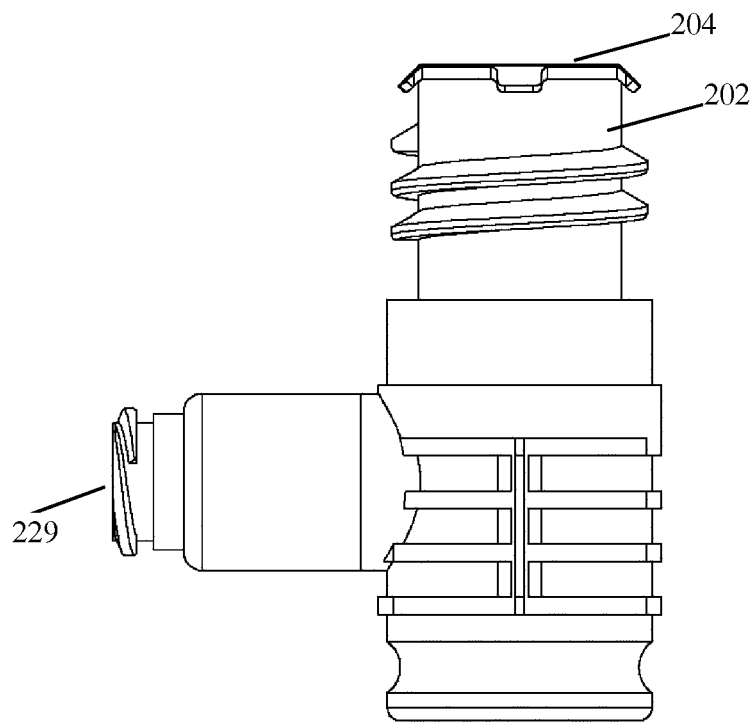
FIG. 90 is a side view and FIG. 91 is a front view of the part of FIG. 89.
Figure 91:
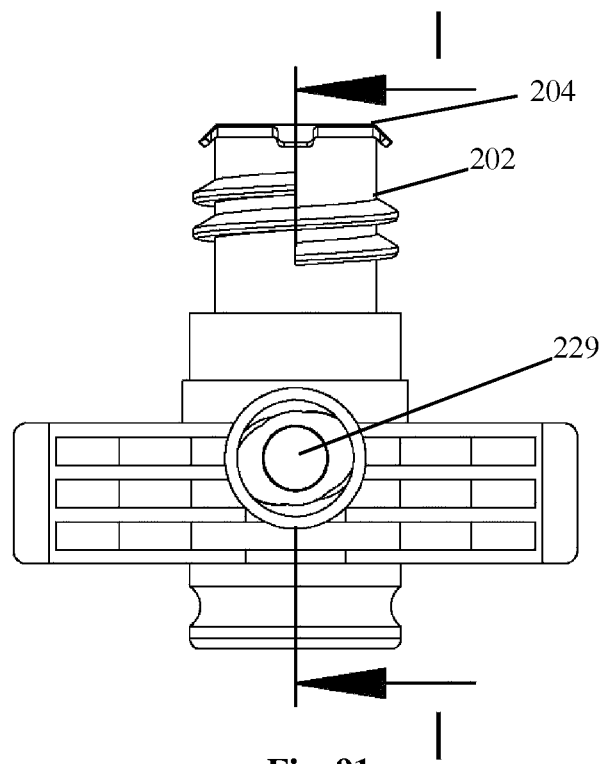

FIG. 45 shows the food pod interacting with the docking station 71. The food pod is placed into a holder in the docking station 120 (FIG. 35). The food pod is calibrated by the docking station and information is displayed on the screen of the docking station 119. Examples of the information include type of fluid; quantity such as 140 ml, flow rate such as 52 ml/ph.

Referring to FIGS. 46 to 69 there is illustrated another enteral feeding apparatus 200 according to the invention. The apparatus comprises a pouch which defines a reservoir for enteral fluid 201 and an outlet 202 for delivery of enteral fluid from the pouch. The outlet 202 has engagement features 203 for engagement with a Leur or ENFit connector for connection to a feeding tube which in turn is connected to a PEG fixture. The outlet 202 may be provided with a seal 204 such as a foil or similar seal and may be covered by a removable cap 205.

The pouch is formed by an expansile element 206 which has an expanded filled configuration and a collapsed configuration. The expansion of the expansile element in the expanded configuration provides the sole force under which enteral fluid is delivered from the pouch. No enteral means such as a pump is required. The expansile element 206 is illustrated in the collapsed or empty configuration particularly in FIGS. 52 to 58. FIGS. 59, 60, 61, 63 and 64 show the gradual expansion of the expansile element as it is filled with enteral fluid. The fully expanded configuration of the expansile element is shown in FIG. 62 and FIGS. 65 to 69.

An exhaust pathway may be provided in the outer barrier to facilitate escape of gas. As the expansile element is filled gas between the expansile element and the outer barrier is exhausted through the exhaust pathway. One such exhaust passage is illustrated in FIGS. 58 to 61 and indicated by the reference 209.

The pouch is adapted to be free standing. In this case the pouch has a bottom gusset 207 which assists in supporting the apparatus so that it can stand freely.

The portable enteral feeding apparatus comprises a substantially gas impermeable barrier. In this case the barrier 210 surrounds the expansile element. The barrier 210 is not significantly expansile but is formed to take up the desired shape when the expansile element is fully expanded. As the expansile element 205 expands it substantially conforms to the shape of the inner surface of the surrounding barrier 210. As fluid is delivered from the pouch a space is formed between the pouch 205 and the barrier 210. As described above, this space may be filled with an inert gas such as Nitrogen.

The barrier comprises a membrane which is substantially gas impermeable. In one case the membrane comprises a metallic foil. Examples of suitable materials for the barrier membrane are given below.

In some embodiments such as those illustrated in FIGS. 46 to 69 the pouch is filled through an inlet filling port 225 which is adjacent to the outlet port.

The filling port 225 is at the end of a passageway into the interior of the expansile element 205. In some cases, such as when filled off-site in a factory or preparation kitchen the filling port is sealed after filling. The sealing may be accomplished in any suitable manner such as by a seal or bung which may be fixed in position by heating and the like.

Figure 92:
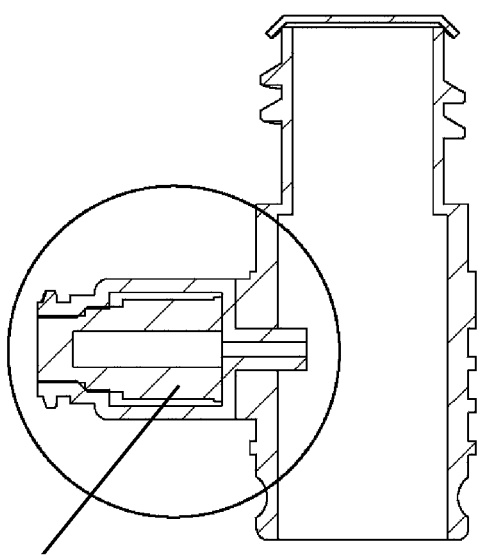
FIG. 92 is a cross sectional view on the line I-I of FIG. 91.
Figure 93:
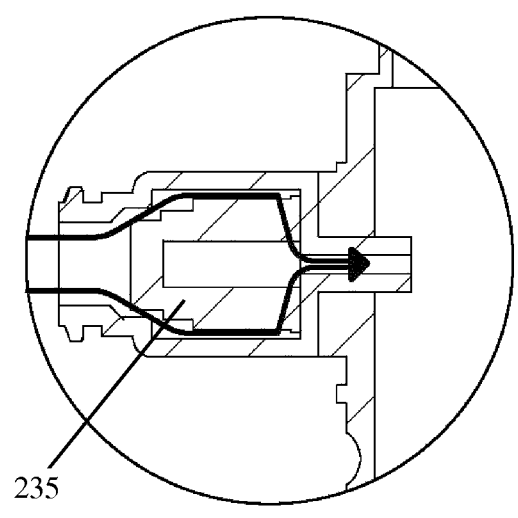
FIG. 93 is an enlarged view of detail I of FIG. 92.
Figure 94:
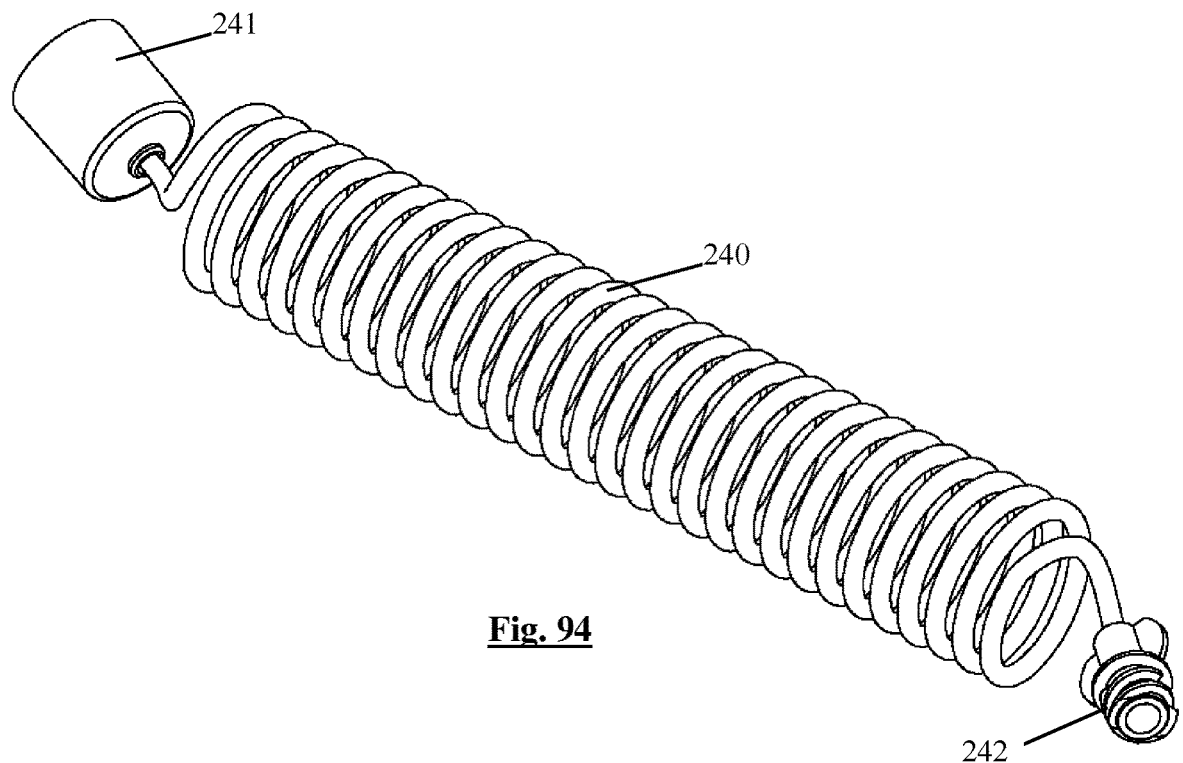
Figure 95:
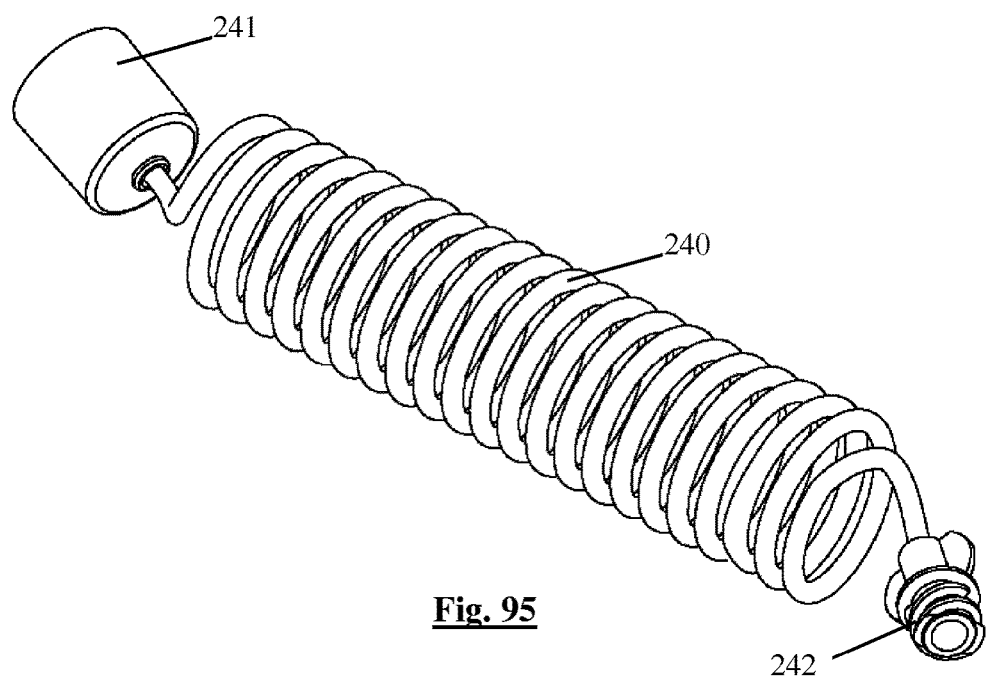
Figures 96, 97, 98, 99:
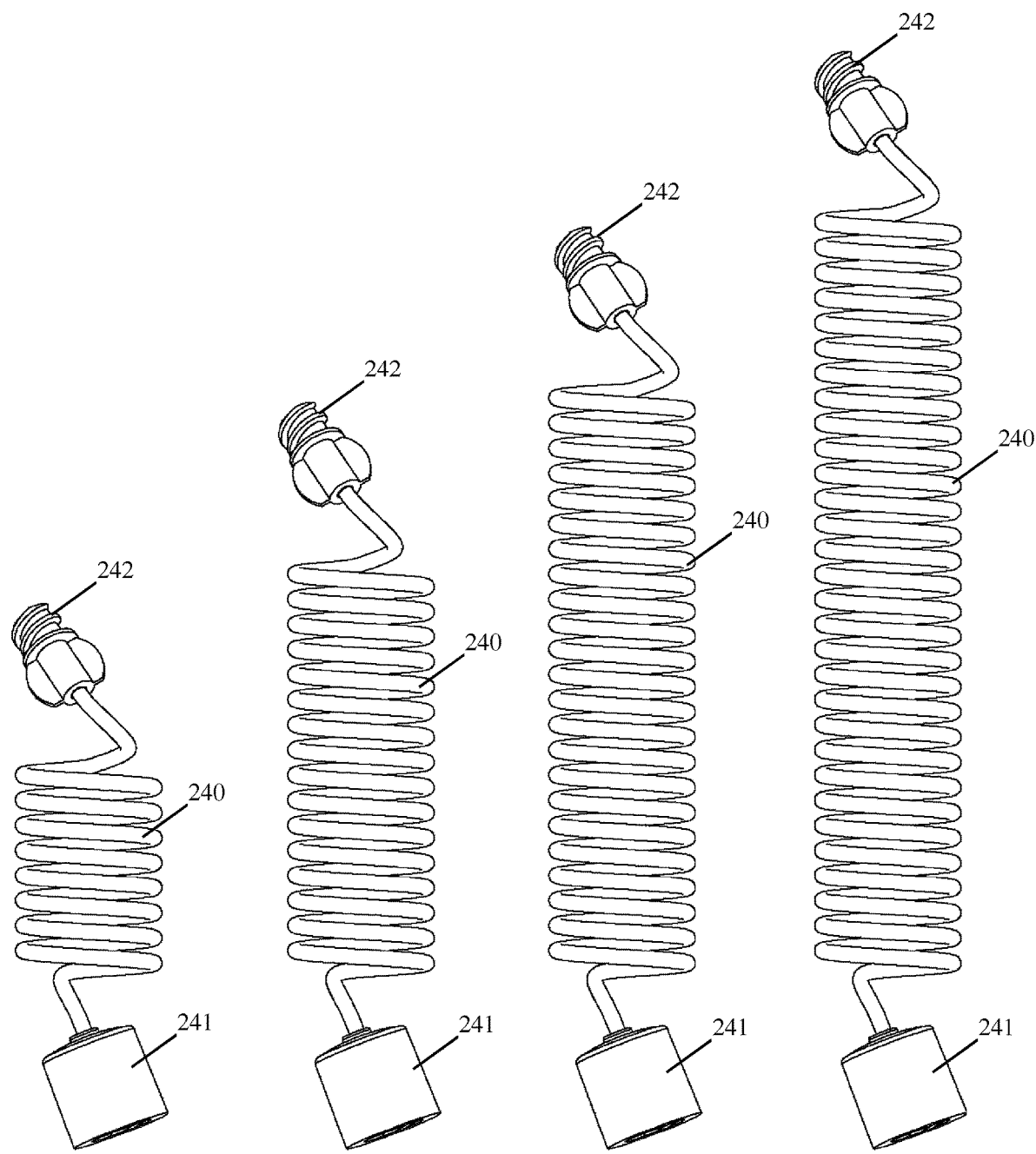
Figure 105:
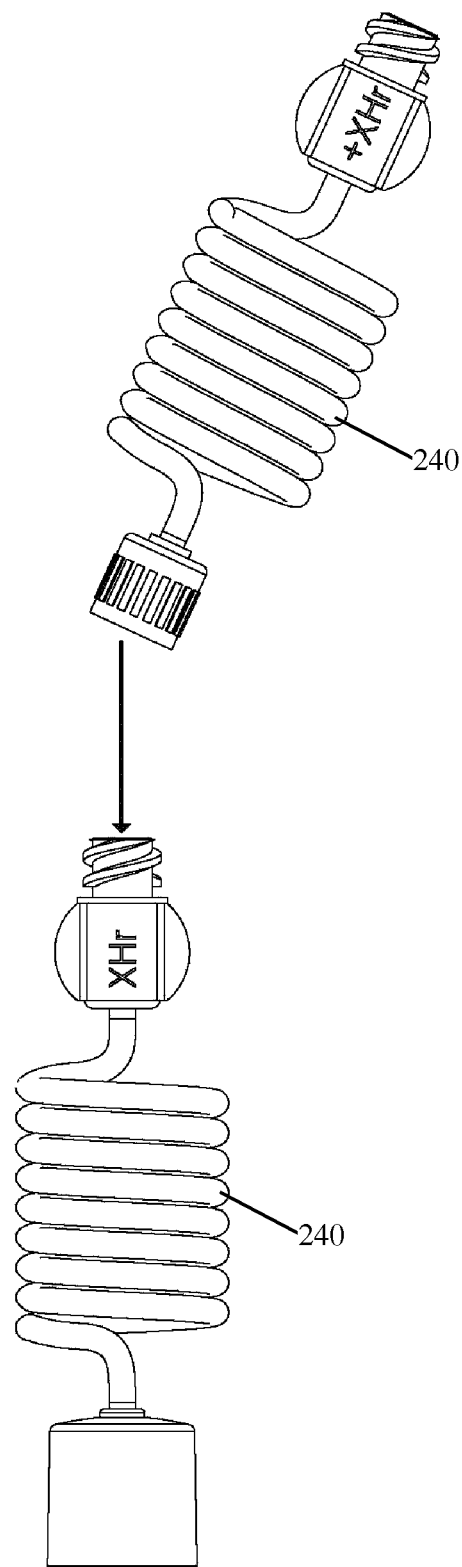
FIG. 105 is a view of two regulator coils being joined together.

In other embodiments such as those illustrated in FIGS. 82 to 93 there is a defined inlet filling port 229 through which the enteral fluid is filled. In these cases a valve such as a non-return valve which may be a flap or leaf valve 230 is provided through which enteral fluid is delivered as illustrated particularly in FIGS. 85 and 86. One alternative valve such as a block valve 235 is illustrated in FIGS. 92 and 93.

Figure 106:
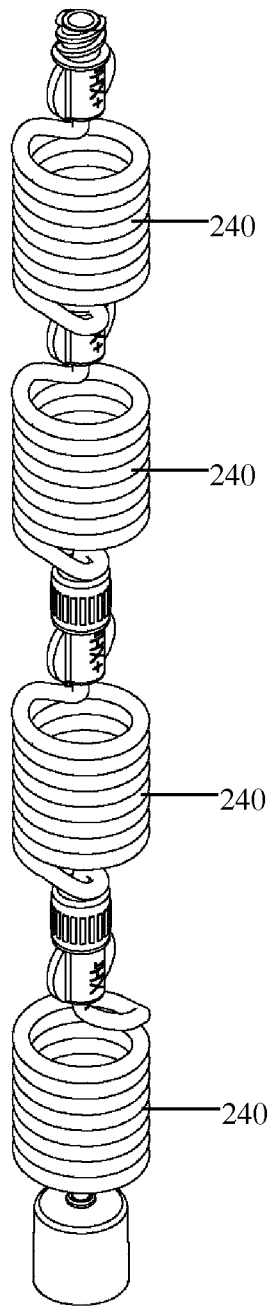
FIGS. 106 and 107 are views of regulator coils joined together.
Figure 107:
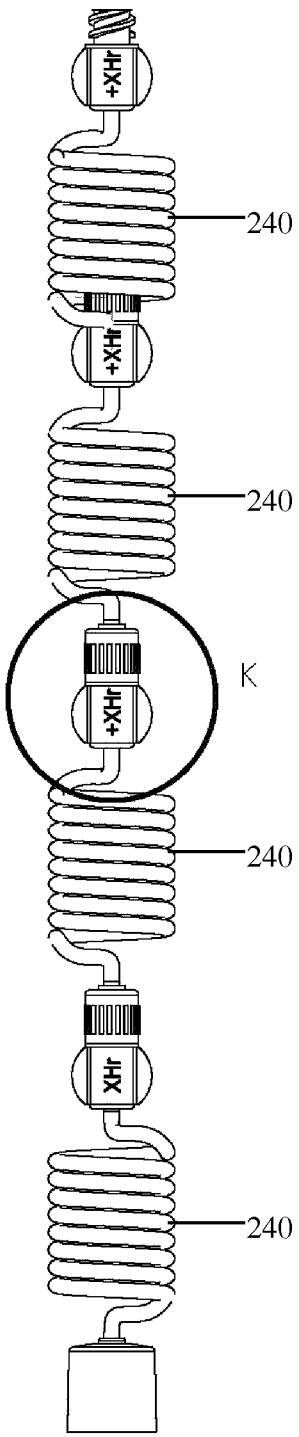
Figure 108:
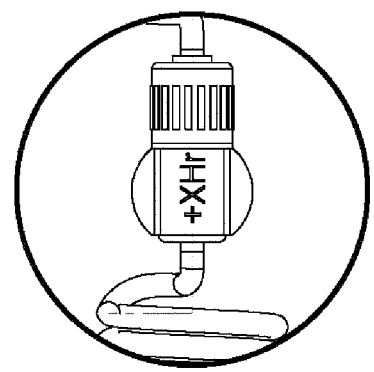
FIG. 108 is an enlarged view of detail K of FIG. 107.
Figure 113:
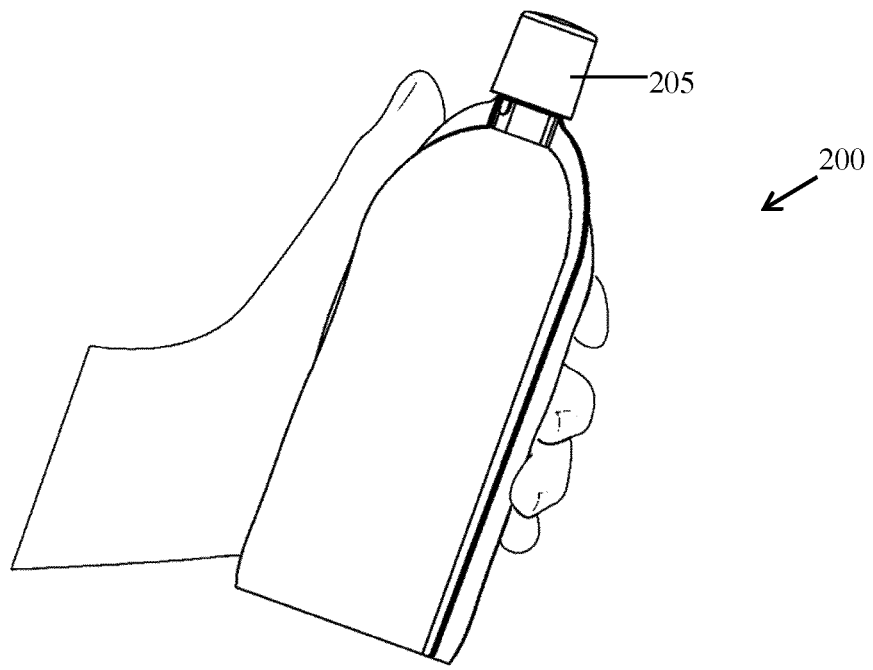
FIGS. 113 to 120 illustrate a pouch of various stages of use.
Figure 114:
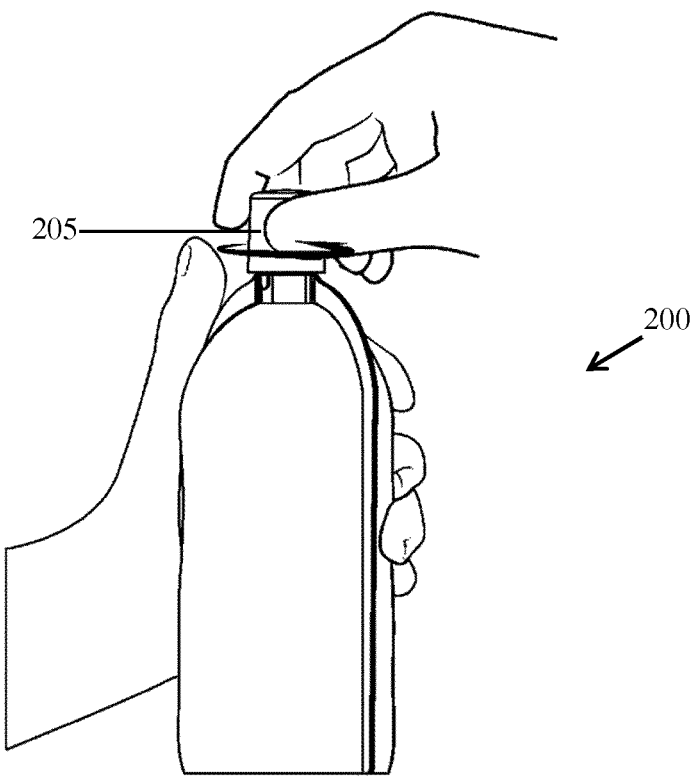
Figure 115:
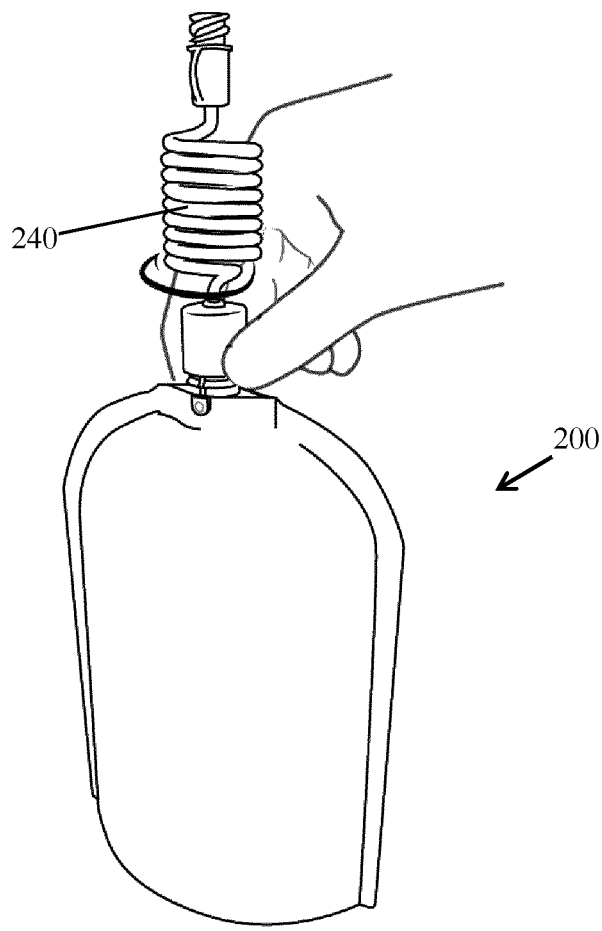
Figure 116:
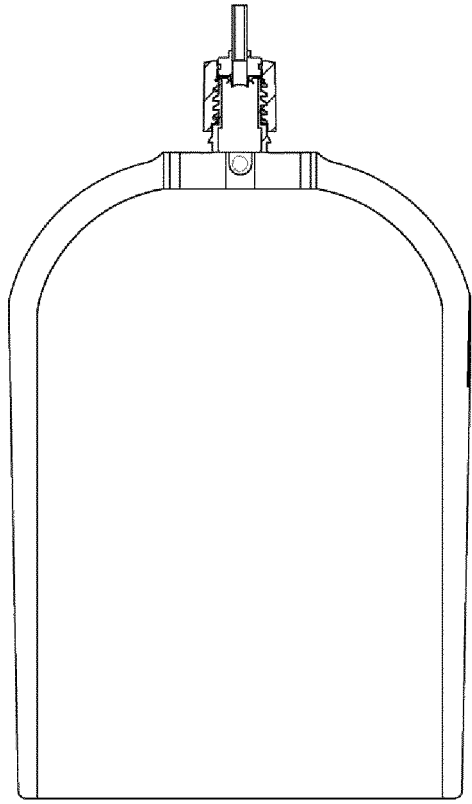
Figure 117:
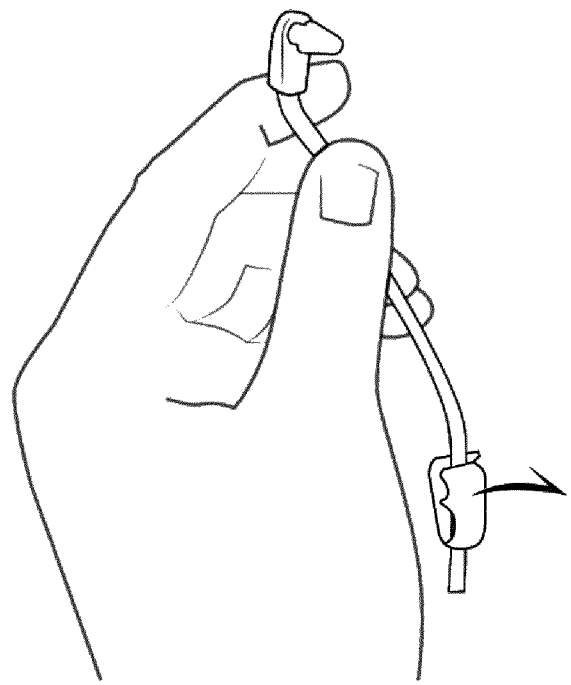
Figure 118:
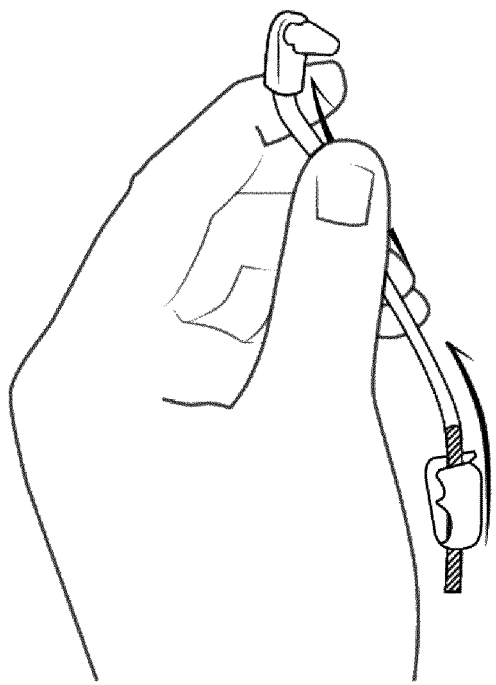
Figure 119:
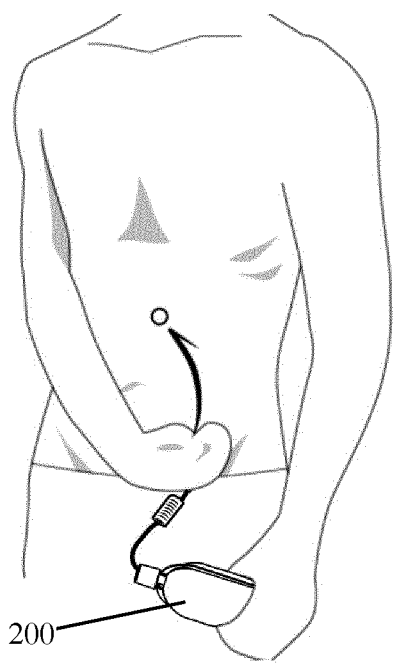
Figure 120:
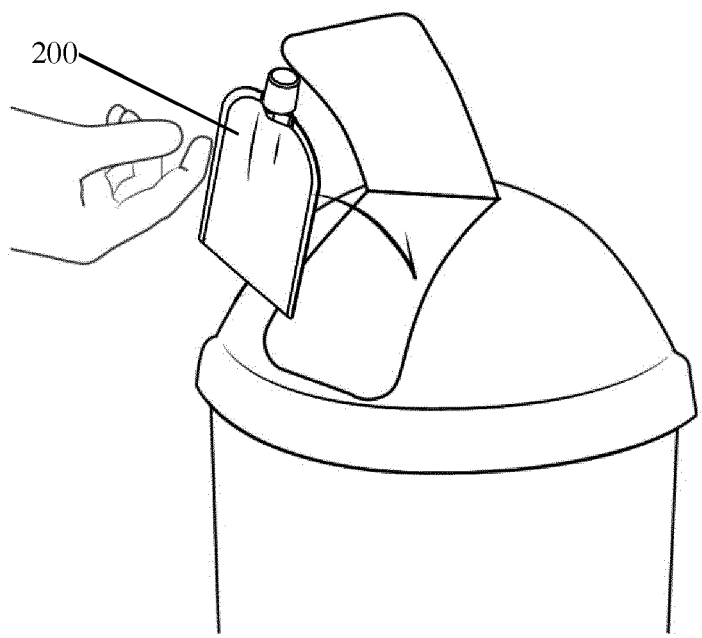
Figure 121:
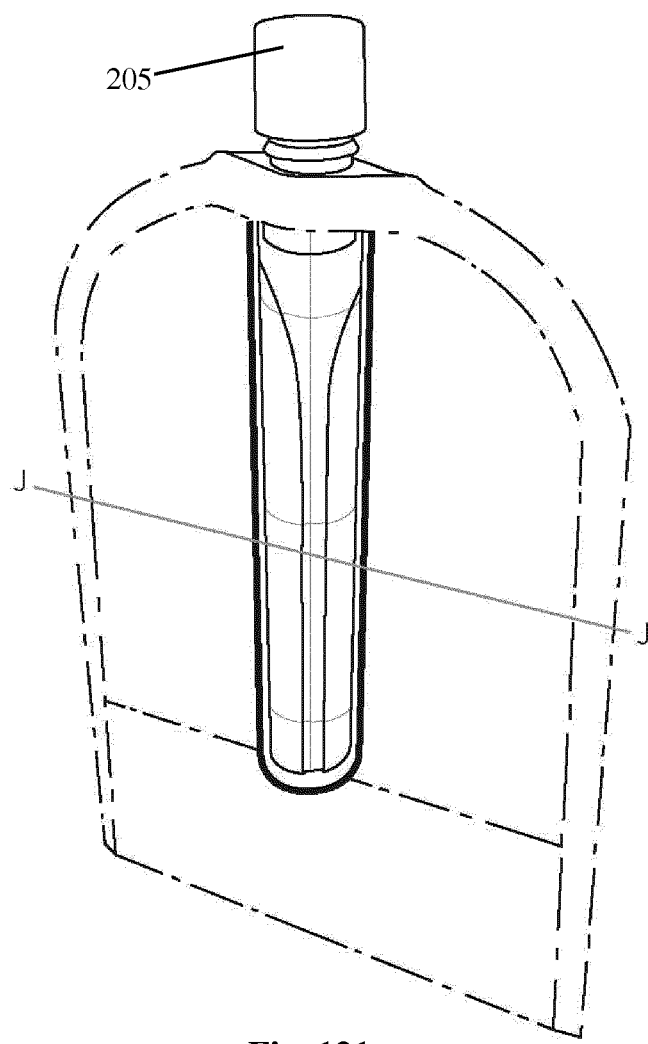
FIG. 121 is a view of another enteral feed pouch according to the invention in an unfilled configuration.
Figure 122:
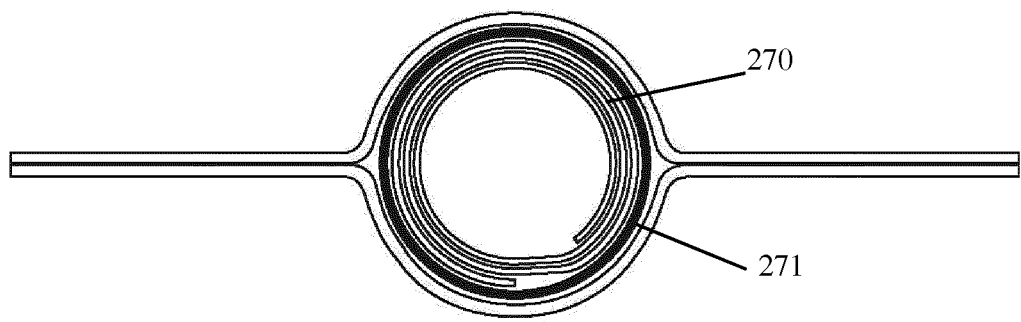
FIG. 122 is a cross sectional view on the line JJ of FIG. 21.
Figure 123:
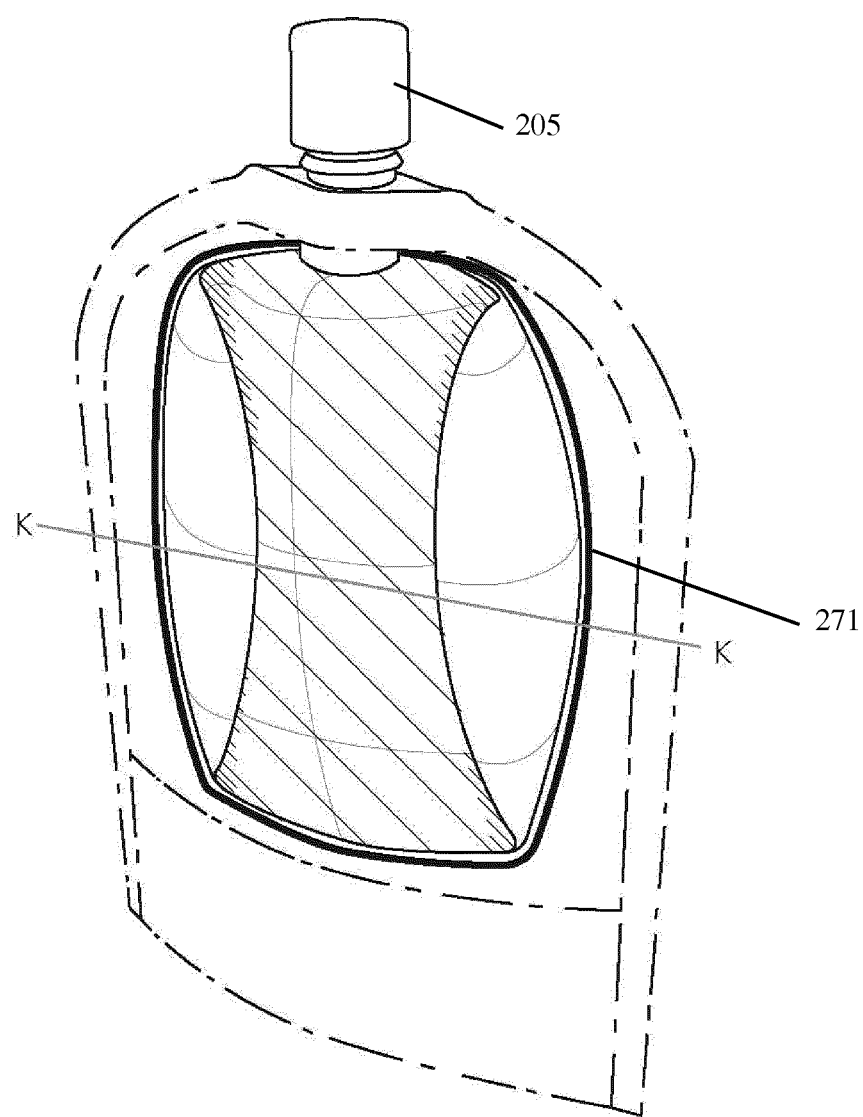
FIG. 123 is a view of the feed pouch partially filled.

Any suitable flow regulator may be used to control the flow of fluid from the pouch, when delivering enteral fluid to a PEG. The regulator may be an adjustable bore regulator such as described above with reference to FIGS. 16 to 18. An alternative regulating system is a friction regulator. One such friction regulator is illustrated in FIGS. 70 to 81 and 94 to 111. In this case the regulator comprises a coiled tube 240 through which enteral fluid flows from an inlet end 241 to an outlet end 242. The inlet and outlet ends are configured for mounting to a Leur or an ENFit connector so that the inlet end 241 of the coil 240 can be mounted to the outlet of the pouch and the outlet end can be mounted to a feeding tube which is connected to a PEG. The flow can be regulated by selecting a particular coil—for example a longer coil will offer greater resistance to flow than a smaller coil and hence provide a reduced flow rate. Coils of different lengths are illustrated in FIGS. 96 to 99. The coils may have indicia 245 to indicate the set outlet flow rate such as 100 ml/hour. Rather than providing a plurality of coils of different lengths similar coils may be joined together in series as illustrated in FIGS. 106 to 108.

The viscosity of enteral feeds can range from 3 cPs (centipoise) to 400 cp. A low viscosity enteral feed has a viscosity in the range 1-100 cp. Enteral feed with high viscosity is particularly challenging to handle.

The use of a coiled tube provides a regulator that can accommodate a wide range of enteral feed. The length of the coil can be selected to achieve the desired flow. A plurality of interconnectable coiled tubes can be tailored to a desired flow in a modular fashion. To allow for higher viscosity feeds the regulator is modular allowing for lengths of coiled tubing to be added or subtracted to facilitate a desired flow rate from 50 ml per hour to 250 ml per hour for a range of differing viscosity enteral feed.

The inlet end port may comprise a cap having a projection 247 which pierces the seal 204 at the pouch inlet 202 when fitted. This is illustrated in FIGS. 70 to 80.

The coil of FIGS. 109 to 112 include a side port 250. This acts as a flush port for flushing the line or addition of a medicament. This is located away from the user to ensure that it does not interfere with the user's comfort.

The steps involved in use of the enteral feeding apparatus are illustrated in FIGS. 113 to 120 and the various steps involved are as described in detail above.

The invention provides a wearable, portable and mobile enteral feeding system that allows for user mobility and versatility by delivering a range of variable fixed flow rates via a tubing set and expansile pouch. The enteral feeding system can be home filled or factory filled allowing for increased and improved shelf-life via a gas impermeable barrier surrounding the expansile pouch.

The enteral feeding apparatus of the invention has no electronic moving parts so that there is no need for a power supply and no noise is generated. There is no disruption to the user as the feed is being delivered.

The pod may be used to add and store powdered formulas (such as whey formulas) with hydration of water or milk to be added when ready for use.

The coiled tube regulator provides a single use variable flow rate tubing set. The rate of flow can be increased or decreased by shorting or extending the tube set by way of inline connectors. Once the desired rate has been chosen the rate is set for the duration of the feeding time, eliminating the risk of free flow from the device. The tubing is coiled to prevent kinking and to allow the device to be both wearable and fixed at the bedside. The length of the user line that can snag is reduced, thus avoiding the risk of accidental disconnection at the PEG site.

Figure 124:
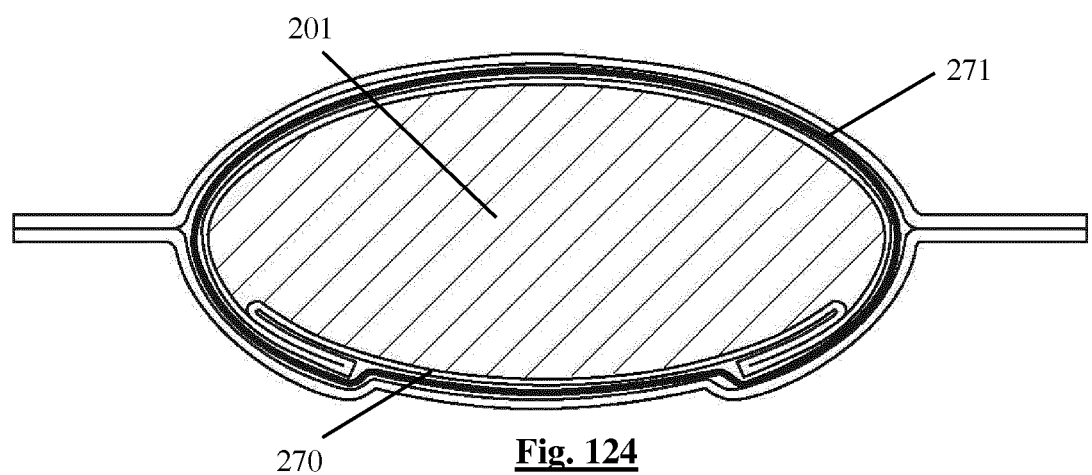
FIG. 124 is a cross sectional view on the line KK of FIG. 123.
Figure 125:
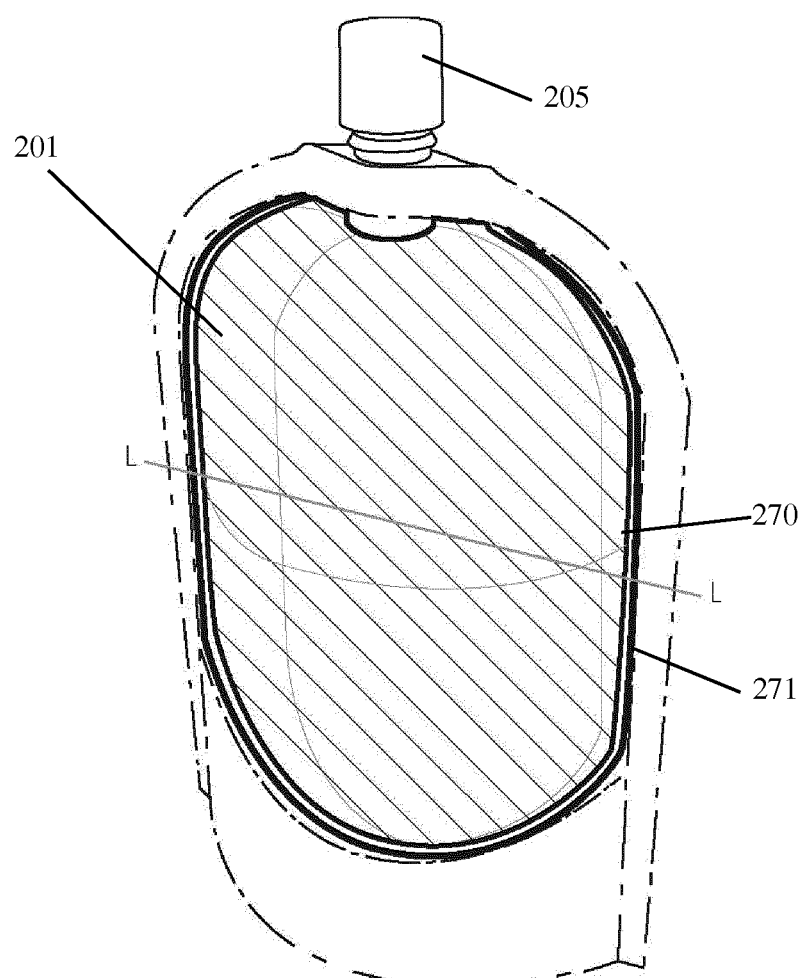
FIG. 125 is a view of the pouch filled.
Figure 126:
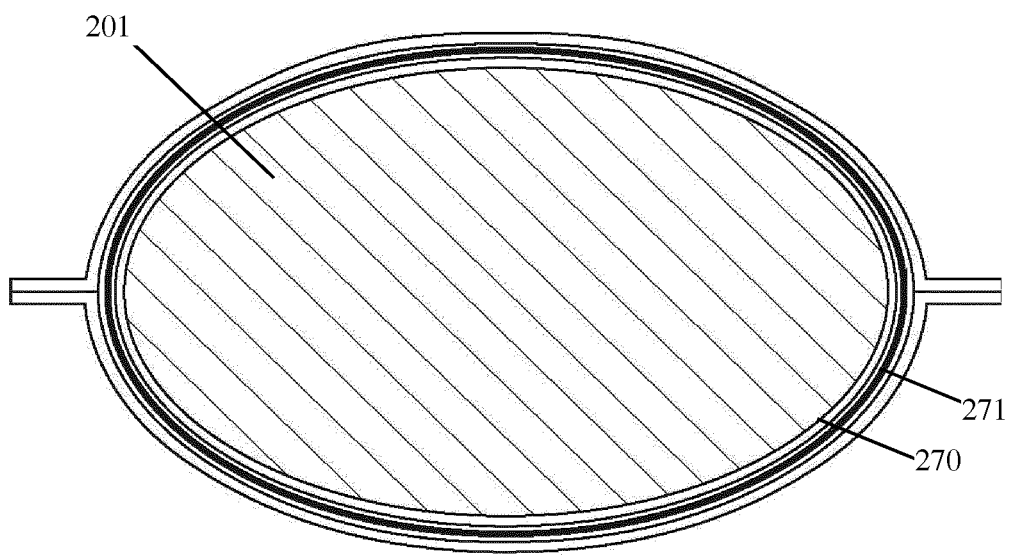
FIG. 126 is a cross sectional view on the line LL of FIG. 125.

An inner barrier may be provided within the expansile member so that the expansile member is not in direct contact with the enteral fluid. In this way any possible leaching from the expansile material is avoided and may facilitate usage of lower grade and lower cost expansile materials. One such arrangement is illustrated in FIGS. 121 to 126 in which an internal barrier 270 is provided within an outer expansile element 271. The barrier material is not expansile but changes from a compressed/folded and/or rolled configuration in an empty configuration (FIG. 121, 122) to an unfolded and/or unrolled configuration illustrated in FIGS. 125 and 126. An intermediate partially unfolded configuration is illustrated in FIGS. 125 and 124.

The inner barrier may be of any suitable material such as PET. The inner barrier may be a laminate.

Figure 127:
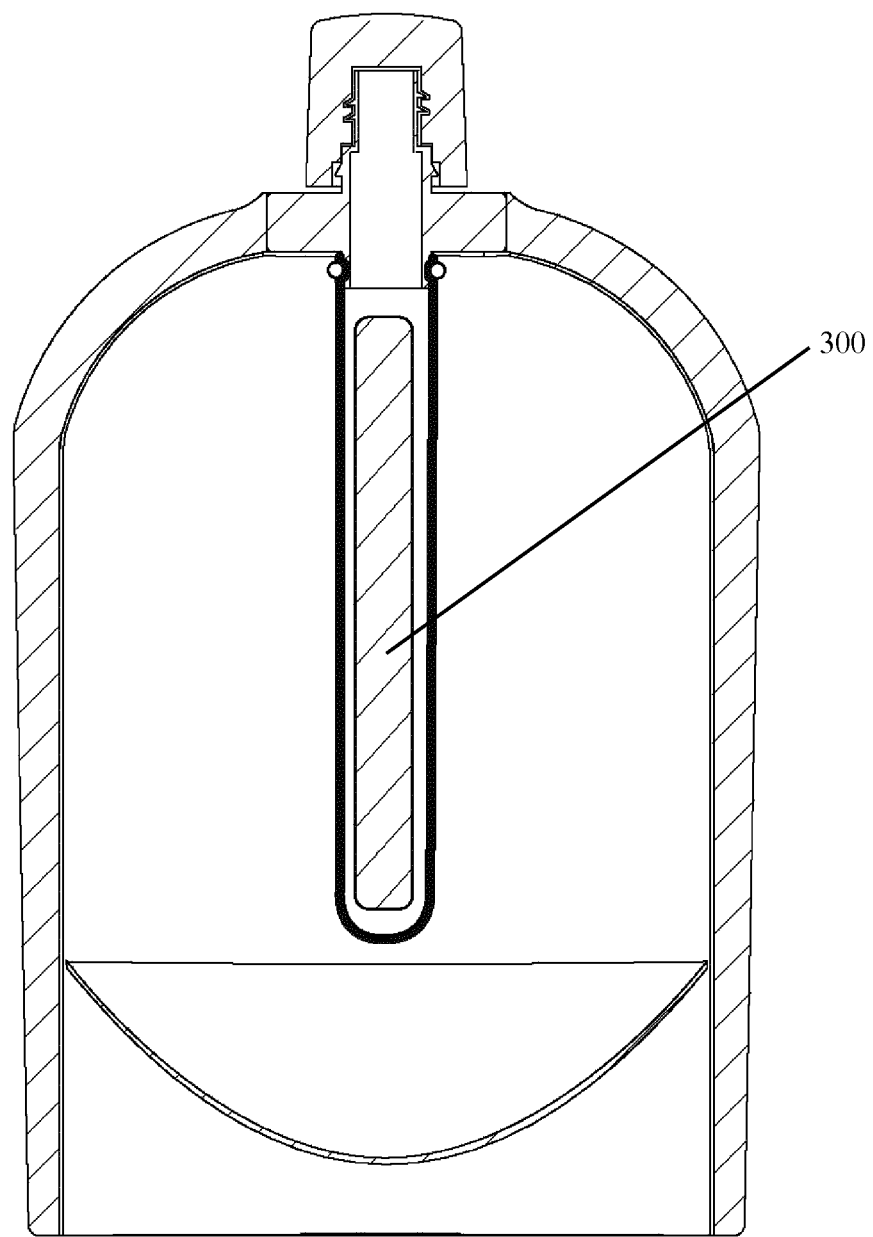
FIG. 127 is a cross sectional view of another enteral feeding apparatus according to the invention.

Referring to FIG. 127 an inner spacer such as a floating shim 300 may be located inside the elastomeric element. This ensures that as much fluid as possible is evacuated from the food pod. The shim mimics the moulding of the elastomer so that when it empties the elastomer contracts to the size of the shim to evacuate all the nutritional feed without slowing down the flow rate.

In one case the elastomeric pouch is made from a synthetic membrane. When expanded, the membrane applies a pressure on the fluid. The properties of the material ensures return to the original shape when stretched. This occurs when the fluid is inserted into the reservoir causing the material to expand. One such membrane is of a material such as silicone that is compatible with enteral feeding fluid. Enteral fluid feed can contain any one or more of protein, carbohydrate, fat, water, minerals and vitamins from a wide range of sources including dairy, soya and plant ingredients.

The pouch may comprise any suitable elastomeric material. The material preferably has a hardness on the Shore A scale. The selection of the material is based on the following properties:

protection of the food (puncture proof etc.)
output pressure (pouch squeeze), The output pressure is preferably about 10 psi
food safe
economical The material should also be capable of exhibiting a strain of ≥250% without exceeding the elastic limit of the material.

Suitable materials include the following available from Wacker:

a) Elastosil M4600A/B Hardness Shore A 20, or
b) Elastosil M4641 A/B Hardness Shore A 43.

Silpuran is a similar medical/food grade RTV silicone elastomer available from Wacker. Grade 6000/20 is an ideal material as it has a Shore A hardness of 20, a specific gravity of 1.08 g/cm$^3$, a tensile strength of 8.0 N/mm$^3$, an elongation at break of 850% and a tear resistance of 25 N/mm$^2$.

Alternatives to a) include Sorta Clear® 18
Silastic® Q7-4720
Tufel® 11-94205
Alternatives to b) include Dow Corsing® QPI-240
Square® SSR3918-40
Sorta Clear® 40
Silpuran 6000/40

The enteral feeding apparatus of the invention is adapted to deliver an overall flow rate of from 50 to 250 ml/hr.

The inputs into this system are as follows;

TABLE 1

| System inputs | | |
| --- | --- | --- |
| Pouch (Silicone Tube) | Orifice Dam/Regulator | Given Set |
| Material | Design | Material |
| Modulus | Diameter | Type and friction |
| Deformation under load | Length | Biocompatibility |
| Creep | Adjustable | Design |
| Biocompatibility | | Inner Diameter |
| Design | | Length |

TABLE 1-continued

System inputs

| Pouch (Silicone Tube) | Orifice Dam/Regulator | Given Set |
|---|---|---|
| Dimensions | | |
| Inner Diameter | | |
| Wall Thickness | | |
| Generates Pressure to drive the system | Pressure shock loss | Pressure friction loss |

For delivery of enteral food the expansile element should be as small in diameter as possible to minimize food wastage and extend in volume from rest up to fill size from 20 ml to 1000 ml without plastic deformation.

Two part RTV (Room Temperature Vulcanised) silicones are ideal for this application as they can extend to >800% without permanent deformation and have a suitable wall thickness and FOS (factor of safety) to prevent burst.

An elastomer is a polymer with viscoelasticity (having both viscosity and elasticity) and very weak inter-molecular forces, generally having low Young's/Secant modulus and high failure strain compared with other materials. An elastomer has the ability to be stretched to moderate elongations and, upon the removal of stress, return to something close to its original shape.

Silicone RTV are subject to minimal creep. In materials science, creep (sometimes called cold flow) is the tendency of a solid material to move slowly or deform permanently under the influence of mechanical stresses.

The elastomer should also be biocompatible (per ISO10995).

In the case of a low pressure coiled extension line described above used as a regulator typical dimensions are 78 inch (1981 mm), 0.06 inch ID×0.1 inch OD (1.5 mm×2.5 mm). There is also a female Luer lock and a male Luer lock. Typical materials are LDPE tube, HDPE, ABS.

The Reynolds Number for enteral fluid is highest at the highest specified flow rate (250 ml/hr) and lowest viscosity (50 cP)

$$Re_n = \frac{\rho v d}{\mu}$$

$$Re_n = \frac{(1170) \times (0.048) \times (0.0015)}{0.05}$$

$$Re_n = 2 \ll \ll 2100$$

Flow is therefore laminar and viscous.
$\rho$=Mass Density (kgm$^{-3}$)
v=velocity (ms$^{-1}$)
d=diameter of tube (m)
$\mu$=fluid viscosity (kgm$^{-1}$s$^{-1}$)

Conservation of energy (Bernoulli Equation —energy in is equal to energy out).

$$\frac{p_1}{\rho g} + \frac{v_1^2}{2g} + z_1 = \frac{p_2}{\rho g} + \frac{v_2^2}{2g} + z_2 + \text{shock loss} + \text{frictional loss}$$

Pressure head at $p_1$+ velocity head at $p_1$+ potential head at $p_1$=Pressure head at $p_2$+ velocity head at $p_2$+ potential head at $p_2$+ shock loss+frictional loss.
$p_1$=Pressure at point 1
$p_2$=Pressure at point 2
$\rho$=Mass Density (kgm$^{-3}$)
v=velocity (ms$^{-1}$)=0
g=gravity (9.81 ms$^{-1}$)
$z_1$=potential head at point 1 (m)=0
$z_2$=potential head at point 2 (m)=0

The discharge velocity is $$V=Q/A$$

V=mean velocity at any cross section A when the volume passing per second is Q (ms$^{-1}$)
Q=discharge (m$^3$s$^{-1}$)
A=cross sectional area of pipe (m$^2$)

Head loss due to friction (Darcy formula) is $$h_f = \frac{fLQ^2}{3d^5}$$

$h_f$=head loss due to friction (m)
f=resistance co-efficient

Head loss (shock loss) due to sudden contraction (vena contracta)

$$h_s = 0.5 \frac{(v^2)}{2g}$$

$h_s$=head loss due to sudden contraction (m) this is extremely low in this system as to be regarded as negligible due to the small velocities of flow involved.

Testing was carried out using enteral food which in this case, was Abbott Perative 1.3 cal/ml.

From empirical data using a coiled extension line used as friction regulator, at different lengths (0.495, 0.99, 1.981 m) achieved flows of 80-300 ml/hr.

A vena contract or orifice dam of diameter 3 mm provided negligible shock loss (Pressure$_s$ 1.16e-5, 1.6e-4 psi).

Head pressure was also negligible due to the low velocities of the enteral feed flow (Pressure $p_2$ 1.45 e-5, 2e-4 psi).

Consequently, in order to generate Pressure$_{tot}$ 0.9-1.02 psi for 80/300 ml/hr flows requires an elastomeric material of Secant modulus 0.2-0.3 MPa is required.

The hoop stress is acting circumferential and perpendicular to the axis and the radius of the cylinder wall. The hoop stress can be calculated as $$\sigma h = pd/(2t) \quad (1)$$

where
$\sigma h$=hoop stress (MPa, psi)
p=internal pressure in the tube or cylinder (MPa, psi)
d=internal diameter of tube or cylinder (mm, in)
t=tube or cylinder wall thickness (mm, in)

Longitudinal (Axial) Stress

For a cylinder closed in both ends the internal pressure creates a force along the axis of the cylinder. The longitudinal stress caused by this force can be calculated as $$\sigma l = pd/(4t) \quad (2)$$

where
$\sigma l$=longitudinal stress (MPa, psi)

The secant modulus of elasticity of the Pouch material and the pressure in the Pouch dictates the wall thickness of the pouch. The higher the secant modulus of the material used the lower the wall thickness to produce the same pressure.

A maximum secant modulus of 1.6 Mpa at break gives a wall thickness of 0.1 mm wall thickness at a pressure of 1 psi and discharge of 80 or 300 ml/hr.

The pressure applied by the expansile element may be from 0.05 to 900 psi.

In the following tables E-OX is $10^{-x}$, for example E-07 is $10^{-7}$.

The maximum desired pressure for the elastomeric material is in the order of 6.3 MPa or 900 psi.

| Q (ml/hr) | Q (m3/s) | D (m) | L (m) | f | $h_f$ | Pa | MPa | psi |
|---|---|---|---|---|---|---|---|---|
| 1000 | 2.77E−07 | 9.30E−04 | 3 | 5 | 5.51E+02 | 6329503.857 | 6.3 | 906 |

This is illustrated by 1000 ml/hr flow (hydration) and a coiled restrictor of 3 m long with a diameter of 0.93 mm 100 psi is generally accepted as the maximum pressure for liquid packaging.

3 psi=Maximum flow 1500 m/hr, max tube diameter with ENFit connector, approximately 4 mm and a tube length of 2 meters.

| Q (ml/hr) | Q (m3/s) | D (m) | L (m) | f | $h_f$ | Pa | MPa | psi |
|---|---|---|---|---|---|---|---|---|
| 1500 | 4.16E−07 | 4.00E−03 | 2 | 15 | 1.69E+00 | 19397.313 | 0.019 | 2.77 |

Minimum pressure is dictated by the flow of 1 ml/hr and a coiled restrictor of 3 m long with a diameter of 0.5 mm. 0.5 mm is the diameter of the coiled tube. Any smaller ID is liable to block with enteral feed or colostrum.

| Q (ml/hr) | Q (m3/s) | D (m) | L (m) | f | $h_f$ | Pa | Mpa | psi |
|---|---|---|---|---|---|---|---|---|
| 1 | 2.77E−10 | 5.00E−04 | 3 | 15 | 3.68E−02 | 422.7227728 | 0.00042 | 0.060 |

0.5 psi

The flow rate can be restricted by either of the following 2 methods, 80 ml/hr with a short coil of 1 m length

| Q (ml/hr) | Q ($m^3 s^{-1}$) | Length (m) | Diameter (m) | F (resistance co-efficient) | $h_f$ (m) | Pressure$_f$ (Pa) | Pressure$_f$ (psi) |
|---|---|---|---|---|---|---|---|
| 80 | 2.22E−08 | 0.99 | 0.0015 | 14 | 0.30 | 3441.49 | 0.50 |

1500 ml/hr with just a Vena contractra

| Q (ml/hr) | Q (m3/s) | D (m) | A ($m^2$) | V | $h_s$ | Pa | psi |
|---|---|---|---|---|---|---|---|
| 1500 | 4.16E−07 | 5.00E−04 | 1.96E−07 | 2.12E+00 | 0.183213856 | 2102.87 | 0.301 |

The range of pressure applied by the expansile material in one cases is from 1 to 2.5 psi.

This is particularly suitable for delivery of flow rates in the range of 50 to 500 ml/hr.

| Discharge | | Coiled Tube Regulator | | f | | | |
|---|---|---|---|---|---|---|---|
| (Q) ml/hr | (Q) $m^3 s^{-1}$ | Length (m) | Diameter (m) | (resistance co-efficient) | $h_f$ (m) | Pressure$_f$ (Pa) | Pressure$_f$ (psi) |
| 80 | 2.22E−08 | 0.495 | 0.0015 | 14 | 0.15 | 1720.74 | 0.25 |
| | | 0.99 | | | 0.30 | 3441.49 | 0.50 |
| | | 1.981 | | | 0.60 | 6886.46 | 9.99E−01 |

-continued

| Discharge | | Coiled Tube Regulator | | f | | | |
|---|---|---|---|---|---|---|---|
| (Q) ml/hr | (Q) m³s⁻¹ | Length (m) | Diameter (m) | (resistance co-efficient) | $h_f$ (m) | Pressure$_f$ (Pa) | Pressure$_f$ (psi) |
| 300 | 8.83E−08 | 0.495 | | 3.6 | 0.61 | 7000.14 | 1.02E+00 |
| | | 0.99 | | | 4.74 | 54445.50 | 7.90 |
| | | 1.981 | | | 9.49 | 108945.99 | 15.80 |

The volume of the expansile element can be from 1 ml to 1500 ml, in some cases 10 to 1500 ml or to 1500 ml.

Common sizes are from 20 ml to 1000 ml.

Most common used size is 500 ml.

The wall thickness of the expansile element in the expanded filled configuration may be from 0.01 mm to 1.0 mm, 0.05 to 1.0 mm, 0.1 to 0.5 mm or about 0.2 mm The secant modulus of elasticity of the expansile element in the expanded filled configuration at a circumferential extension of from 100-1000 is from 422 Pa to 6.3 MPa.

The maximum desired Secant Modulus for the elastomer is in the order of 6.3 MPa to overcome the maximum frictional head loss as follows;

| Q (ml/hr) | Q (m3/s) | D (m) | L (m) | f | $h_f$ | Pa | MPa | psi |
|---|---|---|---|---|---|---|---|---|
| 1000 | 2.77E−07 | 9.30E−04 | 3 | 5 | 5.51E+02 | 6329503.857 | 6.3 | 906 |

That is for 1000 ml/hr flow rate with a 0.9.3 mm, 3 m long coiled tube.

The minimum desired Secant Modulus for the elastomer is in the order of 422 Pa. to overcome the minimal head loss as follows;

| Q (ml/hr) | Q (m3/s) | D (m) | L (m) | f | $h_f$ | Pa | MPa | psi |
|---|---|---|---|---|---|---|---|---|
| 1 | 2.77E−10 | 5.00E−04 | 3 | 15 | 3.68E−02 | 422.7227728 | 0.00042 | 0.060 |

That is for 1 m/hr flow rate with a 0.5 mm, 3 m long coiled tube.

The circumferential extension in some cases is from 300-500%.

| | Centimetres | | | | Milli-litre (ml) |
|---|---|---|---|---|---|
| | Length | Diameter | Wall Thickness | Outer Diameter | Circumference (tube/pouch) | |
| Starting dimensions of tube | 10 | 1.4 | 0.1 | 1.5 | 5.03 | 15.39 |
| Pouch dimensions full | 17 | 6.8 | 0.1 | 7 | 21.99 | 617.39 |
| Pouch dimensions in use (300 ml/hr) | 17 | 4.8 | | 5 | 15.71 | 307.62 |
| | | | | | Circumference Ratio | 3.125 4.375 >400% |

The elastomer of choice is Silpuran 6000/20 this has a Secant modulus at break of between 0.1 and 0.9 Mpa

| Discharge (Q) ml/hr | (Q) m³s⁻¹ | Hoop stress ($\sigma_s$) (Pa) (wall thickness calculated at 3e-4m) | Longitudinal stress ($\sigma_h$) (Pa) | Empirical E (Pa) |
|---|---|---|---|---|
| 80 | 2.22E−08 | 459097.0691 | 286935.6682 | 153032.4 |
| 300 | 8.83E−08 | 466675.6778 | 291672.2986 | 155558.6 |

| Silpuran (Medical and food grade certified) | Shore | TS N/mm² at Break | Elongation Break % | Secant Modulus at Break (MPa) | Secant Modulus at Break (Pa) | Wall thickness of Pod delivering 80 or 300 ml/hr (mm) |
|---|---|---|---|---|---|---|
| 6000/20 | 20A | 8 | 850 | 0.94 | 941175.47 | 0.18594 |

The barrier may be a laminate of two or more layers. One such material which is available from Bemis Packaging is: 12 μm/20 μm/12 μm/65 μm PET/LLDPE/FOIL (AI)/PE white weld laminate PET—Barrier layer to oxygen egress and ingress
LLDPE—Bond layer and colourant carrier
Foil—Barrier layer to all ingress and egress typical aluminium
PE—Weld layer.

The enteral feeding apparatus of the invention reduces the steps required to set up and start operation down to less than ten. This is a valuable advancement for the end-user. The apparatus is a safe, simple, reliable and an economical solution that:

supports an active patient lifestyle
has no alarms, meaning less disruption to the patients lifestyle and at night
reduces the need for the use of complicated infusion pumps
allows patients to be treated at home, as well as out and about in the community
is easy to use, reduces training costs
minimizes multiple nursing visits
has a selection of volumes and flow rates
does not require a power source
reduction in maintenance time and cost In some cases the food pod may incorporate a means to identify how much feed is left within it such as a clear panel window in the packaging. Such as means may include a sensor to allow for the data to be received and then passed to an electronical device. Sensors that may be used include the following.

Graphene is a two-dimensional material made of carbon atoms. It is 200 times stronger than steel at one atom thick and is highly conductive. A graphene sensor may be provided into/on/through the elastomeric pouch to allow for accurate pressure/quantity readings. This can allow the user to use a form of connectivity to generate data.

A copper sensor can be used as an antenna like RFID to transmit a radio wave through the feed to detect the size of the elastomeric pod and hence they quantity feed. Copper sensors are extremely sensitive and are completely wireless. Copper sensors are used for the measurement of pressure using two strips of copper acting like radio antennas and a specially designed rubber to be sandwiched in between. As pressure is put on the sensor, the material of the pouch changes thickness and a copper sensor may be used to detect this change. The sensor may be used to detect how much pressure is inside the elastomeric pouch by placing it in or on the elastomeric wall itself or placed around the wall. A simple flexible sensor may be used. It acts as a resistor which varies the voltage in a circuit. As the sensor is flexed, the resistance across the sensor increases and the circuit's voltage reading decreases. One such sensor is https://www.amazon.com/SPECTRA-SYMBOL-FS-L-0112-103-ST-SYMBOLFLEX-SENSOR/dp/B005T8743E The flow of enteral fluid can be monitored using an infrared or an ultrasonic flow meter. The flow sensor can be used to detect the flow rate of the fluid as it flows through the given set. Ultrasonic flow meters can be implemented on the outside of the tubing without having direct contact with the feed. Infrared flow meters are generally in-line and in some cases are also known as rotameters.

Examples of Ultrasonic flow meters are described at:
http://www.flowmeters.com/ultrasonic-technology
http://www.smdsensors.com/Products/UF31210-Clamp-on-Ultrasonic-Flow-Sensor/
http://www.smdsensors.com/Products/UF10500-In-line-Ultrasonic-Flow-Sensor/

One example of an infrared flowmeter is:
http://www.swissflow.com/sf800.html

The apparatus may include a smart label. In some cases the apparatus may comprise a smart tag such as a Near Field Communication (NFC) tag.

With the addition on NFC if a sensor can engage the product to detect weight the NFC will be able to transmit the small amount of data to any smart technology or NFC readers which are currently available.

The invention is not limited to the embodiments hereinbefore described, which may be varied in construction and detail.

The invention claimed is:

1. A portable enteral feeding apparatus comprising
a pouch which defines a reservoir for enteral fluid and having an outlet for delivery of enteral fluid from the pouch, the pouch being formed by an expansile element having an expanded filled configuration and a collapsed configuration, expansion of the expansile element applying a pressure, providing the sole force under which enteral fluid is delivered from the pouch during collapse of the pouch,
a substantially gas impermeable barrier surrounding the pouch, and
a regulator comprises a friction regulator comprising a plurality of different flow rate coiled tubes and particular flow rate coiled tubes being selected based on a desired flow rate of enteral fluid.

2. The enteral feeding apparatus as claimed in claim 1 wherein, when the pouch is filled with enteral fluid, the pouch substantially conforms to the shape of the inner surface of the surrounding barrier, wherein the barrier comprises a membrane, and wherein the membrane comprises a laminate including a metallic layer.

3. The enteral feeding apparatus as claimed in claim 1 wherein, as fluid is delivered from the pouch, a space is formed between the pouch and the barrier.

4. The enteral feeding apparatus as claimed in claim 1 comprising an inner barrier which is surrounded by the expansile element.

5. The enteral feeding apparatus as claimed in claim 1 wherein the apparatus is free-standing, and wherein the pouch comprises a bottom gusset.

6. The enteral feeding apparatus as claimed in claim 1 wherein the coiled tubes are configured for engagement with one another to adjust the length of the regulator, and wherein the coiled tubes have indicia to indicate a set outlet flow rate.

7. The enteral feeding apparatus as claimed in claim 1 wherein the regulator comprises an inlet port having engagement features for engagement with connector and an outlet port having engagement features for engagement with a connector.

8. The enteral feeding apparatus as claimed in claim 1 wherein the pressure applied by the expansile element in the expanded configuration is
from 0.05 to 90 psi (0.000345 MPa to 0.62053 MPa).

9. The enteral feeding apparatus as claimed in claim 1 wherein a volume of the expansile element in the expanded filled configuration is from 250 ml to 750 ml.

10. The enteral feeding apparatus as claimed in claim 1 wherein a wall thickness of the expansile element in the expanded filled configuration is from 0.05 mm to 1.0 mm.

11. The enteral feeding apparatus as claimed in claim 1 wherein a secant modulus of elasticity of the expansile element in the expanded filled configuration at a circumferential extension of from 100% to 1000% is from 0.1 to 4.5 MPa.

12. The enteral feeding apparatus as claimed in claim 1 wherein the apparatus is configured to deliver a flowrate of from 50 to 1000 ml/hr.

13. The enteral feeding apparatus as claimed in claim 1 wherein the expansile element comprises a silicon elastomer.

\* \* \* \* \*